US008084576B2

(12) United States Patent
Glover et al.

(10) Patent No.: US 8,084,576 B2

(45) Date of Patent: Dec. 27, 2011

(54) CANCER ASSOCIATED GLUCOSE TRANSPORTER 8 VARIANT

(75) Inventors: Nicholas Ronald Glover, Oakville (CA); Glen Christopher MacDonald, Winnipeg (CA); Joycelyn Entwistle, Winnipeg (CA); Jeannick Cizeau, Winnipeg (CA); Francina C. Chahal, Winnipeg (CA)

(73) Assignee: Viventia Biotechnologies Inc., Mississauga, Ontario (CA)

( * ) Notice: Subject to any disclaimer, the term of this patent is extended or adjusted under 35 U.S.C. 154(b) by 946 days.

(21) Appl. No.: 11/722,420

(22) PCT Filed: Dec. 21, 2005

(86) PCT No.: PCT/CA2005/001953
§ 371 (c)(1),
(2), (4) Date: Jun. 21, 2007

(87) PCT Pub. No.: WO2006/066408

PCT Pub. Date: Jun. 29, 2006

(65) Prior Publication Data

US 2010/0254982 A1 Oct. 7, 2010

Related U.S. Application Data

(60) Provisional application No. 60/637,448, filed on Dec. 21, 2004.

(51) Int. Cl.

| | |
|---|---|
| ***C07K 1/00*** | (2006.01) |
| ***C07K 14/00*** | (2006.01) |
| ***C07K 17/00*** | (2006.01) |
| ***A61K 36/16*** | (2006.01) |
| *C07K 21/02* | (2006.01) |
| *C07K 21/04* | (2006.01) |

(52) U.S. Cl. ........................ 530/350; 530/358; 536/23.1

(58) Field of Classification Search ........................ None
See application file for complete search history.

(56) References Cited

U.S. PATENT DOCUMENTS

| | | | | |
|---|---|---|---|---|
| 6,051,229 | A | 4/2000 | Handley et al. | |
| 2002/0038464 | A1 | 3/2002 | Charron et al. | |
| 2003/0228592 | A1 * | 12/2003 | Rogers et al. | 435/6 |
| 2005/0202559 | A1 | 9/2005 | Pownall et al. | |

FOREIGN PATENT DOCUMENTS

| | | |
|---|---|---|
| JP | 06-141884 A2 | 5/1994 |
| WO | WO 94/16726 A1 | 8/1994 |
| WO | 199855623 | 12/1998 |
| WO | 200104145 | 1/2001 |

OTHER PUBLICATIONS

Skolnick and Fetrow. From genes to protein structure and function: novel applications of computational approaches in the genomic era. Trends in Biotechnology, 2000. vol. 18, pp. 34-39.*

Burgess, Shaheen, Ravera, Jaye, Donohue, and Winkles. Possible dissociation of the heparin binding and mitogenic activities of heparin binding (acidic fibroblast) growth factor-1 from its receptor binding activities by site directed mutagenesis of a single lysine residue. Journal of Cell Biology, 1990. vol. 111, pp. 2129-2138.*

Lazar, Watanabe, Dalton, and Sporn. Transforming growth factor alpha: mutation of aspartic acid 47 and leucine 48 results in different biological activities. Molecular and Cellular Biology, 1988. vol. 8, pp. 1247-1252.*

Aotsuka, Y. et al.: "Identification of a malignant cell associated antigen recognized by a human monoclonal antibody" European Journal of Cancer & Clinical Oncology. May 1988. vol. 24, No. 5, pp. 829-838. See whole document.

Hagiwara, H. et al.: "Determination of the antigen/epitope that is recognized by Human Monoclonal Antibody CLN-IgG" Human Antibodies. 2001. vol. 10, No. 2, pp. 77-82. See whole document.

Osumi, K. et al.: "Antibody dependent cell mediated cytotoxicity on human cervical carcinoma cell line, ME-180, with human monoclonal antibody" Cancer Letters. 1992. vol. 62, No. 2, pp. 179-183. See whole document.

Fenstermaker, R. et al.: "Immunotherapeutic strategies for malignant glioma" Cancer Control. May/Jun. 2004. vol. 11, No. 3, pp. 181-191. See p. 187, left column, 3rd paragraph.

Shikhman, A. R., et al.: "Distinct pathways regulate faciliated glucose transport in human articular chondrocytes during anabolic and catabolic responses" American Journal of Physiology-Enocrinology and Metabolism. Jan. 28, 2004. vol. 286, pp. E980-E985. See whole document.

Kreitman, R.J.: "Immunotoxins in cancer therapy" Current Opinion in Immunology. 1999. vol. 11, No. 5, pp. 570-578. See whole document.

Moadel R.M., et al.: "Positherapy: targeted nuclear therapy for breast cancer with 18F-2-deoxy-2-fluoro-D-glucose" Cancer Research. Feb. 1, 2005. vol. 65, No. 3, pp. 698-702. See whole document.

Joost, H.G. et al.: "The extended GLUT-family of sugar/polyol transport facilitators: nomenclature, sequence characteristics, and potential function of its novel members (review)" Molecular Membrane Biology 2001 vol. 18, No. 4, pp. 247-256. Rogers, S. et al.: "Differential expression of GLUT12 in breast cancer and normal breast tissue" Cancer Letters (2003) vol. 193, No. 2, pp. 225-233.

Shin B.C., et al.: "Glucose transporter GLUT8 translocation in neurons is not insulin responsive" J. Neurosci. Res. (2004) vol. 75, No. 6, pp. 835-844.

Chen Y. et al.: "Expression and regulation of glucose transporter 8 in rat Leydig cells" J. Endocrinol. (2003) vol. 179, No. 1, pp. 63-72.

Doege, H. et al.: "GLUT8, a novel member of the sugar transport facilitator family with glucose transport activity" J. Biol. Chem. (2000) vol. 275, No. 21, pp. 16275-16280.

Ibberson, M. et al.: "GLUTX1, a novel mammalian glucose transporter expressed in the central nervous system and insulin-sensitive tissues" J Biol. Chem. (2000) vol. 275, No. 7, pp. 4607-4612.

Macheda, M.L. et al.: "Molecular and cellular regulation of glucose transporter (GLUT) proteins in cancer" Journal of Cellular Physio. (2005) vol. 202, pp. 654-662.

Goldman Na et al. GLUT1 and GLUT8 in endometrium and endometrial adenocarcinoma. Mod.Pathol. 2006.

Schmidt U. et al. Endocytosis of the glucose transporter GLUT8 is mediated by interaction of a dileucine motif with the beta2-adaptin subunit of the AP-2 adaptor complex. J Cell Sci. 2006;119:2321-2331.

Lisinski, I., et al., "Targeting of GLUT6 (formerly GLUT9) and GLUT8 in rat adipose cells", Biochem. J., 2001, vol. 358, pp. 517-522.

* cited by examiner

*Primary Examiner* — Anne M. Gussow

(74) *Attorney, Agent, or Firm* — Bereskin & Parr LLP/S.E.N.C.R.L., s.r.l.; Micheline Gravelle

(57) ABSTRACT

The present invention provides the amino acid and nucleic acid sequences of heavy chain and light chain complementarity determining regions of a cancer specific antibody. In addition, the invention provides cancer specific antibodies and immunoconjugates comprising the cancer specific antibody attached to a toxin or label, and methods and uses thereof. The invention also relates to diagnostic methods and kits using the cancer specific antibodies of the invention. Further, the invention provides a novel cancer-associated antigen and its uses thereof.

7 Claims, 15 Drawing Sheets

$V_L$ (SEQ ID NOS: 8 and 7)

```
GAC ATC CAG ATG ACC CAG TCT CCA TCC TCA CTG TCT GCA TCT GTA GGA GAC AGA GTC
 D   I   Q   M   T   Q   S   P   S   S   L   S   A   S   V   G   D   R   V

ACC ATC ACT TGT CGG GCG AGT CAG GAC ATT AGT AAT TAT TTA GCC TGG TTT CAG
 T   I   T   C   R   A   S   Q   D   I   S   N   Y   L   A   W   F   Q
                |----------- CDR 1 (L) -----------|

CGG AAA CCA GGG AAA GCC CCT AAG TCC CTG ATC TAT GCT GCA TCC AGT TTG CAC
 R   K   P   G   K   A   P   K   S   L   I   Y   A   A   S   S   L   H
                                                 |--- CDR 2 (L) ---

AGT AAG GTC CCA ACA CAA TTC AGC GGC AGT GGA TCT GGG ACA GAT TTC ACT CTC
 S   K   V   P   T   Q   F   S   G   S   G   S   G   T   D   F   T   L
-|

ACC ATC AGC AGC CTG CAG CCT GAA GAT TTT GCA ACT TAT TAC TGC CTA CAG TAT
 T   I   S   S   L   Q   P   E   D   F   A   T   Y   Y   C   L   Q   Y
                                                             |---------

AGT ACT TAC CCT ATC ACC TTC GGC GGA GGG ACC AAG GTG GAG ATC AAA CGA
 S   T   Y   P   I   T   F   G   G   G   T   K   V   E   I   K   R
CDR 3(L) ------------|
```

Figure 2:
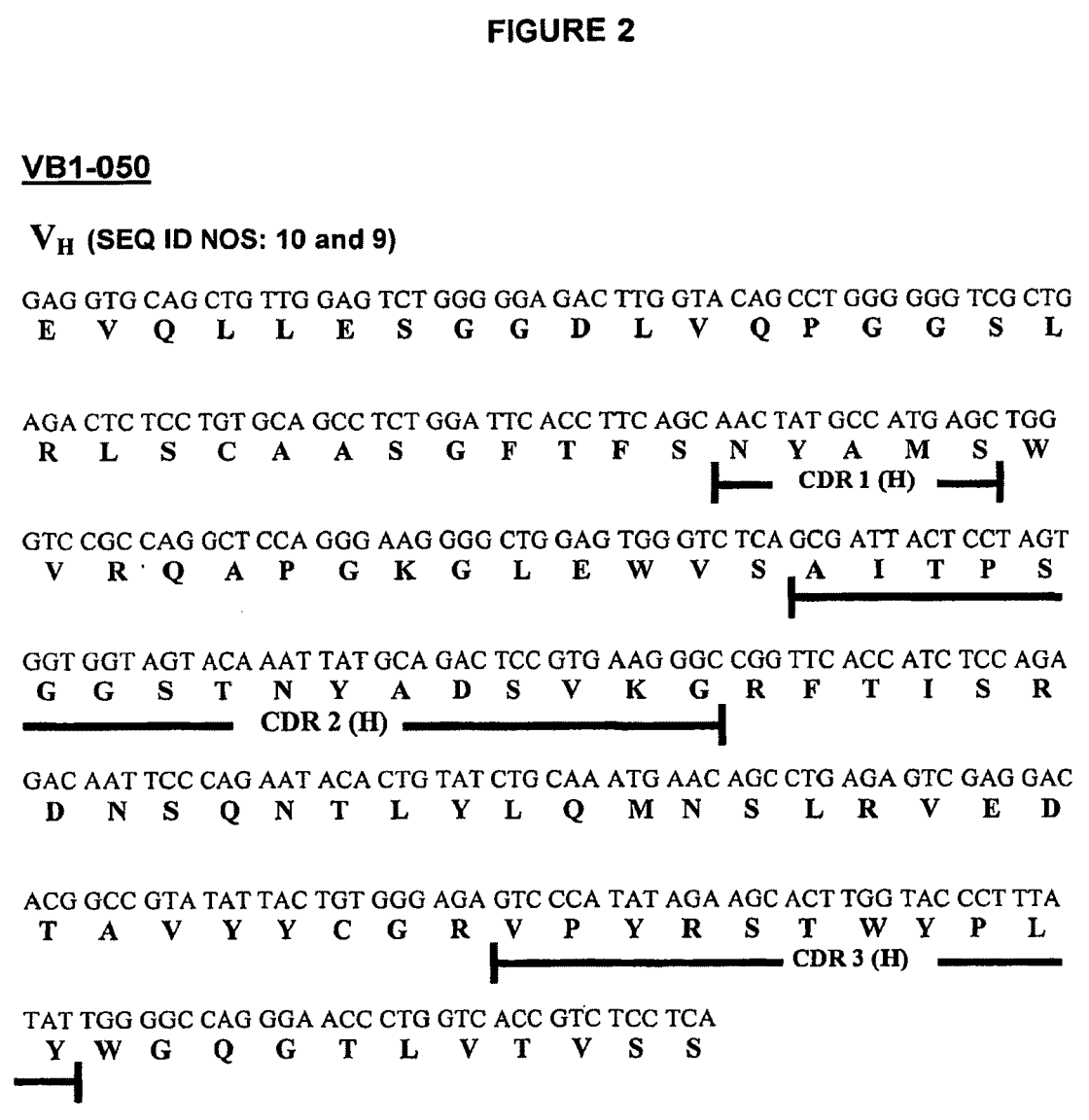

$V_H$ (SEQ ID NOS: 10 and 9)

GAG GTG CAG CTG TTG GAG TCT GGG GGA GAC TTG GTA CAG CCT GGG GGG TCG CTG
E V Q L L E S G G D L V Q P G G S L

AGA CTC TCC TGT GCA GCC TCT GGA TTC ACC TTC AGC AAC TAT GCC ATG AGC TGG
R L S C A A S G F T F S N Y A M S W
CDR 1 (H)

GTC CGC CAG GCT CCA GGG AAG GGG CTG GAG TGG GTC TCA GCG ATT ACT CCT AGT
V R Q A P G K G L E W V S A I T P S

GGT GGT AGT ACA AAT TAT GCA GAC TCC GTG AAG GGC CGG TTC ACC ATC TCC AGA
G G S T N Y A D S V K G R F T I S R
CDR 2 (H)

GAC AAT TCC CAG AAT ACA CTG TAT CTG CAA ATG AAC AGC CTG AGA GTC GAG GAC
D N S Q N T L Y L Q M N S L R V E D

ACG GCC GTA TAT TAC TGT GGG AGA GTC CCA TAT AGA AGC ACT TGG TAC CCT TTA
T A V Y Y C G R V P Y R S T W Y P L
CDR 3 (H)

TAT TGG GGC CAG GGA ACC CTG GTC ACC GTC TCC TCA
Y W G Q G T L V T V S S

FIGURE 11
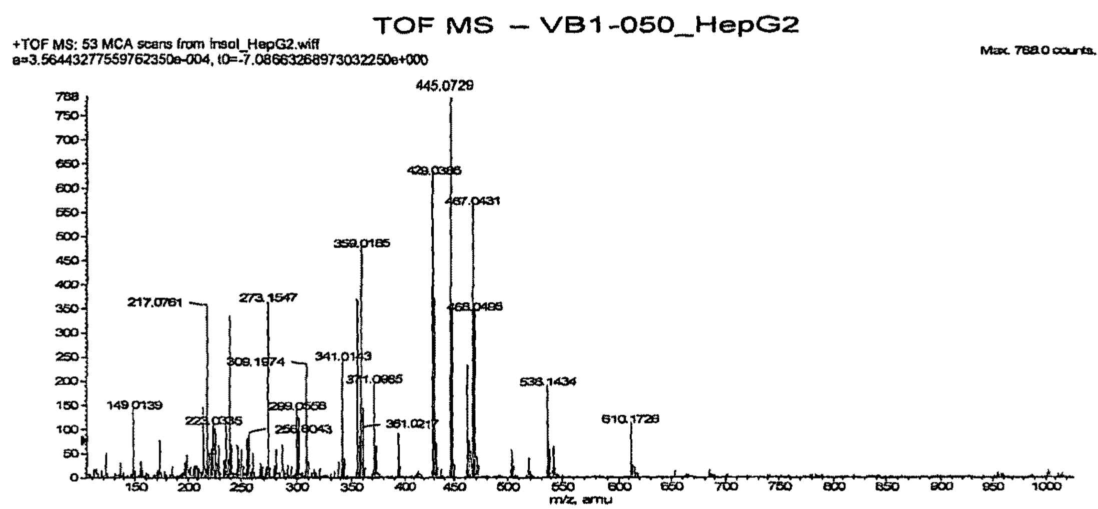
Mass reconstruction of VB1-050_HepG2
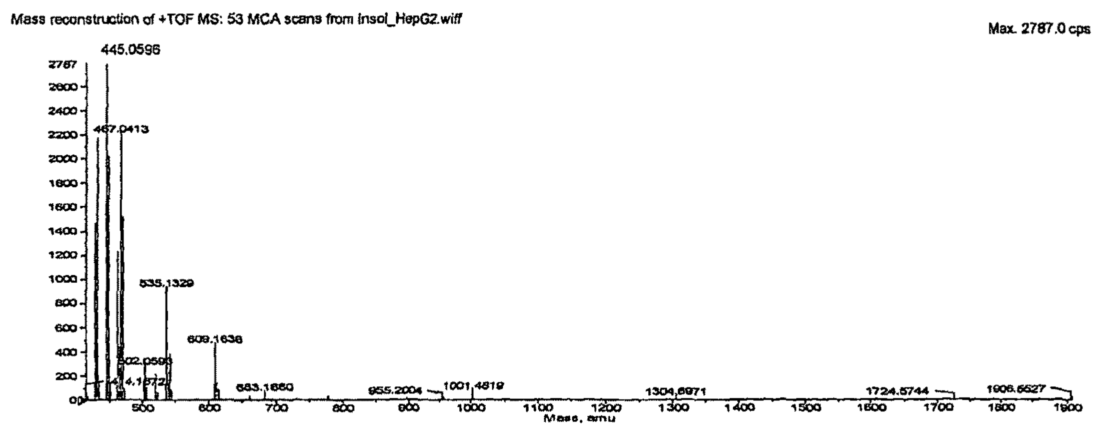

FIGURE 12
TOF MS for VB1-050_Panc-1
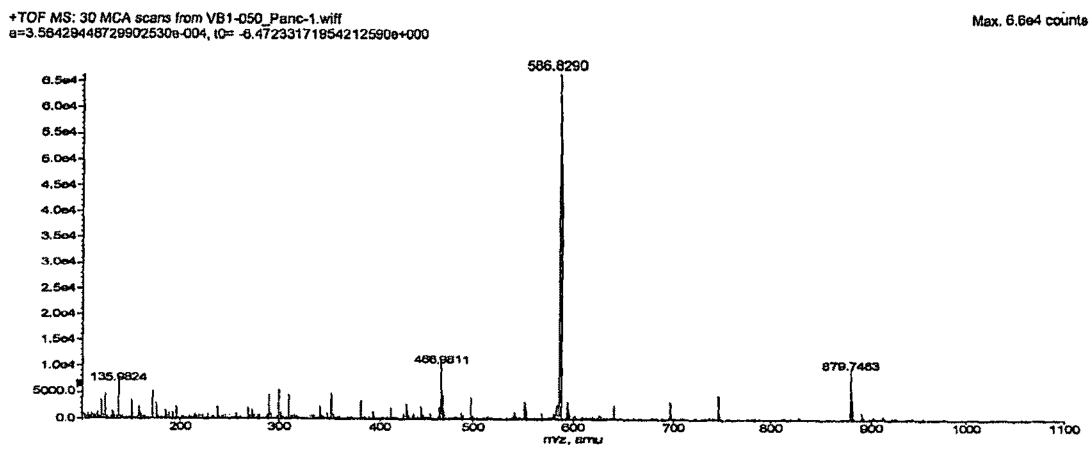
Mass reconstruction of VB1-050_Panc-1
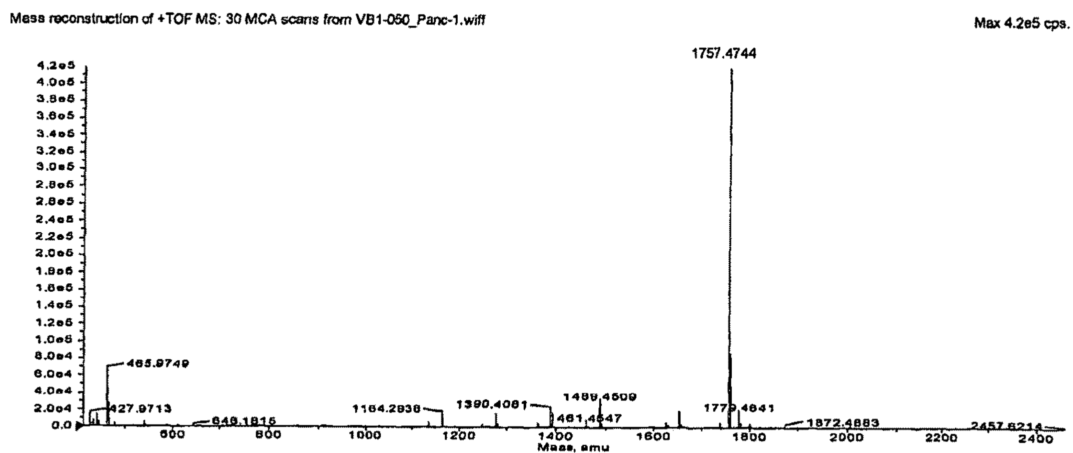

FIGURE 13
TOF-MS VB1-050_MCF-7
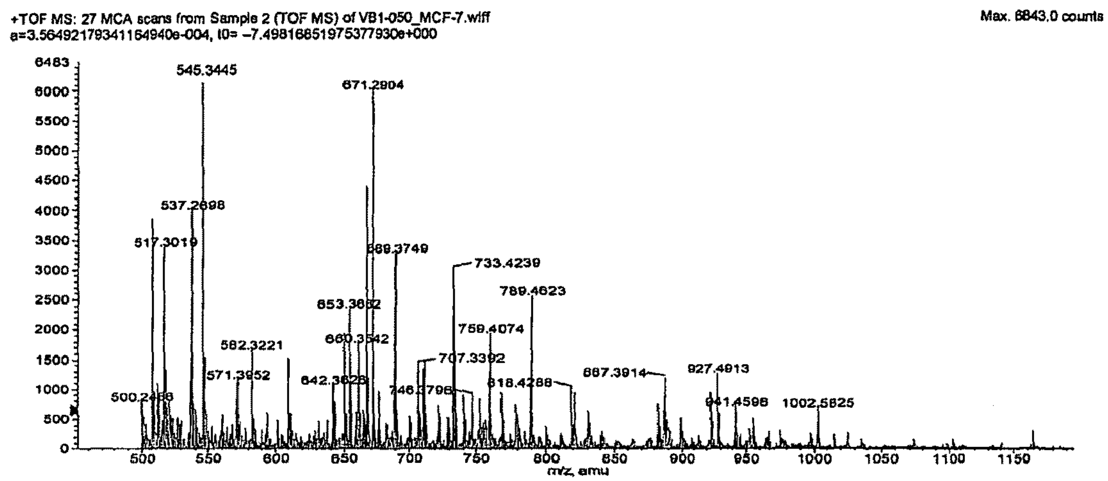
Mass reconstruction of VB1-050_MCF-7
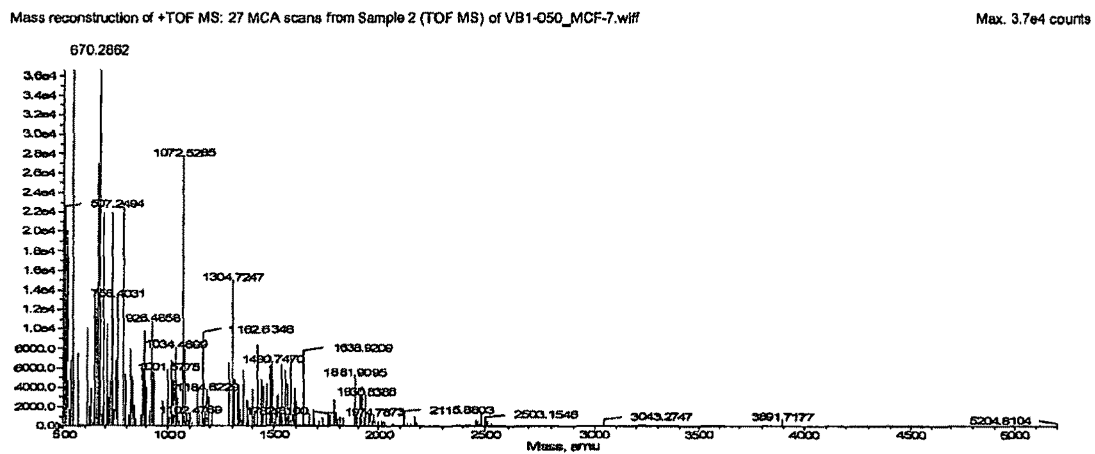

FIGURE 14
TOF MS-VB1-050_C-33A
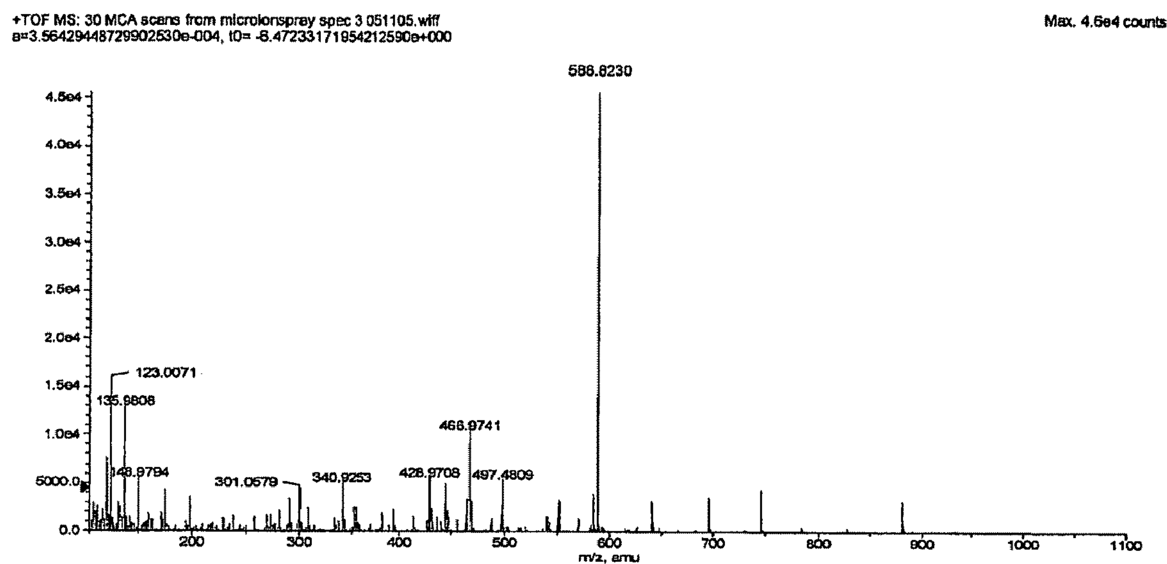
Mass reconstruction of VB1-050_C33A
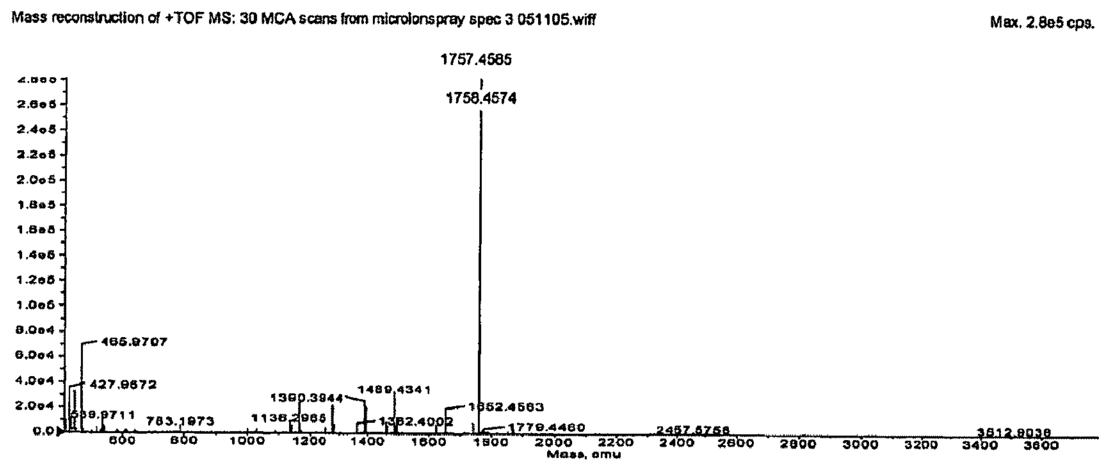

FIGURE 15

SEQ ID NO: 11

```
    MTPEDPSETE PAAPRPGASA PRGRRVFLAA FAAALGPLSF GFALGYSSPA
 51 IPSLQRAAPP APRLDDAAAS WFGAVVTLGA AAGGVLGGWL VDRAGRKLSL
101 LLCSVPFVAG FAVITAAQDV WMLLGGRLLT GLACGVASLV APVYISEIAY
151 PAVRGLLGSC VQLMVVVGIL LAYLAGWVLE WRWLAVLGCV PPSLMLLLMC
201 FMPETPRFLL TQHRRQEAMA ALRFLWGSEQ GWEDPPIGAE QSFHLALLRQ
251 PGIYKPFIIG VSLMAFQQLS GVNAVMFYAE TIFEEAKFKD SSLASVVVGV
301 IQVLFTAVAA LIMDRAGRRL LLVLSGVVMV FSTSAFGAYF KLTQGGPGNS
351 SHVAISAPVS AQPVDASVGL AWLAVGNMCL FIAGFAVGWG PIPWLLMSEI
401 FPLHVKGVAT GICVLTNWLM AFLVTKEFSS LMEVLRPYGA FWLASAFCIF
451 SVLFTLFCVP EIKGKTLEQI TAHFEGR
```

FIGURE 16

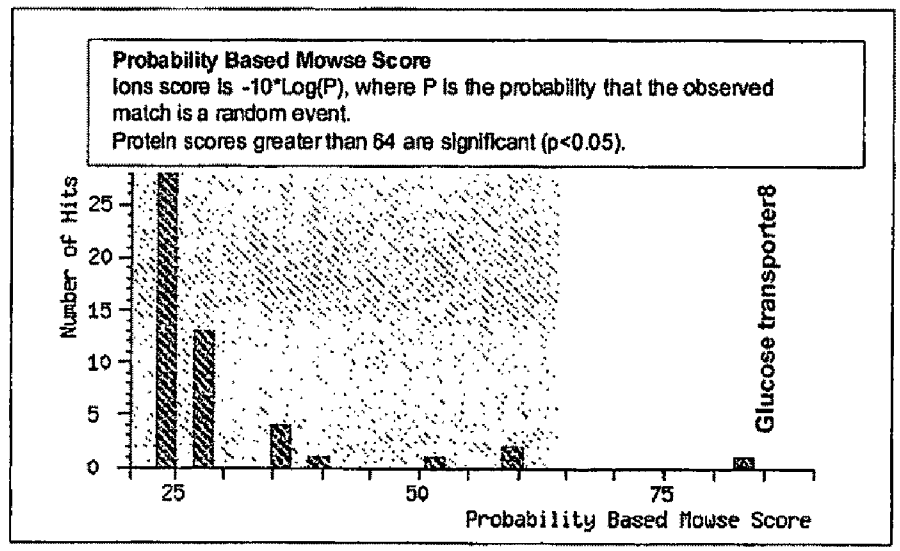

FIGURE 17

| | Accession | Mass | Score | Description |
|---|---|---|---|---|
| 1 | gi\|7018306 | 50858 | 83 | glucose transporter 8 [Homo sapiens] |
| 2 | gi\|7688146 | 50792 | 61 | glucose transporter 8 [Homo sapiens] |
| 3 | gi\|21361449 | 50818 | 61 | solute carrier family 2, (facilitated glucose transporter) member 8 [Homo sapiens] |
| 4 | gi\|55665089 | 43470 | 52 | solute carrier family 2, (facilitated glucose transporter) member 8 [Homo sapiens] |
| 5 | gi\|55665088 | 27790 | 40 | solute carrier family 2, (facilitated glucose transporter) member 8 [Homo sapiens] |
| 6 | gi\|22749173 | 31126 | 35 | hypothetical protein LOC157983 [Homo sapiens] |
| 7 | gi\|62860046 | 123247 | 34 | zinc finger, RAN-binding domain containing 3 [Homo sapiens] |
| 8 | gi\|42657033 | 13184 | 34 | PREDICTED: hypothetical protein XP_379299 [Homo sapiens] |
| 9 | gi\|21754605 | 42167 | 34 | unnamed protein product [Homo sapiens] |
| 10 | gi\|913281 | 9360 | 29 | dopamine D4 receptor; DRD4 [Homo sapiens] |
| 11 | gi\|4100621 | 35815 | 29 | WASP interactor protein [Homo sapiens] |
| 12 | gi\|10863977 | 10834 | 28 | LSM2 homolog, U6 small nuclear RNA associated [Homo sapiens] |
| 13 | gi\|54695676 | 22023 | 28 | claudin 11 (oligodendrocyte transmembrane protein) [Homo sapiens] |
| 14 | gi\|10938016 | 21993 | 28 | claudin 11 [Homo sapiens] |
| 15 | gi\|20372496 | 12576 | 28 | anti-acetylcholine receptor immunoglobulin heavy chain variable region [Homo sapiens] |
| 16 | gi\|3283415 | 23363 | 28 | oligodendrocyte-specific protein [Homo sapiens] |
| 17 | gi\|609455 | 14106 | 28 | This CDS feature is included to show the translation of the corresponding V_region |
| 18 | gi\|55957504 | 26342 | 27 | novel protein similar to semaphorins [Homo sapiens] |
| 19 | gi\|47077813 | 59197 | 27 | unnamed protein product [Homo sapiens] |
| 20 | gi\|57208269 | 35223 | 27 | chromosome 20 open reading frame 160 [Homo sapiens] |

FIGURE 18

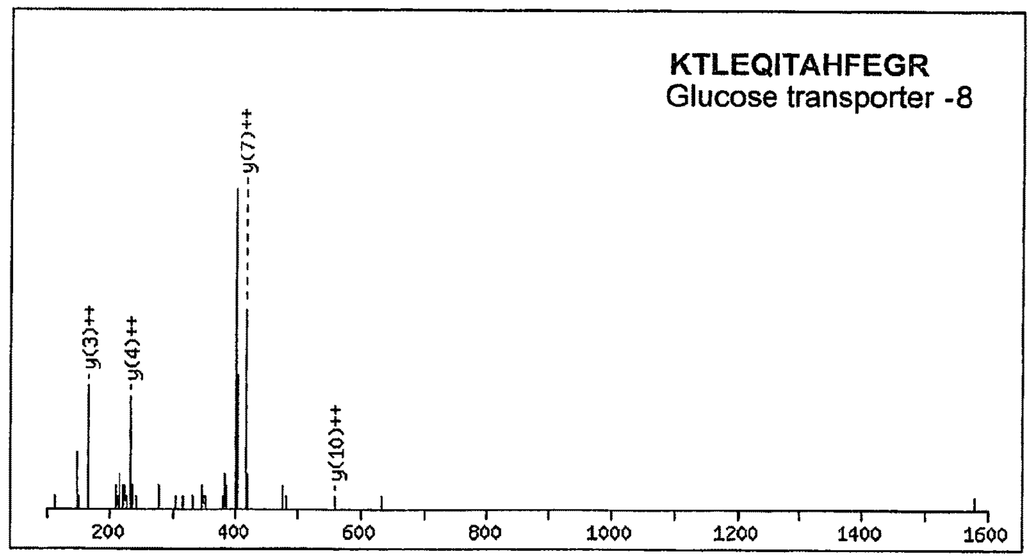

Monoisotopic mass of neutral peptide Mr(calc): 1401.54 Ions Score: 73 Expect: 1.3e+02
Matches ( Bold Red ): 4/140 fragment ions using 12 most intense peaks

Monoisotopic mass of neutral peptide Mr(calc): 1070.63 Ions Score: 68 Expect: 5.6e+02
Matches ( Bold Red ): 7/86 fragment ions using 36 most intense peaks

Monoisotopic mass of neutral peptide Mr(calc): 1997.9992 Ions Score: 18
Expect: 2.6e+02 Matches ( Bold Red ): 6/172 fragment ions using 18 most intense peaks

Monoisotopic mass of neutral peptide Mr(calc): 1176.3547 Variable modifications: M3 : Oxidation ( M) Ions Score: 11
Expect: 0.64 Matches ( Bold Red ): 3/100 fragment ions using 8 most intense peaks

SEQUENCE LISTING

```
<160> NUMBER OF SEQ ID NOS: 31

<210> SEQ ID NO 1
<211> LENGTH: 11
<212> TYPE: PRT
<213> ORGANISM: Homo sapiens

<400> SEQUENCE: 1

Arg Ala Ser Gln Asp Ile Ser Asn Tyr Leu Ala
1               5                   10


<210> SEQ ID NO 2
<211> LENGTH: 7
<212> TYPE: PRT
<213> ORGANISM: Homo sapiens

<400> SEQUENCE: 2

Ala Ala Ser Ser Leu His Ser
1               5


<210> SEQ ID NO 3
<211> LENGTH: 9
<212> TYPE: PRT
<213> ORGANISM: Homo sapiens

<400> SEQUENCE: 3

Leu Gln Tyr Ser Thr Tyr Pro Ile Thr
1               5


<210> SEQ ID NO 4
<211> LENGTH: 5
<212> TYPE: PRT
<213> ORGANISM: Homo sapiens

<400> SEQUENCE: 4
```

```
Asn Tyr Ala Met Ser
1               5


<210> SEQ ID NO 5
<211> LENGTH: 17
<212> TYPE: PRT
<213> ORGANISM: Homo sapiens

<400> SEQUENCE: 5

Ala Ile Thr Pro Ser Gly Gly Ser Thr Asn Tyr Ala Asp Ser Val Lys
1               5                   10                  15

Gly


<210> SEQ ID NO 6
<211> LENGTH: 11
<212> TYPE: PRT
<213> ORGANISM: Homo sapiens

<400> SEQUENCE: 6

Val Pro Tyr Arg Ser Thr Trp Tyr Pro Leu Tyr
1               5                   10


<210> SEQ ID NO 7
<211> LENGTH: 108
<212> TYPE: PRT
<213> ORGANISM: Homo sapiens

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Ala Trp Phe Gln Arg Lys Pro Gly Lys Ala Pro Lys Ser Leu Ile
        35                  40                  45

Tyr Ala Ala Ser Ser Leu His Ser Lys Val Pro Thr Gln Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Ser Thr Tyr Pro Ile
                85                  90                  95

Thr Phe Gly Gly Gly Thr Lys Val Glu Ile Lys Arg
            100                 105


<210> SEQ ID NO 8
<211> LENGTH: 324
<212> TYPE: DNA
<213> ORGANISM: Homo sapiens

<400> SEQUENCE: 8

gacatccaga tgacccagtc tccatcctca ctgtctgcat ctgtaggaga cagagtcacc      60

atcacttgtc gggcgagtca ggacattagt aattatttag cctggtttca gcggaaacca     120

gggaaagccc ctaagtccct gatctatgct gcatccagtt tgcacagtaa ggtcccaaca     180

caattcagcg gcagtggatc tgggacagat ttcactctca ccatcagcag cctgcagcct     240

gaagattttg caacttatta ctgcctacag tatagtactt accctatcac cttcggcgga     300

gggaccaagg tggagatcaa acga                                            324


<210> SEQ ID NO 9
<211> LENGTH: 120
<212> TYPE: PRT
```

```
<213> ORGANISM: Homo sapiens

<400> SEQUENCE: 9

Glu Val Gln Leu Leu Glu Ser Gly Gly Asp Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Ala Ile Thr Pro Ser Gly Gly Ser Thr Asn Tyr Ala Asp Ser Val
    50                  55                  60

Lys Gly Arg Phe Thr Ile Ser Arg Asp Asn Ser Gln Asn Thr Leu Tyr
65                  70                  75                  80

Leu Gln Met Asn Ser Leu Arg Val Glu Asp Thr Ala Val Tyr Tyr Cys
                85                  90                  95

Gly Arg Val Pro Tyr Arg Ser Thr Trp Tyr Pro Leu Tyr Trp Gly Gln
            100                 105                 110

Gly Thr Leu Val Thr Val Ser Ser
        115                 120


<210> SEQ ID NO 10
<211> LENGTH: 360
<212> TYPE: DNA
<213> ORGANISM: Homo sapiens

<400> SEQUENCE: 10

gaggtgcagc tgttggagtc tggggggagac ttggtacagc ctggggggtc gctgagactc     60

tcctgtgcag cctctggatt caccttcagc aactatgcca tgagctgggt ccgccaggct    120

ccagggaagg ggctggagtg ggtctcagcg attactccta gtggtggtag tacaaattat    180

gcagactccg tgaagggccg gttcaccatc tccagagaca attcccagaa tacactgtat    240

ctgcaaatga acagcctgag agtcgaggac acggccgtat attactgtgg gagagtccca    300

tatagaagca cttggtaccc tttatattgg ggccagggaa ccctggtcac cgtctcctca    360


<210> SEQ ID NO 11
<211> LENGTH: 477
<212> TYPE: PRT
<213> ORGANISM: Homo sapiens

<400> SEQUENCE: 11

Met Thr Pro Glu Asp Pro Ser Glu Thr Glu Pro Ala Ala Pro Arg Pro
1               5                   10                  15

Gly Ala Ser Ala Pro Arg Gly Arg Arg Val Phe Leu Ala Ala Phe Ala
            20                  25                  30

Ala Ala Leu Gly Pro Leu Ser Phe Gly Phe Ala Leu Gly Tyr Ser Ser
        35                  40                  45

Pro Ala Ile Pro Ser Leu Gln Arg Ala Ala Pro Pro Ala Pro Arg Leu
    50                  55                  60

Asp Asp Ala Ala Ala Ser Trp Phe Gly Ala Val Val Thr Leu Gly Ala
65                  70                  75                  80

Ala Ala Gly Gly Val Leu Gly Gly Trp Leu Val Asp Arg Ala Gly Arg
                85                  90                  95

Lys Leu Ser Leu Leu Leu Cys Ser Val Pro Phe Val Ala Gly Phe Ala
            100                 105                 110

Val Ile Thr Ala Ala Gln Asp Val Trp Met Leu Leu Gly Gly Arg Leu
        115                 120                 125
```

```
Leu Thr Gly Leu Ala Cys Gly Val Ala Ser Leu Val Ala Pro Val Tyr
    130                 135                 140

Ile Ser Glu Ile Ala Tyr Pro Ala Val Arg Gly Leu Leu Gly Ser Cys
145                 150                 155                 160

Val Gln Leu Met Val Val Val Gly Ile Leu Leu Ala Tyr Leu Ala Gly
                165                 170                 175

Trp Val Leu Glu Trp Arg Trp Leu Ala Val Leu Gly Cys Val Pro Pro
            180                 185                 190

Ser Leu Met Leu Leu Leu Met Cys Phe Met Pro Glu Thr Pro Arg Phe
        195                 200                 205

Leu Leu Thr Gln His Arg Arg Gln Glu Ala Met Ala Ala Leu Arg Phe
    210                 215                 220

Leu Trp Gly Ser Glu Gln Gly Trp Glu Asp Pro Pro Ile Gly Ala Glu
225                 230                 235                 240

Gln Ser Phe His Leu Ala Leu Leu Arg Gln Pro Gly Ile Tyr Lys Pro
                245                 250                 255

Phe Ile Ile Gly Val Ser Leu Met Ala Phe Gln Gln Leu Ser Gly Val
            260                 265                 270

Asn Ala Val Met Phe Tyr Ala Glu Thr Ile Phe Glu Glu Ala Lys Phe
        275                 280                 285

Lys Asp Ser Ser Leu Ala Ser Val Val Val Gly Val Ile Gln Val Leu
    290                 295                 300

Phe Thr Ala Val Ala Ala Leu Ile Met Asp Arg Ala Gly Arg Arg Leu
305                 310                 315                 320

Leu Leu Val Leu Ser Gly Val Val Met Val Phe Ser Thr Ser Ala Phe
                325                 330                 335

Gly Ala Tyr Phe Lys Leu Thr Gln Gly Gly Pro Gly Asn Ser Ser His
            340                 345                 350

Val Ala Ile Ser Ala Pro Val Ser Ala Gln Pro Val Asp Ala Ser Val
        355                 360                 365

Gly Leu Ala Trp Leu Ala Val Gly Asn Met Cys Leu Phe Ile Ala Gly
    370                 375                 380

Phe Ala Val Gly Trp Gly Pro Ile Pro Trp Leu Leu Met Ser Glu Ile
385                 390                 395                 400

Phe Pro Leu His Val Lys Gly Val Ala Thr Gly Ile Cys Val Leu Thr
                405                 410                 415

Asn Trp Leu Met Ala Phe Leu Val Thr Lys Glu Phe Ser Ser Leu Met
            420                 425                 430

Glu Val Leu Arg Pro Tyr Gly Ala Phe Trp Leu Ala Ser Ala Phe Cys
        435                 440                 445

Ile Phe Ser Val Leu Phe Thr Leu Phe Cys Val Pro Glu Ile Lys Gly
    450                 455                 460

Lys Thr Leu Glu Gln Ile Thr Ala His Phe Glu Gly Arg
465                 470                 475


<210> SEQ ID NO 12
<211> LENGTH: 20
<212> TYPE: PRT
<213> ORGANISM: Homo sapiens

<400> SEQUENCE: 12

Pro Glu Asp Pro Ser Glu Thr Glu Pro Ala Ala Pro Arg Pro Gly Ala
1               5                   10                  15

Ser Ala Pro Arg
            20
```

<210> SEQ ID NO 13
<211> LENGTH: 10
<212> TYPE: PRT
<213> ORGANISM: Homo sapiens

<400> SEQUENCE: 13

```
Pro Ser Glu Thr Glu Pro Ala Ala Pro Arg
1               5                   10
```

<210> SEQ ID NO 14
<211> LENGTH: 33
<212> TYPE: PRT
<213> ORGANISM: Homo sapiens

<400> SEQUENCE: 14

```
Arg Val Phe Leu Ala Ala Phe Ala Ala Ala Leu Gly Pro Leu Ser Phe
1               5                   10                  15

Gly Phe Ala Leu Gly Tyr Ser Ser Pro Ala Ile Pro Ser Leu Gln Arg
            20                  25                  30

Ala
```

<210> SEQ ID NO 15
<211> LENGTH: 32
<212> TYPE: PRT
<213> ORGANISM: Homo sapiens

<400> SEQUENCE: 15

```
Arg Leu Asp Asp Ala Ala Ala Ser Trp Phe Gly Ala Val Val Thr Leu
1               5                   10                  15

Gly Ala Ala Ala Gly Gly Val Leu Gly Gly Trp Leu Val Asp Arg Ala
            20                  25                  30
```

<210> SEQ ID NO 16
<211> LENGTH: 10
<212> TYPE: PRT
<213> ORGANISM: Homo sapiens

<400> SEQUENCE: 16

```
Arg Gln Glu Ala Met Ala Ala Leu Arg Phe
1               5                   10
```

<210> SEQ ID NO 17
<211> LENGTH: 28
<212> TYPE: PRT
<213> ORGANISM: Homo sapiens

<400> SEQUENCE: 17

```
Arg Phe Leu Trp Gly Ser Glu Gln Gly Trp Glu Asp Pro Pro Ile Gly
1               5                   10                  15

Ala Glu Gln Ser Phe His Leu Ala Leu Leu Arg Gln
            20                  25
```

<210> SEQ ID NO 18
<211> LENGTH: 39
<212> TYPE: PRT
<213> ORGANISM: Homo sapiens

<400> SEQUENCE: 18

```
Lys Glu Phe Ser Ser Leu Met Glu Val Leu Arg Pro Tyr Gly Ala Phe
1               5                   10                  15

Trp Leu Ala Ser Ala Phe Cys Ile Phe Ser Val Leu Phe Thr Leu Phe
            20                  25                  30
```

Cys Val Pro Glu Ile Lys Gly
35

<210> SEQ ID NO 19
<211> LENGTH: 13
<212> TYPE: PRT
<213> ORGANISM: Homo sapiens

<400> SEQUENCE: 19

Lys Thr Leu Glu Gln Ile Thr Ala His Phe Glu Gly Arg
1 5 10

<210> SEQ ID NO 20
<211> LENGTH: 11
<212> TYPE: PRT
<213> ORGANISM: Homo sapiens

<400> SEQUENCE: 20

Ser Leu Ala Ser Val Val Val Gly Val Ile Gln
1 5 10

<210> SEQ ID NO 21
<211> LENGTH: 37
<212> TYPE: DNA
<213> ORGANISM: Artificial Sequence
<220> FEATURE:
<223> OTHER INFORMATION: Gamma primer

<400> SEQUENCE: 21
tctaaagaag cccctgggag cacagctcat caccatg 37

<210> SEQ ID NO 22
<211> LENGTH: 36
<212> TYPE: DNA
<213> ORGANISM: Artificial Sequence
<220> FEATURE:
<223> OTHER INFORMATION: Gamma primer

<400> SEQUENCE: 22
gcccggggag cgggggcttg ccggccgtcg cactca 36

<210> SEQ ID NO 23
<211> LENGTH: 33
<212> TYPE: DNA
<213> ORGANISM: Artificial Sequence
<220> FEATURE:
<223> OTHER INFORMATION: Gamma primer

<400> SEQUENCE: 23
accatgagtg agaaaaactg gatttgtgtg gca 33

<210> SEQ ID NO 24
<211> LENGTH: 30
<212> TYPE: DNA
<213> ORGANISM: Artificial Sequence
<220> FEATURE:
<223> OTHER INFORMATION: Gamma primer

<400> SEQUENCE: 24
ggagccggtg accagggttc cctggcccca 30

<210> SEQ ID NO 25
<211> LENGTH: 30
<212> TYPE: DNA
<213> ORGANISM: Artificial Sequence
<220> FEATURE:
<223> OTHER INFORMATION: Gamma primer

<400> SEQUENCE: 25
ctcaccatgg agtttgggct gagctgggtt 30

<210> SEQ ID NO 26
<211> LENGTH: 36
<212> TYPE: DNA
<213> ORGANISM: Artificial Sequence
<220> FEATURE:
<223> OTHER INFORMATION: Gamma primer

<400> SEQUENCE: 26
ggaggctgag gagacggtga ccagggttcc ctggcc 36

<210> SEQ ID NO 27
<211> LENGTH: 35
<212> TYPE: DNA
<213> ORGANISM: Artificial Sequence
<220> FEATURE:
<223> OTHER INFORMATION: Kappa primer

<400> SEQUENCE: 27
ggctcgagat ggacatgrrr dycchvgykc asctt 35

<210> SEQ ID NO 28
<211> LENGTH: 28
<212> TYPE: DNA
<213> ORGANISM: Artificial Sequence
<220> FEATURE:
<223> OTHER INFORMATION: Kappa primer

<400> SEQUENCE: 28
cccgtcgacc atcagatggc gggaagat 28

<210> SEQ ID NO 29
<211> LENGTH: 250
<212> TYPE: PRT
<213> ORGANISM: Homo sapiens

<400> SEQUENCE: 29

```
Tyr Asn Thr Val Ser Phe Asn Leu Gly Glu Ala Tyr Glu Tyr Pro Thr
1               5                   10                  15

Phe Ile Gln Asp Leu Arg Asn Glu Leu Ala Lys Gly Thr Pro Val Cys
            20                  25                  30

Gln Leu Pro Val Thr Leu Gln Thr Ile Ala Asp Asp Lys Arg Phe Val
        35                  40                  45

Leu Val Asp Ile Thr Thr Thr Ser Lys Lys Thr Val Lys Val Ala Ile
    50                  55                  60

Asp Val Thr Asp Val Tyr Val Val Gly Tyr Gln Asp Lys Trp Asp Gly
65                  70                  75                  80

Lys Asp Arg Ala Val Phe Leu Asp Lys Val Pro Thr Val Ala Thr Ser
                85                  90                  95

Lys Leu Phe Pro Gly Val Thr Asn Arg Val Thr Leu Thr Phe Asp Gly
            100                 105                 110

Ser Tyr Gln Lys Leu Val Asn Ala Ala Lys Ala Asp Arg Lys Ala Leu
        115                 120                 125

Glu Leu Gly Val Asn Lys Leu Glu Phe Ser Ile Glu Ala Ile His Gly
    130                 135                 140

Lys Thr Ile Asn Gly Gln Glu Ala Ala Lys Phe Phe Leu Ile Val Ile
145                 150                 155                 160

Gln Met Val Ser Glu Ala Ala Arg Phe Lys Tyr Ile Glu Thr Glu Val
```

-continued

```
                165                 170                 175

Val Asp Arg Gly Leu Tyr Gly Ser Phe Lys Pro Asn Phe Lys Val Leu
            180                 185                 190

Asn Leu Glu Asn Asn Trp Gly Asp Ile Ser Asp Ala Ile His Lys Ser
        195                 200                 205

Ser Pro Gln Cys Thr Thr Ile Asn Pro Ala Leu Gln Leu Ile Ser Pro
    210                 215                 220

Ser Asn Asp Pro Trp Val Val Asn Lys Val Ser Gln Ile Ser Pro Asp
225                 230                 235                 240

Met Gly Ile Leu Lys Phe Lys Ser Ser Lys
                245                 250


<210> SEQ ID NO 30
<211> LENGTH: 10
<212> TYPE: PRT
<213> ORGANISM: Homo sapiens

<400> SEQUENCE: 30

Pro Ser Glu Thr Glu Pro Ala Ala Pro Pro
1               5                   10


<210> SEQ ID NO 31
<211> LENGTH: 4
<212> TYPE: PRT
<213> ORGANISM: Homo sapiens

<400> SEQUENCE: 31

Arg Gly Tyr Trp
1
```

CANCER ASSOCIATED GLUCOSE TRANSPORTER 8 VARIANT

INCORPORATION OF SEQUENCE LISTING

A computer readable form of the Sequence Listing "10241-109_SequenceListing.txt" (14,270 bytes), submitted via EFS-WEB and created on Feb. 15, 2011, is herein incorporated by reference.

FIELD OF THE INVENTION

The invention relates to human cancer-specific binding proteins and all uses thereof. In particular, the invention relates to antibodies or antibody fragments specific for antigens or molecules on cancer cells and to immunoconjugates comprising the binding proteins of the invention, and methods of use thereof. The invention also relates to a novel cancer associated-antigen and uses thereof.

BACKGROUND OF THE INVENTION

In the year 2000, an estimated 22 million people were suffering from cancer worldwide and 6.2 millions deaths were attributed to this class of diseases. Every year, there are over 10 million new cases and this estimate is expected to grow by 50% over the next 15 years (WHO, World Cancer Report. Bernard W. Stewart and Paul Kleihues, eds. IARC Press, Lyon, 2003). Current cancer treatments are limited to invasive surgery, radiation therapy and chemotherapy, all of which cause either potentially severe side-effects, non-specific toxicity and/or traumatizing changes to ones body image and/or quality of life. Cancer can become refractory to chemotherapy reducing further treatment options and likelihood of success. The prognosis for some cancer is worse than for others and some are almost always fatal. In addition, some cancers with a relatively high treatment success rate remain major killers due to their high incidence rates.

One of the causes for the inadequacy of current cancer treatments is their lack of selectivity for affected tissues and cells. Surgical resection always involves the removal of apparently normal tissue as a "safety margin" which can increase morbidity and risk of complications. It also always removes some of the healthy tissue that may be interspersed with tumor cells and that could potentially maintain or restore the function of the affected organ or tissue. Radiation and chemotherapy will kill or damage many normal cells due to their non-specific mode of action. This can result in serious side-effects such as severe nausea, weight loss and reduced stamina, loss of hair etc., as well as increasing the risk of developing secondary cancer later in life. Treatment with greater selectivity for cancer cells would leave normal cells unharmed thus improving outcome, side-effect profile and quality of life.

The selectivity of cancer treatment can be improved by using antibodies that are specific for molecules present only or mostly on cancer cells. Such antibodies can be used to modulate the immune system and enhance the recognition and destruction of the cancer by the patient's own immune system. They can also block or alter the function of the target molecule and, thus, of the cancer cells. They can also be used to target drugs, genes, toxins or other medically relevant molecules to the cancer cells. Such antibody-drug complexes are usually referred to as immunotoxins or immunoconjugates and a number of such compounds have been tested in recent year [Kreitman R J (1999) Immunotoxins in cancer therapy. Curr Opin Immunol 11:570-578; Kreitman R J (2000) Immunotoxins. Expert Opin Pharmacother 1:1117-1129; Wahl R L (1994) Experimental radioimmunotherapy. A brief overview. Cancer 73:989-992; Grossbard M L, Fidias P (1995) Prospects for immunotoxin therapy of non-Hodgkin's lymphoma. Clin Immunol Immunopathol 76:107-114; Jurcic J G, Caron P C, Scheinberg D A (1995) Monoclonal antibody therapy of leukemia and lymphoma. Adv Pharmacol 33:287-314; Lewis J P, DeNardo G L, DeNardo S J (1995) Radioimmunotherapy of lymphoma: a UC Davis experience. Hybridoma 14:115-120; Uckun F M, Reaman G H (1995) Immunotoxins for treatment of leukemia and lymphoma. Leuk Lymphoma 18:195-201; Kreitman R J, Wilson W H, Bergeron K, Raggio M, Stetler-Stevenson M, FitzGerald D J, Pastan I (2001) Efficacy of the anti-CD22 recombinant immunotoxin BL22 in chemotherapy-resistant hairy-cell leukemia. N Engl J Med 345:241-247]. Most antibodies tested to date have been raised against known cancer markers in the form of mouse monoclonal antibodies, sometimes "humanized" through molecular engineering. Unfortunately, their targets are usually also present on subset of normal cells thus still causing some non-specific effect. Furthermore, these antibodies are basically mouse proteins that are being seen by the human patient's immune system as foreign proteins. The ensuing immune reaction and antibody response can result in a loss of efficacy or in side-effects.

The inventors have used a different approach in their development of antibodies for cancer treatment. Instead of immunizing experimental animals with cancer cells or isolated cancer cell markers, they have sought out only those markers that are recognized by the patient's own immune system or, in other words, that are seen by the immune system as a foreign molecule. This implies that the markers or antigens are usually substantially absent on normal cells and, thus, the risk of non-specific toxicity is further reduced. Hybridoma libraries are generated from cancer patient-derived lymphocytes and the antibodies they secrete are tested for binding to normal and tumor cells. Only antibodies showing high selectivity for cancer cells are retained for further evaluation and development as a cancer therapeutic or diagnostic agent. One such highly selective antibody is the subject of this patent application. In addition to being selective, this antibody is fully compatible with the patient's immune system by virtue of being a fully human protein. The antibody of the invention can be used for diagnostic or therapeutic uses or as a basis for engineering other binding molecules for the target antigen. The antibody of the invention can also be used to identify the target antigen. The antigen can then be used to design new cancer treatment or diagnostics.

The basic structure of an antibody molecule consists of four protein chains, two heavy chains and two light chains. These chains are inter-connected by disulfide bonds. Each light chain is comprised of a light chain variable region and a light chain constant region. Each heavy chain is comprised of a heavy chain variable region and a heavy chain constant region. The light chain and heavy chain variable regions can be further subdivided into framework regions and regions of hypervariability, termed complementarity determining regions (CDR). Each light chain and heavy chain variable region is composed of three CDRs and four framework regions.

Glucose transporter 8 (GLUT8) is a member of the GLUT family of proteins and is known to have sugar transporting activity. GLUT8 is encoded by gene slc2a8, which is found on human chromosome 9. GLUT8 is 477 amino acids in length. It is a ~50 kDa type II transmembrane protein. It has 12 transmembrane regions. It has a short extracellular loop between TM1 and TM2 and a long extracellular loop between TM9 and TM10. Despite having several transmembrane regions, GLUT8 is located intracellularly likely because of a N-terminal di-leucine motif (Ibberson et al. JBC 275: 4607-4612, 2000; Moadel et al., Cancer Res 65:698-702, 2005). Translocation to the membrane has been observed in mouse cells upon insulin treatment (Carayannopoulos et al., PNAS 97:7313-18, 2000) or in rat cells upon hypoxic shock or insulin treatment (U.S. Ser. No. 09/886,954 [2002/0038464]). In human, membrane localization has not been reported and no stimuli has been identified to induce translocation (Widmer et al., Endocrinology 146:4727-36, 2005).

GLUT/SLC2A family nomenclature has been published in: Amer. J. Physiol. Endocrinol. Metab. 282:E974-76, 2002. The name GLUT8 was used in the past to describe what it now known as GLUT12—as indicated in that paper. The N-terminal di-leucine motif has been found in all mammalian GLUT8 sequences (see Zhao et al., Biochimica et Biophysica Acta 1680:103-113, 2004—showing bovine, human, rat, mouse).

SUMMARY OF THE INVENTION

The present inventors have prepared human cancer-specific antibodies that bind to several types of cancer cells, including breast cancer, ovarian cancer, prostate cancer, melanoma, liver cancer, colon cancer, cervical cancer, head & neck cancer, bladder cancer, stomach cancer, pancreatic cancer and endometrial cancer. Importantly, the antibodies do not significantly bind to normal tissue making them suitable candidates for cancer therapy and diagnosis.

The inventors have cloned and sequenced the antibodies and determined the sequence of the antibody light and heavy chain variable regions and complementarity determining regions 1, 2 and 3. Accordingly, the invention provides isolated light chain complementarity determining regions 1, 2 and/or 3, comprising the amino acid sequences RASQDISNYLA (SEQ ID NO:1), AASSLHS (SEQ ID NO:2) and LQYSTYPIT (SEQ ID NO:3), respectively; and isolated heavy chain complementarity determining regions 1, 2 and 3, comprising the amino acid sequences NYAMS (SEQ ID NO:4), AITPSGGSTNYADSVKG (SEQ ID NO:5) and VPYRSTWYPLY (SEQ ID NO:6), respectively.

The invention also provides isolated nucleic acid sequences encoding light chain complementarity determining regions 1, 2 and/or 3, comprising the amino acid sequences RASQDISNYLA (SEQ ID NO:1), AASSLHS (SEQ ID NO:2) and LQYSTYPIT (SEQ ID NO:3), respectively; and isolated nucleic acid sequences encoding heavy chain complementarity determining regions 1, 2 and/or 3, comprising the amino acid sequences NYAMS (SEQ ID NO:4), AITPSGGSTNYADSVKG (SEQ ID NO:5) and VPYRSTWYPLY (SEQ ID NO:6), respectively.

Additional aspects of the invention are isolated light chain variable regions comprising light chain complementarity determining regions 1, 2 and/or 3 of the invention (SEQ ID NOS:1-3), and isolated heavy chain variable regions comprising heavy chain complementarity determining regions 1, 2 and/or 3 of the invention (SEQ ID NOS:4-6). In one embodiment, the light chain variable region comprises the amino acid sequence shown in FIG. 1 (SEQ ID NO:7). In another embodiment, the heavy chain variable region comprises the amino acid sequence shown in FIG. 2 (SEQ ID NO:9).

The invention also provides an isolated nucleic acid sequence encoding the light chain variable region of the invention, and an isolated nucleic acid sequence encoding the heavy chain variable region of the invention. In one embodiment, the light chain variable region comprises the nucleic acid sequence shown in FIG. 1 (SEQ ID NO: 8). In another embodiment, the heavy chain variable region comprises the nucleic acid sequence shown in FIG. 2 (SEQ ID NO:10).

Another aspect of the invention is a binding protein, preferably an antibody or antibody fragment, that comprises at least one light chain complementarity determining region of the invention (i.e. one or more of the SEQ ID NOS:1-3) and/or at least one heavy chain complementarity determining region of the invention (i.e. one or more of SEQ ID NO:4-6). The invention also provides a binding protein, preferably an antibody or antibody fragment that comprises the light chain variable regions of the invention and/or the heavy chain variable regions of the invention.

The inventors have also identified the antigen to which the binding proteins of the invention bind. Accordingly, the invention provides binding proteins that bind to: glucose transporter 8 (GLUT8) or variants thereof; a protein comprising any one of the amino acid sequences of SEQ ID NOS:11-20, preferably SEQ ID NOS:11-13; or a cancer-associated variant of GLUT8 that is expressed on the surface of cancer cells. In one embodiment of the invention, the cancer-associated variant of GLUT8, comprises the amino acid sequence defined by any one of SEQ ID NOS: 11, 12 or 13, or variants thereof. In another embodiment of the invention, the cancer-associated variant of GLUT8, comprises GLUT8 that has a modification in the N-terminal di-leucine motif. In a further embodiment of the invention, the N-terminal di-leucine motif has been modified to di-alanine.

In addition, the invention provides compositions comprising the binding proteins of the invention, such as antibodies and antibody fragments, with a pharmaceutically acceptable excipient, carrier, buffer or stabilizer.

Another aspect of the invention is an immunoconjugate comprising (1) binding protein of the invention, preferably an antibody or antibody fragment that binds to an antigen or molecule on a cancer cell, attached to (2) an effector molecule. A further aspect of the invention is an immunoconjugate comprising (1) binding protein of the invention, preferably an antibody or antibody fragment that binds to an antigen or molecule that is internalized by a cancer cell, attached to (2) an effector molecule. In a preferred embodiment, the effector molecule is (i) a label, which can generate a detectable signal, directly or indirectly, or (ii) a cancer therapeutic agent, which is either cytotoxic, cytostatic or otherwise prevents or reduces the ability of the cancer cells to divide and/or metastasize. Preferably, the cancer therapeutic agent is a toxin or cytotoxin.

The invention also provides compositions comprising the immunoconjugate of the invention and uses of the immunoconjugate for the manufacture of a medicament for treating or preventing cancer, and diagnostic purposes. In addition, the invention provides methods of treating or preventing cancer using the immunoconjugate of the invention and related kits.

A further aspect of the invention is a method of detecting or monitoring cancer in a subject comprising the steps of:

(1) contacting a test sample taken from said subject with a binding protein of the invention and that binds specifically to an antigen on the cancer cell to produce a binding protein-antigen complex;

(2) measuring the amount of binding protein-antigen complex in the test sample; and (3) comparing the amount of binding protein-antigen complex in the test sample to a control.

Another aspect of the invention is a diagnostic agent comprising the immunoconjugate of the invention, wherein the effector molecule is a label, which can generate a detectable signal, directly or indirectly.

The invention also includes an isolated protein that can specifically bind with one of the binding proteins of the invention, nucleic acid sequences and uses thereof.

The inventors have identified the antigen to which the binding proteins of the invention bind. The invention includes the novel-cancer associated antigen, which is a variant of GLUT8 that is expressed on the surface of cancer cells. The invention also includes the use of the novel cancer-associated antigen of the invention in the treatment and diagnosis of cancer.

In an embodiment of the invention, the cancer-associated variant of GLUT8, comprises the amino acid sequence defined by any one of SEQ ID NOS: 11, 12 or 13, or variants thereof. In another embodiment of the invention, the cancer-associated variant of GLUT8, comprises GLUT8 that has a modification in the N-terminal di-leucine motif. In a further embodiment of the invention, the N-terminal di-leucine motif has been modified to di-alanine.

The invention also includes methods of detecting or monitoring cancer in a subject having or suspected of having cancer, comprising detecting a cancer-associated variant of GLUT8 on a cell in the sample, wherein cancer is indicated, if the cancer-associated variant of GLUT8 is detected on the cell.

In addition, the invention includes methods of detecting or monitoring cancer in a subject having or suspected of having cancer, comprising detecting the expression of a cancer-associated variant of GLUT8 in the cell in the sample, wherein cancer is indicated, if the expression of the cancer-associated variant of GLUT8 is detected in the cell.

A further aspect of the invention is a method of treating or preventing cancer in a subject by modulating the function or expression of GLUT8 in the cancer cell.

The invention also includes methods of treating or preventing cancer in a subject using the cancer-associated variant of GLUT8 or fragments thereof. In addition, the invention includes pharmaceutical compositions comprising an effective amount a cancer-associated variant of GLUT8 or fragments thereof, nucleic acid sequences encoding the cancer-associated variant of GLUT8 or fragments thereof, and/or recombinant expression vectors comprising nucleic acid sequences encoding the cancer-associated variant of GLUT8 or fragments thereof.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which:

FIG. 1 is the nucleic acid (SEQ ID NO:8) and amino acid (SEQ ID NO:7) sequence of the light chain variable region of VB1-050.

FIG. 2 is the nucleic acid (SEQ ID NO:10) and amino acid (SEQ ID NO:9) sequence of the heavy chain variable region of VB1-050.

Fold Increase was calculated using the following formula, MF Fold increase=MF measured at each concentration/MF measured with PBS.

Figure 9:
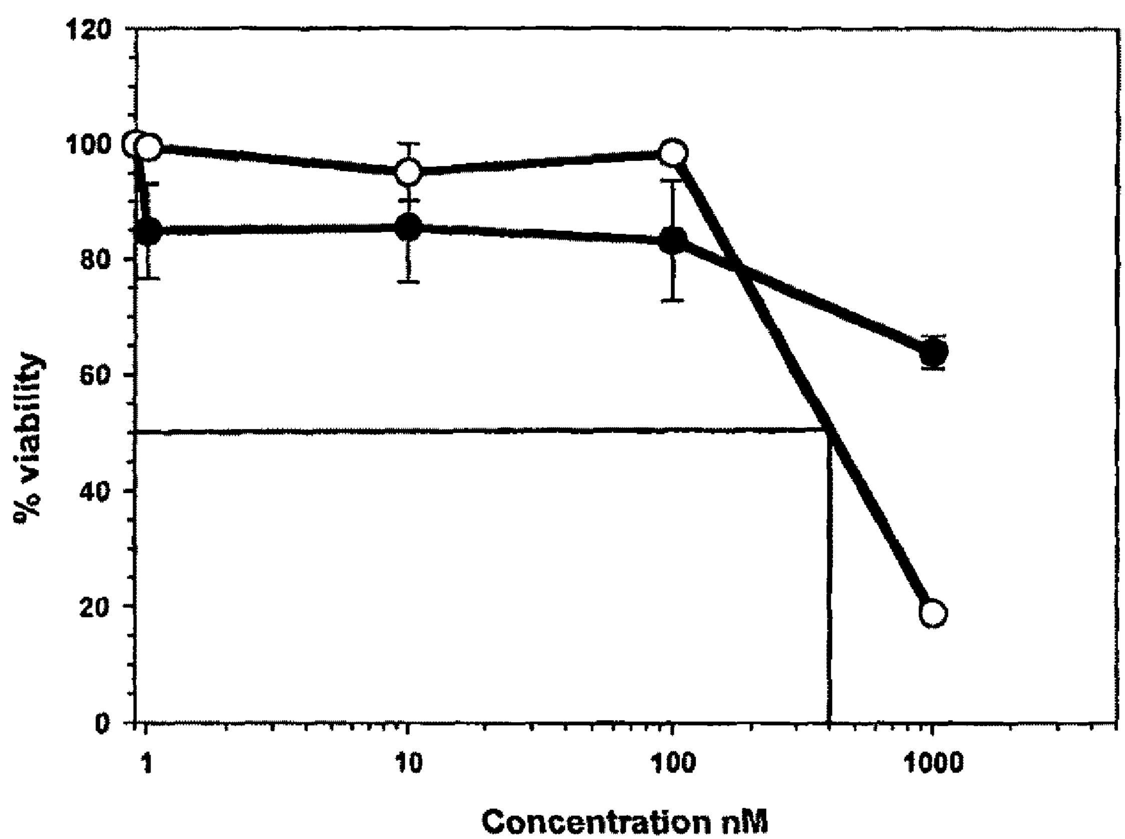

FIG. 9 shows the in vitro cytotoxicity of VB6-050. MTS assay of VB6-050 with antigen-positive cells MB-435S (open circle) and antigen-negative cells Daudi (black circle). Cells seeded at 1000 cells per well, were incubated with the Fab-de-bouganin purified proteins. After 5 days incubation, the cell viability was measured and $IC_{50}$ was determined.

Figure 10:
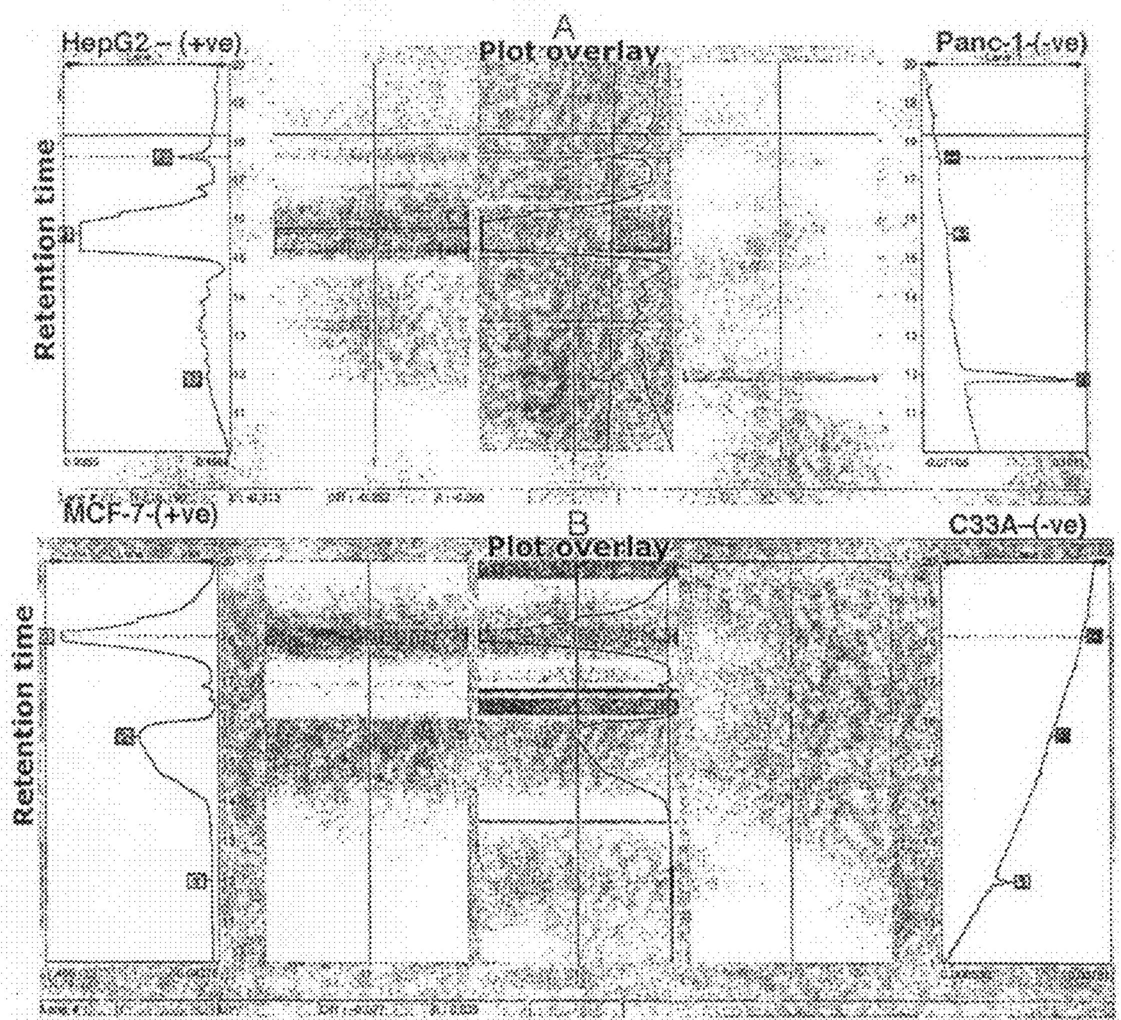

FIG. 10 shows the fractionation profiles of HepG2, MCF-7, Panc-1 and C-33A on a PF-2D system. A comparative profile of the differences in antigen expression between two positive and two negative cell lines. This figure represents a chromatographic file from 10 to 25 minutes. A clear view of the separated antigen differences is visualized in both positive cell lines. MCF-7 and HepG2 showed two peaks eluting at 15 and 18 minutes, indicating moderate levels of hydrophobicity. Panc-1 and C-33A showed no corresponding peaks. A peak at 12 minutes was observed in all cell lines.

FIG. 11 shows the TOF-MS scans of peptides obtained from HepG2 cell line, to detect the presence of all peptide ions in the sample. Fifty-three scans at 1200-1400V in the range of 100-1200 amu on a static nanospray resulted in the recovery of a significant number of peptides, which when analyzed yielded a protein ID as Glucose Transporter 8.

FIG. 12 shows the TOF-MS scans of peptides obtained from Panc-1 cell line, to detect the presence of all peptide ions in the sample. Thirty scans at 1200-1400V in the range of 100-1200 amu on a static nanospray resulted in the recovery of a significant number of peptides, which when analyzed yielded a protein ID as IgG.

FIG. 13 shows the TOF-MS scans of peptides obtained from MCF-7 cell line, to detect the presence of all peptide ions in the sample. Twenty-seven scans at 1200-1400V in the range of 100-1200 amu on a static nanospray resulted in the recovery of a significant number of peptides, which when analyzed yielded a protein ID as Glucose Transporter 8.

FIG. 14 shows the TOF-MS scans of peptides obtained from C-33A cell line, to detect the presence of all peptide ions in the sample. Thirty scans at 1200-1400V in the range of 100-1200 amu on a static nanospray resulted in the recovery of a significant number of peptides, which when analyzed yielded a protein ID as IgG.

FIG. 15 shows the sequence coverage of peptides recovered from mass spectrometry analysis as listed in Table 8. A total of 8 peptides were recovered from in-solution tryptic digestion and 34% coverage of the protein was obtained. Sequences underlined represent the peptide sequences recovered and bolded sequences show the variant amino acid sequences.

FIG. 16 shows the peptide mass fingerprinting results for the peptides recovered from VB1-050Ag. Protein scores greater than 64 were considered significant. The only significant protein IDs observed pointed to the one antigen, known as Glucose Transporter 8.

FIG. 17 shows that the identified antigen, glucose transporter 8, has a significant score of 83. Due to the nature of the database server and the similarity/homology linked proteins, all the isoforms of this protein were pulled down as hits. MS/MS fragmentation and identity of peptides confirms that the antigen is glucose transporter 8.

FIG. 18 shows the MS/MS ion fragmentation of the neutral peptide Mr. 1401.54, appearing as a triply charged molecule (466.60000, 3+). The peptide sequence (SEQ ID NO:19) exactly matched the peptide from Glucose Transporter 8.

Figure 19:
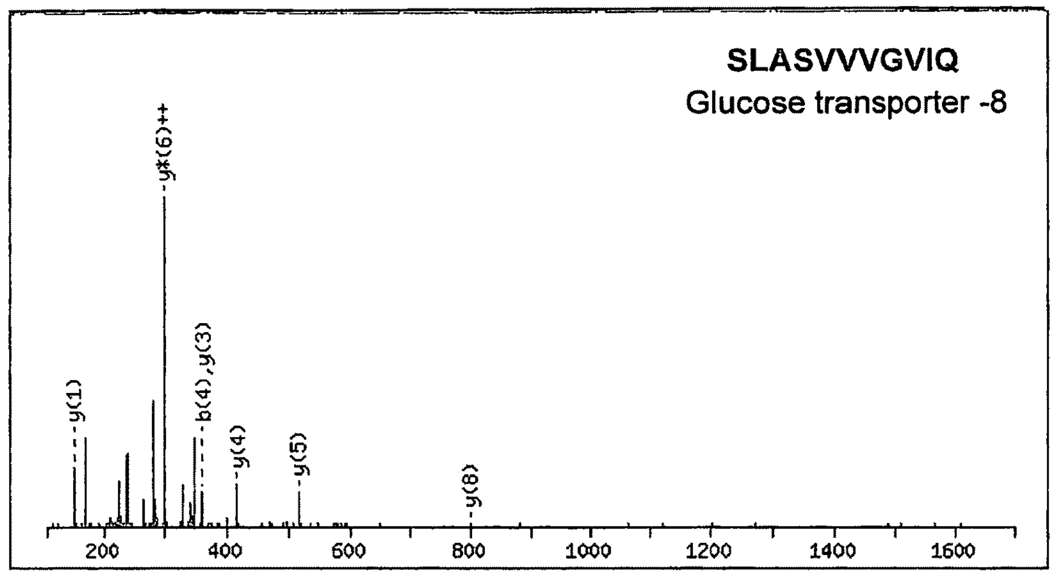

FIG. 19 shows the MS/MS ion fragmentation of the neutral peptide Mr. 1070.785, appearing as a doubly charged molecule (536.40000, 2+). The peptide sequence (SEQ ID NO:20) exactly matched the peptide from Glucose Transporter 8.

Figure 20:
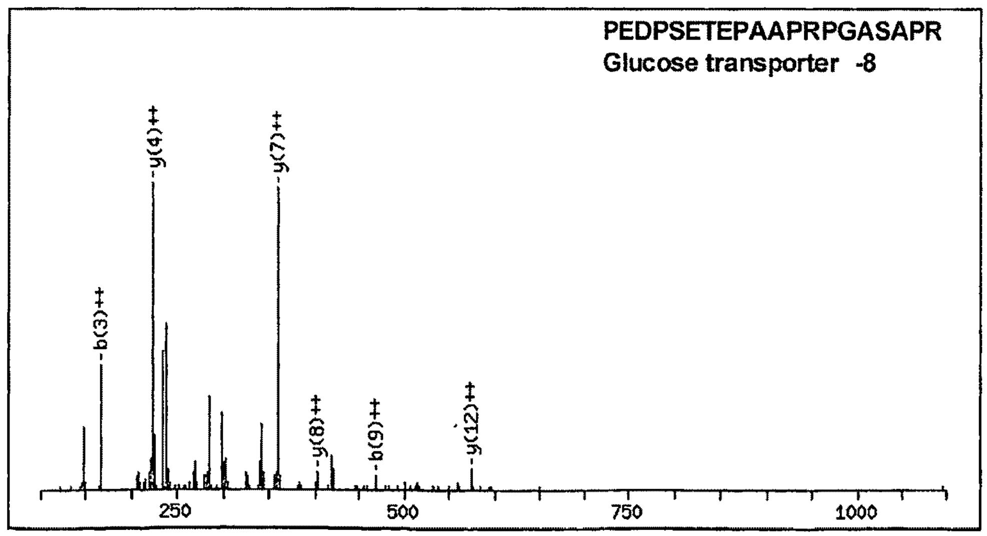

FIG. 20 shows the MS/MS ion fragmentation of the neutral peptide Mr. 1997.9992, appearing as a triply charged molecule (667.098230, 3+). The peptide sequence (SEQ ID NO:12) showed changes in amino acids at positions 7, 10, 12, 13, 14, 15 and 18; compared to the homologous peptide from Glucose Transporter 8.

Figure 21:
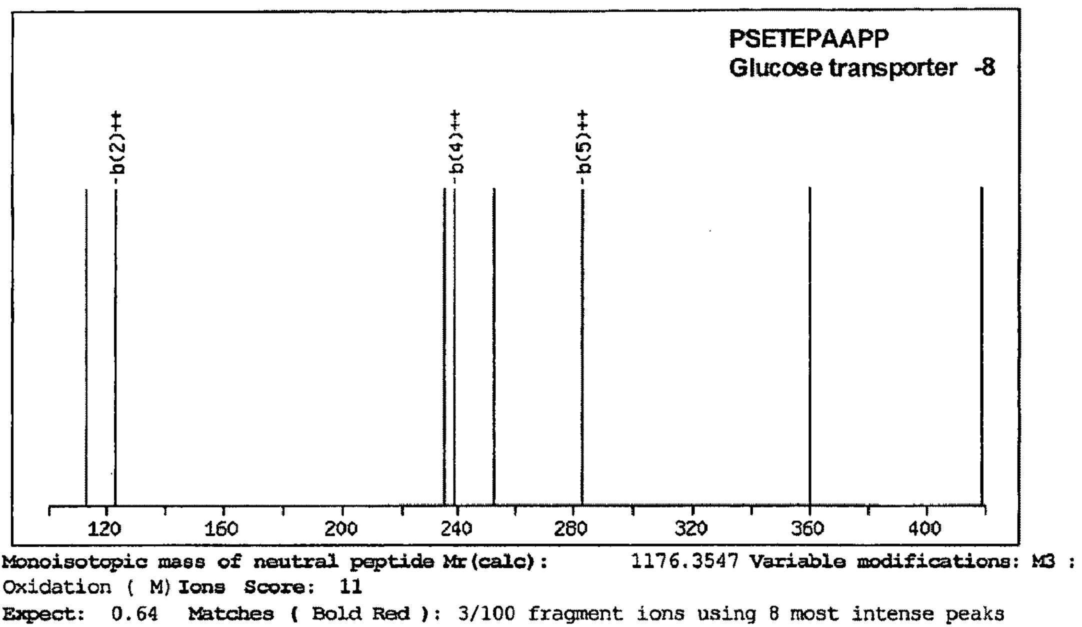

FIG. 21 shows the MS/MS ion fragmentation of the neutral peptide Mr. 1176.3547, appearing as a doubly charged molecule (589.100000, 2+). The peptide sequence (SEQ ID NO:30) showed changes in amino acids at positions 7, 10, 12, 13, 14 and 15; compared to the homologous peptide from Glucose Transporter 8.

DETAILED DESCRIPTION OF THE INVENTION

(A) Definitions

The term "administered systemically" as used herein means that the immunoconjugate and/or other cancer therapeutic may be administered systemically in a convenient manner such as by injection (subcutaneous, intravenous, intramuscular, etc.), oral administration, inhalation, transdermal administration or topical application (such as topical cream or ointment, etc.), suppository applications, or means of an implant. An implant can be of a porous, non-porous, or gelatinous material, including membranes, such as sialastic membranes, or fibers. Suppositories generally contain active ingredients in the range of 0.5% to 10% by weight.

The term "amino acid" includes all of the naturally occurring amino acids as well as modified amino acids.

The term "antibody" as used herein is intended to include monoclonal antibodies, polyclonal antibodies, and chimeric antibodies. The antibody may be from recombinant sources and/or produced in transgenic animals. The term "antibody fragment" as used herein is intended to include Fab, Fab', $F(ab')_2$, scFv, dsFv, ds-scFv, dimers, minibodies, diabodies, and multimers thereof and bispecific antibody fragments. Antibodies can be fragmented using conventional techniques. For example, $F(ab')_2$ fragments can be generated by treating the antibody with pepsin. The resulting $F(ab')_2$ fragment can be treated to reduce disulfide bridges to produce Fab' fragments. Papain digestion can lead to the formation of Fab fragments. Fab, Fab' and $F(ab')_2$, scFv, dsFv, ds-scFv, dimers, minibodies, diabodies, bispecific antibody fragments and other fragments can also be synthesized by recombinant techniques.

The term "antibody or antibody fragment of the invention" as used herein comprises at least one light chain complementarity determining region of the invention (i.e. one or more of SEQ ID NOS:1-3) and/or at least one heavy chain complementarity determining region of the invention (i.e. one or more of SEQ ID NOS:4-6). Preferably, the antibody or antibody fragment comprises the light chain CDR sequences (SEQ ID NOS:1-3) and/or the heavy chain CDR sequences (SEQ ID NOS:4-6) or functional variants of the sequences so that the antibody or antibody fragment can bind to the cancer cell without substantially binding to normal cells. Antibodies or antibody fragments of the invention also include antibodies or antibody fragments that bind to glucose transporter 8 (GLUT8) or variants thereof, or a protein comprising any one of the amino acid sequences of SEQ ID NOS: 11-20, preferably SEQ ID NOS:11-13.

By "at least moderately stringent hybridization conditions" it is meant that conditions are selected which promote selective hybridization between two complementary nucleic acid molecules in solution. Hybridization may occur to all or a portion of a nucleic acid sequence molecule. The hybridizing portion is typically at least 15 (e.g. 20, 25, 30, 40 or 50) nucleotides in length. Those skilled in the art will recognize that the stability of a nucleic acid duplex, or hybrids, is determined by the Tm, which in sodium containing buffers is a function of the sodium ion concentration and temperature (Tm=81.5° C.-16.6 (Log 10 [Na+])+0.41(%(G+C)−600/l), or similar equation). Accordingly, the parameters in the wash conditions that determine hybrid stability are sodium ion concentration and temperature. In order to identify molecules that are similar, but not identical, to a known nucleic acid molecule a 1% mismatch may be assumed to result in about a 1° C. decrease in Tm, for example if nucleic acid molecules are sought that have a >95% identity, the final wash temperature will be reduced by about 5° C. Based on these considerations those skilled in the art will be able to readily select appropriate hybridization conditions. In preferred embodiments, stringent hybridization conditions are selected. By way of example the following conditions may be employed to achieve stringent hybridization: hybridization at 5× sodium chloride/sodium citrate (SSC)/5×Denhardt's solution/1.0% SDS at Tm−5° C. based on the above equation, followed by a wash of 0.2×SSC/0.1% SDS at 60° C. Moderately stringent hybridization conditions include a washing step in 3×SSC at 42° C. It is understood, however, that equivalent stringencies may be achieved using alternative buffers, salts and temperatures. Additional guidance regarding hybridization conditions may be found in: Current Protocols in Molecular Biology, John Wiley & Sons, N.Y., 2002, and in: Sambrook et al., Molecular Cloning: a Laboratory Manual, Cold Spring Harbor Laboratory Press, 2001.

The term "binding protein" as used herein refers to proteins that specifically bind to another substance. In an embodiment, binding proteins are antibodies or antibody fragments.

The term "binding proteins of the invention" as used herein includes antibodies or antibody fragments of the invention.

By "biologically compatible form suitable for administration in vivo" is meant a form of the substance to be administered in which any toxic effects are outweighed by the therapeutic effects.

The term "cancer" as used herein includes any cancer that can be bound by a binding protein of the invention, preferably an antibody or antibody fragment of the invention.

The term "cancer-associated variant of glucose transporter 8" as used herein refers to a novel variant of glucose transporter 8 that is expressed on the surface of cancer cells. In one embodiment of the invention a cancer-associated variant of GLUT8 has the same function as GLUT8 as a transporter of sugar, but a different localization in the cell. For example, the cancer-associated variant of GLUT8 as the same function as GLUT8, as a transporter of sugar, but is localized to the surface of the cell. In another embodiment, the cancer-associated variant of glucose transporter 8 is a protein comprising the amino acid sequence defined by SEQ ID NO: 11. In an additional embodiment, the cancer-associated variant of glucose transporter 8 is a protein comprising the amino acid sequence defined by SEQ ID NO:12. In a further embodiment, the cancer-associated variant of glucose transporter 8 is a protein comprising the amino acid sequence defined by SEQ ID NO:13. In another embodiment of the invention, the cancer-associated variant of GLUT8, comprises GLUT8 that has a modification in the N-terminal di-leucine motif. In a further embodiment of the invention, the N-terminal di-leucine motif has been modified to di-alanine.

A "conservative amino acid substitution", as used herein, is one in which one amino acid residue is replaced with another amino acid residue without abolishing the protein's desired properties.

A control can be used in the method. The term "control" as used herein refers to a sample from a subject or a group of subjects who are either known as having cancer or not having cancer.

The term "controlled release system" as used means the immunoconjugate and/or other cancer therapeutic of the invention can be administered in a controlled fashion. For example, a micropump may deliver controlled doses directly into the area of the tumor, thereby finely regulating the timing and concentration of the pharmaceutical composition (see, e.g., Goodson, 1984, in Medical Applications of Controlled Release, vol. 2, pp. 115-138).

The term "derivative of a peptide" refers to a peptide having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as derivatives are those peptides which contain one or more naturally occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine.

The phrase "detecting or monitoring cancer" refers to a method or process of determining if a subject has or does not have cancer or the extent of cancer. In addition, the binding proteins of the invention can be used to detect or monitor the appearance and progression of the disease.

The term "direct administration" as used herein means the immunoconjugate and/or other cancer therapeutic may be administered, without limitation, intratumorally, intravascularly, and peritumorally. For example, the immunoconjugate may be administered by one or more direct injections into the tumor, by continuous or discontinuous perfusion into the tumor, by introduction of a reservoir of the immunoconjugate, by introduction of a slow-release apparatus into the tumor, by introduction of a slow-release formulation into the tumor, and/or by direct application onto the tumor. By the mode of administration "into the tumor," introduction of the immunoconjugate and/or other cancer therapeutic to the area of the tumor, or into a blood vessel or lymphatic vessel that substantially directly flows into the area of the tumor, is included.

As used herein, the phrase "effective amount" means an amount effective, at dosages and for periods of time necessary to achieve the desired result. Effective amounts of an immunoconjugate may vary according to factors such as the disease state, age, sex, weight of the animal. Dosage regime may be adjusted to provide the optimum therapeutic response. For example, several divided doses may be administered daily or the dose may be proportionally reduced as indicated by the exigencies of the therapeutic situation.

"Glucose transporter 8" (GLUT8) is a protein encoded by gene slc2a8, which is found on human chromosome 9. It is a member of class III of the GLUT family of proteins and is known to have sugar transporting activity. GLUT8 is 477 amino acids in length. It is a ~50 kDa type II transmembrane protein. It has 12 transmembrane regions. It has a short putative extracellular loop between TM1 and TM2 and a long extracellular loop between TM9 and TM10. The term includes variants of GLUT8. (GLUT/SLC2A family nomenclature: Amer. J. Physiol. Endocrinol. Metab. 282:E974-76, 2002.)

The term "heavy chain complementarity determining region" as used herein refers to regions of hypervariability within the heavy chain variable region of an antibody molecule. The heavy chain variable region has three complementarity determining regions termed heavy chain complementarity determining region 1, heavy chain complementarity determining region 2 and heavy chain complementarity determining region 3 from the amino terminus to carboxy terminus.

The term "heavy chain variable region" as used herein refers to the variable region of a heavy chain.

The term "immunoconjugate of the invention" is used herein comprises (1) a binding protein, preferably an antibody or antibody fragment, of the invention attached to (2) an effector molecule. The effector molecule can be any molecule that one wishes to deliver to the cancer cell, including, but not limited to (i) a label, which can generate a detectable signal, directly or indirectly, or (ii) a cancer therapeutic agent, such as a toxin that is either cytotoxic, cytostatic or otherwise prevents or reduces the ability of the cancer cells to divide and/or metastasize.

The term "isolated nucleic acid sequences" as used herein refers to a nucleic acid substantially free of cellular material or culture medium when produced by recombinant DNA techniques, or chemical precursors, or other chemicals when chemically synthesized. An isolated nucleic acid is also substantially free of sequences which naturally flank the nucleic acid (i.e. sequences located at the 5' and 3' ends of the nucleic acid) from which the nucleic acid is derived. The term "nucleic acid" is intended to include DNA and RNA and can be either double stranded or single stranded.

The term "isolated proteins" refers to a protein substantially free of cellular material or culture medium when produced by recombinant DNA techniques, or chemical precursors or other chemicals when chemically synthesized. It includes the light chain complementarity regions 1, 2 and 3 of the invention, heavy chain complementarity regions 1, 2 and 3 of the invention, light chain variable regions of the invention, heavy chain variable regions of the invention, binding proteins of the invention and antigen to which the binding proteins of the invention bind.

The term "light chain complementarity determining region" as used herein refers to regions of hypervariability within the light chain variable region of an antibody molecule. Light chain variable regions have three complementarity determining regions termed light chain complementarity determining region 1, light chain complementarity determining region 2 and light chain complementarity determining region 3 from the amino terminus to the carboxy terminus.

The term "light chain variable region" as used herein refers to the variable region of a light chain.

The phrase "modification in the N-terminal di-leucine motif" in GLUT8 refers to a change in the N-terminal di-leucine motif which effects the localization of GLUT8 so that GLUT8 is expressed on the surface of the cell, preferably a cancer cell. In one embodiment of the invention, the N-terminal di-leucine motif is changed to a di-alanine.

The term "modified bouganin" as used here means a modified bouganin that has a reduced propensity to activate an immune response as described in PCT/CA2005/000410 and U.S. patent application Ser. No. 11/084,080. In one example, the modified bouganin has the amino acid sequence (SEQ ID NO: 29):

```
YNTVSFNLGEAYEYPTFIQDLRNELAKGTPVCQLPVTLQTIADDKRFVLV

DITTTSKKTVKVAIDVTDVYVVGYQDKWDGKDRAVFLDKVPTVATSKLFP

GVTNRVTLTFDGSYQKLVNAAKADRKALELGVNKLEFSIEAIHGKTINGQ

EAAKFFLIVIQMVSEAARFKYIETEVVDRGLYGSFKPNFKVLNLENNWGD

ISDAIHKSSPQCTTINPALQLISPSNDPWVVNKVSQISPDMGILKFKSS

K.
```

The term "nucleic acid sequence" as used herein refers to a sequence of nucleoside or nucleotide monomers consisting of naturally occurring bases, sugars and intersugar (backbone) linkages. The term also includes modified or substituted sequences comprising non-naturally occurring monomers or portions thereof. The nucleic acid sequences of the present invention may be deoxyribonucleic acid sequences (DNA) or ribonucleic acid sequences (RNA) and may include naturally occurring bases including adenine, guanine, cytosine, thymidine and uracil. The sequences may also contain modified bases. Examples of such modified bases include aza and deaza adenine, guanine, cytosine, thymidine and uracil; and xanthine and hypoxanthine.

The term "sample" as used herein refers to any fluid, cell or tissue sample from a subject which can be assayed for cancer.

The term "sequence identity" as used herein refers to the percentage of sequence identity between two polypeptide sequences. In order to determine the percentage of identity between two polypeptide sequences, the amino acid sequences of such two sequences are aligned, preferably using the Clustal W algorithm (Thompson, J D, Higgins D G, Gibson T J, 1994, Nucleic Acids Res. 22 (22): 4673-4680), together with BLOSUM 62 scoring matrix (Henikoff S, and Henikoff J. G., 1992, Proc. Natl. Acad. Sci. USA 89: 10915-10919) and a gap opening penalty of 10 and gap extension penalty of 0.1, so that the highest order match is obtained between two sequences wherein at least 50% of the total length of one of the sequences is involved in the alignment. Other methods that may be used to align sequences are the alignment method of Needleman and Wunsch (J. Mol. Biol., 1970, 48: 443), as revised by Smith and Waterman (Adv. Appl. Math., 1981, 2: 482) so that the highest order match is obtained between the two sequences and the number of identical amino acids is determined between the two sequences. Other methods to calculate the percentage identity between two amino acid sequences are generally art recognized and include, for example, those described by Carillo and Lipton (SIAM J. Applied Math., 1988, 48:1073) and those described in Computational Molecular Biology, Lesk, e.d. Oxford University Press, New York, 1988, Biocomputing: Informatics and Genomics Projects. Generally, computer programs will be employed for such calculations. Computer programs that may be used in this regard include, but are not limited to, GCG (Devereux et al., Nucleic Acids Res., 1984, 12: 387) BLASTP, BLASTN and FASTA (Altschul et al., J. Molec. Biol., 1990: 215: 403).

The phrase "N-terminal di-leucine motif" refers to the N-terminal di-leucine motif in GLUT8 that is involved in localization of the protein to the intracellular compartment of the cell. In one embodiment of the invention, the di-leucine motif is at positions 12 to 13 of GLUT8.

The term "subject" as used herein refers to any member of the animal kingdom, preferably a mammal, more preferably a human being. In a preferred embodiment, the subject is suspected of having or has cancer.

As used herein, the phrase "treating cancer" refers to inhibiting cancer cell replication, inhibiting cancer spread (metastasis), inhibiting tumor growth, reducing cancer cell number or tumor growth, decreasing the malignant grade of a cancer (e.g., increased differentiation), or improving cancer-related symptoms.

The term "variant" as used herein includes modifications or chemical equivalents of the amino acid and nucleotide sequences of the present invention that perform substantially the same function as the proteins or nucleic acid molecules of the invention in substantially the same way. For example, variants of proteins of the invention include, without limitation, conservative amino acid substitutions. Variants of proteins of the invention also include additions and deletions to the proteins of the invention. In addition, variant peptides and variant nucleotide sequences include analogs and derivatives thereof.

(B) Proteins and Nucleic Acids of the Invention (i) Light and Heavy Chain Complementarity Determining Regions and Light and Heavy Chain Variable Regions The invention provides isolated light chain complementarity determining region 1 comprising the amino acid sequence RASQDISNYLA (SEQ ID NO:1). The invention also provides isolated light chain complementarity determining region 2 comprising the amino acid sequence AASSLHS (SEQ ID NO:2). In addition, the invention provides isolated light chain complementarity determining region 3 comprising the amino acid sequence LQYSTYPIT (SEQ ID NO:3).

The invention provides isolated heavy chain complementarity determining region 1 comprising the amino acid sequence NYAMS (SEQ ID NO:4). The invention also provides isolated heavy chain complementarity determining region 2 comprising the amino acid sequence AITPSGGSTNYADSVKG (SEQ ID NO:5). In addition, the invention provides isolated heavy chain complementarity determining region 3 comprising the amino acid sequence VPYRSTWYPLY (SEQ ID NO:6).

The invention provides isolated light chain complementarity determining regions 1, 2 and 3, comprising the amino acid sequences RASQDISNYLA (SEQ ID NO:1), AASSLHS (SEQ ID NO:2) and LQYSTYPIT (SEQ ID NO:3), respectively; and isolated heavy chain complementarity determining regions 1, 2 and 3, comprising the amino acid sequences NYAMS (SEQ ID NO:4), AITPSGGSTNYADSVKG (SEQ ID NO:5) and VPYRSTWYPLY (SEQ ID NO:6), respectively.

The invention also includes variants of the CDR sequences that can bind to the same epitope or antigen recognized by the CDR sequences disclosed above.

Additional aspects of the invention are isolated light chain variable regions comprising light chain complementarity determining regions 1, 2 and/or 3 of the invention (SEQ ID NOS:1-3); and heavy chain variable regions comprising the heavy chain complementarity determining regions 1, 2 and/or 3 of the invention (SEQ ID NOS:4-6). In one embodiment, the light chain variable region comprises the amino acid sequence shown in FIG. 1 (SEQ ID NO:7), and the heavy chain variable region comprises the amino acid sequence shown in FIG. 2 (SEQ ID NO:9).

The invention also includes variants of the isolated light chain variable regions and heavy chain variable regions that can bind to the same epitope or antigen recognized by the isolated light chain variable regions and isolated heavy chain variable regions disclosed above.

A person skilled in the art will appreciate that the invention includes variants to the amino acid sequences of SEQ ID NOS:1-6, 7 and 9, including chemical equivalents to the sequences disclosed by the present invention. Such equivalents include proteins that perform substantially the same function as the specific proteins disclosed herein in substantially the same way. A functional variant of a CDR sequence will be able to bind to the antigen or epitope recognized by the native CDR sequence. For example, equivalents include, without limitation, conservative amino acid substitutions.

In one embodiment, the variant amino acid sequences of the light chain complementarity determining regions 1, 2 and 3, and the heavy chain complementarity determining regions 1, 2 and 3 have at least 50%, preferably at least 60%, more preferably at least 70%, most preferably at least 80%, and even more preferably at least 90% sequence identity to SEQ ID NOS:1-6, respectively.

In another embodiment, the variant amino acid sequences of the light chain variable region and the heavy chain variable region have at least 50%, preferably at least 60%, more preferably at least 70%, most preferably at least 80%, and even more preferably at least 90% sequence identity to SEQ ID NOS:7 and 9, respectively.

The invention also provides an isolated nucleic acid sequence encoding the light chain variable region of the invention, and an isolated nucleic acid sequence encoding the heavy chain variable region of the invention. In one embodiment, the light chain variable region comprises the nucleic acid sequence shown in FIG. 1 (SEQ ID NO: 8). In another embodiment, the heavy chain variable region comprises the nucleic acid sequence shown in FIG. 2 (SEQ ID NO:10). The invention also includes variants to the nucleic acid sequences that encode for the light chain variable region and heavy chain variable region of the invention. For example, the variants include nucleotide sequences that hybridize to the nucleic acid sequences encoding the light chain variable region and heavy chain variable region of the invention under at least moderately stringent hybridization conditions.

The invention also provides isolated nucleic acid sequences encoding light chain complementarity determining regions 1, 2 and/or 3, comprising the amino acid sequences RASQDISNYLA (SEQ ID NO:1), AASSLHS (SEQ ID NO:2) and LQYSTYPIT (SEQ ID NO:3), respectively; and isolated nucleic acid sequences encoding heavy chain complementarity determining regions 1, 2 and/or 3, comprising the amino acid sequences NYAMS (SEQ ID NO:4), AITPSGGSTNYADSVKG (SEQ ID NO:5) and VPYRSTWYPLY (SEQ ID NO:6), respectively. The invention also provides an isolated nucleic acid sequence encoding the light chain variable region shown in FIG. 1 (SEQ ID NO:7), and an isolated nucleic acid sequence encoding the heavy chain variable region shown in FIG. 2 (SEQ ID NO:9).

The invention also includes isolated nucleic acid sequences encoding variants of the CDR sequences and variable region sequences discussed above.

Variant nucleic acid sequences include nucleic acid sequences that hybridize to the nucleic acid sequences encoding the amino acid sequences shown in SEQ ID NOS:1-6, 7 and 9 and variants thereof under at least moderately stringent hybridization conditions.

(ii) Binding Proteins

Another aspect of the invention is a binding protein, preferably an antibody or antibody fragment, that comprises at least one light chain complementarity determining region of the invention (i.e. one or more of SEQ ID NOS:1-3) and/or at least one heavy chain complementarity determining region of the invention (i.e. one or more of SEQ ID NOS:4-6). Such a binding protein can be generally referred to herein as "a binding protein of the invention", or preferably "an antibody or antibody fragment of the invention".

In one embodiment, the binding protein, preferably an antibody or antibody fragment, comprises the light chain complementarity determining regions 1, 2 and 3, comprising the amino acid sequences RASQDISNYLA (SEQ ID NO:1), AASSLHS (SEQ ID NO:2) and LQYSTYPIT (SEQ ID NO:3), respectively; and heavy chain complementarity determining regions 1, 2 and 3, comprising the amino acid sequences NYAMS (SEQ ID NO:4), AITPSGGSTNYADSVKG (SEQ ID NO:5) and VPYRSTWYPLY (SEQ ID NO:6), respectively. The invention also provides a binding protein, preferably an antibody or antibody fragment, that comprises the light chain variable region shown in FIG. 1 (SEQ ID NO:7) and/or the heavy chain variable region shown in FIG. 2 (SEQ ID NO:9).

A person skilled in the art will appreciate that the invention includes variants to the specific binding proteins disclosed above, including chemical equivalents to the sequences disclosed above that perform substantially the same function as the binding proteins disclosed above in substantially the same way. A functional variant of a binding protein will be able to bind to the same antigen as the binding proteins disclosed above. In one embodiment, the binding protein binds to glucose transporter 8 or variants thereof, a protein comprising any one of the amino acid sequences of SEQ ID NOS:11-20, preferably SEQ ID NOS: 11-13, or a cancer-associated variant of GLUT8 that is expressed on the surface of cancer cells.

The inventors have discovered a novel variant of GLUT8 that is expressed on cancer cells. Accordingly, the invention includes a binding protein that is specific for a cancer-associated variant of glucose transporter 8. In one embodiment, the cancer-associated variant of glucose transporter 8 comprises any one of the amino acid sequences defined by SEQ ID NOS: 11-13, or a variant thereof. In another embodiment of the invention, the cancer-associated variant of GLUT8, comprises GLUT8 that has a modification in the N-terminal di-leucine motif. In a further embodiment of the invention, the N-terminal di-leucine motif has been modified to di-alanine.

In certain embodiments, the antibody or antibody fragment comprises all or a portion of a heavy chain constant region, such as an IgG1, IgG2, IgG3, IgG4, IgA1, IgA2, IgE, IgM or IgD constant region. Preferably, the heavy chain constant region is an IgG1 heavy chain constant region. Furthermore, the antibody or antibody fragment can comprise all or a portion of a kappa light chain constant region or a lambda light chain constant region. Preferably, the light chain constant region is a kappa light chain constant region.

To produce human monoclonal antibodies, antibody producing cells (lymphocytes) can be harvested from a human having cancer and fused with myeloma cells by standard somatic cell fusion procedures thus immortalizing these cells and yielding hybridoma cells. Such techniques are well known in the art, (e.g. the hybridoma technique originally developed by Kohler and Milstein (*Nature* 256:495-497 (1975)) as well as other techniques such as the human B-cell hybridoma technique (Kozbor et al., *Immunol. Today* 4:72 (1983)), the EBV-hybridoma technique to produce human monoclonal antibodies (Cole et al., *Methods Enzymol,* 121: 140-67 (1986)), and screening of combinatorial antibody libraries (Huse et al., *Science* 246:1275 (1989)). Hybridoma cells can be screened immunochemically for production of antibodies specifically reactive with cancer cells and the monoclonal antibodies can be isolated.

Specific antibodies, or antibody fragments, reactive against particular antigens or molecules, such as antigens or molecules on a cancer cell, may also be generated by screening expression libraries encoding immunoglobulin genes, or portions thereof, expressed in bacteria with cell surface components. For example, complete Fab fragments, VH regions and FV regions can be expressed in bacteria using phage expression libraries (See for example Ward et al., *Nature* 341:544-546 (1989); Huse et al., *Science* 246:1275-1281 (1989); and McCafferty et al., *Nature* 348:552-554 (1990)).

The present invention includes all antibodies and antibody fragments that bind to the same antigen as the antibodies or antibody fragments of the invention. A person skilled in the art will appreciate that binding assays can be used to find other antibodies and antibody fragments with the same binding specificities as the antibodies and antibody fragments of the invention. As exemplified, below, a competition binding assay can be used to find such other antibodies.

Before a competition assay is performed using flow cytometry, the minimal concentration of antibody of the invention (Ab1) that gives maximal binding against a fixed number of cancer cells (for example, A-375 cells for VB1-050) is determined. A total of $10^6$ cells are harvested from exponentially growing cultures and incubated with various antibody concentrations for 1 hr at 4° C. The cells are washed and incubated with a suitable detection antibody for an additional hour at 4° C. After washing, the cells are analyzed by flow cytometry. For each test antibody, a saturation curve is generated from the data by plotting median fluorescence against the antibody concentration.

For the competition assay, cancer cells are prepared as above and treated in duplicate with a fixed concentration of antibody (Ab1). The fixed concentration is the minimal concentration of antibody that generates maximal binding against a fixed number of cancer cells as determined above. Immediately following the addition of the Ab1, varying concentrations of the potential inhibitory antibody (Ab2) is added to each tube and the mixture incubated for 1 hr at 4° C. Both the percent inhibition and change over maximum median fluorescence are calculated by subtracting the background fluorescence (PBS-5% FCS) from the median fluorescence reading for each test sample (Ab1+Ab2). The result is then divided by the median fluorescence of Ab1 alone (maximal binding) minus the background (see below). The percent of inhibition result is obtained by multiplying by 100. The mean of the replicates along with their respective standard error is plotted against antibody concentration. The following formula is used to calculate the percent inhibition:

$$PI=[(MF_{(Ab1+Ab2)}-MF_{Bgd})/(MF_{Ab1}-MF_{Bgd})]\times 100$$

where PI=percent inhibition; $MF_{(Ab1+Ab2)}$=median fluorescence measured for Ab1+Ab2 mixture; and $MF_{Bgd}$=background median fluorescence with PBS-5% FCS.

Accordingly, the invention provides a binding protein capable of binding an antigen on a cancer cell wherein the binding protein can be identified by a method comprising:

(1) incubating a fixed number of cancer cells with a minimal concentration of a binding protein of the invention, preferably an antibody or antibody fragment (Ab1) that generates maximal binding against the fixed number of cancer cells and measuring median fluorescence of Ab1 ($MF_{Ab1}$);

(2) testing two or more concentrations of a test binding protein (Ab2) by adding Ab2 to the Ab1 and cancer cells, and measuring median fluorescence ($MF_{(Ab1+Ab2)}$);

(3) measuring background median fluorescence ($MF_{bgd}$);

(4) calculating PI, wherein $$PI=[(MF_{(Ab1+Ab2)}-MF_{Bgd})/(MF_{Ab1}-MF_{Bgd})]\times 100;$$

and (5) comparing the PI to a control PI value;

wherein, a PI that has a statistically significant difference from the control PI indicates that the test binding protein is capable of binding the antigen on the cancer cell.

A person skilled in the art will appreciate that affinity maturation techniques could be used modify the binding proteins or immunoconjugates of the invention by increasing its affinity for its antigen, glucose transporter 8 or variants thereof.

Two strategies are routinely used to enhance the binding affinity of an antibody. One approach utilizes the resolution of the crystal structure of the Ab-Ag complex to identify the key residues involved in the antigen binding (Davies D. R., Cohen G. H. 1996. Interactions of protein antigens with antibodies. Proc Natl. Acad. Sci. U.S.A. 93, 7-12). Subsequently, those residues can be mutated to enhance the interaction. The other approach mimics an in vivo antigen stimulation that drives the affinity maturation of immunoglobulin produced by B cells. During the maturation of the immune response, the variable regions of the immunoglobulins are subjected to somatic mutations (Mc Heyzer-Williams M. 2003. B-cell signaling mechanism and activation. Fundamental Immunology, Fifth edition, 195-225). This process, highly specific for the immune system, is characterized by the introduction of point mutations at a very high rate. It occurs only within the DNA fragments encoding the variable regions and excludes the conserved domains. The B cells expressing the somatically mutated variant antibody are then subjected to an antigen-mediated selection resulting in the selection of higher affinity immunoglobulin. In order to replicate this phenomenon in vitro, several approaches have been used to introduce mutations either by random or targeted processes. The random mutations can be introduced using error-prone PCR, chain shuffling or mutator *E. coli* strains (Clackson T. Hoogenboom N. R., Griffiths A. D. and Winter G. 1991 Making antibody fragments using phage display libraries. Nature 352, 624-628, Hawkins R. E., Russell S. J. and Winter G. 1992. Selection of phage antibodies by binding affinity. Mimicking affinity maturation. J. Mol. Biol. 226, 889-896, Low N., Holliger P. and Winter G. 1996. Mimicking somatic hypermutation: affinity maturation of antibodies displayed on bacteriophage using a bacterial mutator strain. J. Mol. Biol. 260, 359-368). This strategy leads to the creation of large libraries in which reactive clones are selected with a display technology such as ribosome, phage or yeast (Min L. (2000). Applications of display technology in protein analysis. Nat. Biotechnol. 18, 1251-1256).

The targeted mutations of the CDRs, especially CDR3 of the light and heavy chains, have been shown to be an effective technique for increasing antibody affinity. Blocks of 3 to 4 amino acids of the CDR3 or specific regions called "hot-spots" are targeted for mutagenesis. Yang et al reported an increase of 420 fold of an anti-HIV gp120 Fab fragment by mutating four CDR residues (Yang W. P., Green K., Pinz-Sweeney S., Briones A. T., Burton D. R. and Barbas C. F. III. 1995. CDR walking mutagenesis for the affinity maturation of a potent human anti-HIV-1 antibody into picomolar range. J. Mol. Biol., 254, 392-403). One mutation in the VL CDR3 combined with three mutations in the VH CDR3 of the C6.5 scFv yielded a 1230 fold increased affinity (Schier R., McCall A., Adams G. P., Marshall K. W., Merrit H., Yin M., Crawford R. S. Weiner L. M., Marks C. and Marks J. D. 1996. Isolation of picomolar affinity anti-c-erbB-2 single-chain Fv by molecular evolution of the complementary determining regions in the center of the antibody binding site. J. Mol. Biol., 263, 551-567).

"Hot spots" are the sequences where somatic hypermutation takes place in vivo (Neuberger M. S. and Milstein C. 1995. Somatic hypermutation. Curr. Opin. Immunol. 7, 248-254). The hotspot sequences can be defined as consensus nucleotide sequences in certain codons. The consensus sequence is the tetranucleotide, RGYW (SEQ ID NO:31), in which R can be either A or G, Y can be C or T and W can be either A or T (Neuberger M. S and Milstein C. 1995. Somatic hypermutation. Curr. Opin. Immunol. 7, 248-254). In addition, the serine residues encoded by the nucleotides AGY are predominantly present in the CDRs regions of the variable domain over those encoded by TCN corresponding to a potential hot-spot sequences (Wagner S. D., Milstein C. and Neuberger M. S. 1995. Codon bias targets mutation. Nature, 376, 732). The structural analysis has shown that the CDR loops contribute the most to the antigen binding, especially the CDR3 loops (Giudicelli V., Chaume D. and Lefranc M. P. 2004. IMGT/V-QUEST, an integrated software program for immunoglobulin and T cell receptor V-J and V-D-J rearrangement analysis. Nucleic Acids Res. 32, 435-440). Therefore, the nucleotide sequence of the CDRs of the heavy and light chains of each antibody of the invention is scanned for the presence of the hot-spot sequences and AGY codons. The identified hot-spots of the CDR regions of the light and heavy chain are compared to the germinal sequences of the heavy and light chains using the International ImMunoGen Tics database (IMGT, imgt.cines.fr/textes/vquest/) (Davies D. R., Padlan E. A. and Sheriff S. 1990. Antibody-antigen complexes. Annu. Rev. Biochem. 59, 439-473). A sequence, identical to the germ line, suggest that somatic mutation has not occurred; therefore the random mutations are introduced mimicking the somatic events occurring in vivo. In contrast, a different sequence shows that some somatic mutations have already occurred. It will remain to be determined if the in vivo somatic mutation was optimal. The hot-spots that code for buried or conserved amino acids within the CDRs are not mutagenized. These residues are usually critical for the overall structure and are unlikely to interact with the antigen since they are buried. In addition, the sequences can be compared to the predicted locations in the germ line sequences where somatic mutations occurred predominantly (Tomlinson I. M., Cox J. P. L., Gherardi E., Lesk A. M. and Chotia C. 1995. The structural repertoire of the human Vldomain. EMBO J. 14, 4628-4638, Tomlinson I. M., Walter G., Jones P. T., Dear P. N., Sonnhammer E. L. L. and Winter G. 1996. The imprint of somatic hypermutation on the repertoire of human germline V genes. J. Mol. Biol. 256, 813-817). A similar strategy was applied for the affinity maturation of BL22 scFv. A point mutation introduced in the CDR3 of the heavy resulted in 5 to 10 fold increase in binding activity on various CD22-positive cell lines (Salvatore G., Beers R., Margulies I., Kreitman R. J. and Pastan I. 2002. Improved cytotoxic activity toward cell lines and fresh leukemia cells of a mutant anti-CD22 immunotoxin obtained by antibody phage display. Clinical Cancer research, 8, 995-1002). Also, the mutation of various amino acids in the CDR1 and CDR2 loops also produced mutant with increase affinity ranging from 3 fold to 7 fold (Ho M., Kreitman J., Onda M. and Pastan I. 2005. In vitro antibody evolution targeting germline hot spots to increase activity of an anti-CD22 immunotoxin. J. Biol. Chem., 280, 607-617).

After mutations are introduced, either by random or targeted processes, the antibodies are expressed and assessed for function. For instance, functional screening can be based on binding. Once function is assessed, then DNA sequencing of the chosen antibodies can be carried out using known methods.

In another embodiment, the anchored periplasmic expression (APEx) method described by Harvey, B et al (PNAS 2004 Jun. 22; 101(25): 9193-8) is used for affinity maturation of the binding proteins or immunoconjugates of the invention.

Accordingly, the invention includes binding proteins of the invention that have been affinity maturized to increase the affinity of the binding protein to glucose transporter 8 or variants thereof; a protein comprising amino acid sequences of SEQ ID NOS:11-20, preferably SEQ ID NOS:11-13; or a cancer-associated variant of glucose transporter 8.

The invention also provides compositions comprising the binding proteins of the invention, preferably antibodies and antibody fragments, with a pharmaceutically acceptable excipient, carrier, buffer or stabilizer.

(iii) Novel Cancer-Associated Antigens

As mentioned above, the inventors have identified the antigen to which the binding proteins of the invention bind. The novel-cancer associated antigen is expressed on the surface of cancer cells and is not significantly expressed on the surface of normal cells. Accordingly, the invention includes an isolated protein that can specifically bind with one of the binding proteins of the invention, and nucleic acid sequences and uses thereof.

In one embodiment, the invention provides an isolated protein comprising glucose transporter 8 or variants thereof. In another embodiment, the invention provides an isolated protein comprising any one of the amino acid sequences of SEQ ID NOS: 11-20 or variants thereof. In a further embodiment, the invention provides an isolated protein comprising the amino acid sequence of SEQ ID NO:11 or a variant thereof. The invention also provides an isolated protein comprising the amino acid sequence of SEQ ID NO:12 or a variant thereof. Further, the invention provides an isolated protein comprising the amino acid sequence of SEQ ID NO:13 or a variant thereof. In addition, the invention provides a cancer-associated variant of glucose transporter 8 that is expressed on the surface of cancer cells. In one embodiment of the invention, the cancer-associated variant of GLUT8, comprises the amino acid sequence defined by any one of SEQ ID NOS: 11, 12 or 13, or variants thereof. In another embodiment of the invention, the cancer-associated variant of GLUT8, comprises GLUT8 that has a modification in the N-terminal di-leucine motif. In a further embodiment of the invention, the N-terminal di-leucine motif has been modified to di-alanine.

A person skilled in the art will appreciate that the invention includes variants to the amino acid sequences of SEQ ID NOS:11-13, including chemical equivalents to the sequences disclosed by the present invention. Such equivalents include proteins that perform substantially the same function as the specific proteins disclosed herein in substantially the same way. For example, equivalents include, without limitation, conservative amino acid substitutions.

In one embodiment, the variant amino acid sequences of the isolated proteins of the invention have at least 50%, preferably at least 60%, more preferably at least 70%, most preferably at least 80%, and even more preferably at least 90% sequence identity to SEQ ID NOS:11-13.

The invention includes the use of the isolated protein. For example, the use of the isolated proteins of the invention to generate binding proteins and immunoconjugates that can be used to treat or prevent cancer or that can be used to detect or monitor cancer in a subject. Accordingly, the invention includes the use of the isolated proteins of the invention in the manufacture of a medicament to treat or prevent cancer.

(C) Immunoconjugates

The invention also includes an immunoconjugate comprising (1) a binding protein of the invention, preferably an antibody or antibody fragment, that has been attached to (2) an effector molecule. In one embodiment, the binding protein of the invention binds to an antigen or molecule on a cancer cell.

The antigen can be glucose transporter 8 or variants thereof; a protein comprising any one of the amino acid sequences defined by SEQ ID NOS: 11-20, preferably SEQ ID NOS:11, 12 or 13; or a cancer-associated variant of glucose transporter 8. In one embodiment of the invention, the cancer-associated variant of GLUT8, comprises the amino acid sequence defined by any one of SEQ ID NOS: 11, 12 or 13, or variants thereof. In another embodiment of the invention, the cancer-associated variant of GLUT8, comprises GLUT8 that has a modification in the N-terminal di-leucine motif. In a further embodiment of the invention, the N-terminal di-leucine motif has been modified to di-alanine.

In a preferred, embodiment the effector molecule is (i) a label, which can generate a detectable signal, directly or indirect, or (ii) a cancer therapeutic agent, which is either cytotoxic, cytostatic or otherwise prevents or reduces the ability of the cancer cells to divide and/or metastasize. Such an immunoconjugate can be generally referred to as "the immunoconjugate of the invention" herein.

In an embodiment of the invention, the effector molecule is a cancer therapeutic agent. The cancer therapeutic agent is preferably a toxin that is either cytotoxic, cytostatic or otherwise prevents or reduces the ability of the cancer cells to divide and/or metastasize. Accordingly, one aspect of the invention is an immunoconjugate comprising (1) a binding protein of the invention, preferably an antibody or antibody fragment, attached to (2) a cancer therapeutic agent, such as a cytotoxin.

In another embodiment, the immunoconjugate is internalized and the cancer therapeutic agent is a cytotoxin that blocks the protein synthesis of the cell, therein leading to cell death. Importantly, since most normal cells do not widely express the antigen present on the cancer cells, they cannot bind and internalize the immunoconjugate, and are protected from the killing effect of the toxin or other cancer therapeutic agents.

A variety of effector molecules may be used in the immunoconjugates of the invention and a number of such effector molecules are intracellularly active molecules. Accordingly, in an embodiment of the invention, the immunoconjugate is internalized by the cancer cell.

In preferred embodiments, the effector molecule is a cancer therapeutic agent, more preferably a cytotoxin that comprises a polypeptide having ribosome-inactivating activity including, without limitation, gelonin, bouganin, saporin, ricin, ricin A chain, bryodin, diphtheria toxin, restrictocin, *Pseudomonas* exotoxin A and variants thereof. When the protein is a ribosome-inactivating protein, the immunoconjugate must be internalized upon binding to the cancer cell in order for the protein to be cytotoxic to the cells. Accordingly, in an embodiment of the invention, the effector molecule is a cytotoxin and the immunoconjugate is internalized by the cancer cell.

In one embodiment of the invention, the toxin is bouganin or *Pseudomonas* exotoxin A, and variants thereof. In another embodiment, the toxin is modified bouganin or a truncated form of *Pseudomonas* exotoxin A that lacks the cell binding domain. In a further embodiment, the toxin is a bouganin substantially devoid of T-cell epitopes or a truncated form of *Pseudomonas* exotoxin A that consists of amino acids 252-608.

In other nonlimiting embodiments, the cancer therapeutic agent comprises an agent that acts to disrupt DNA. Thus, the cancer therapeutic agents may be selected, without limitation, from enediynes (e.g., calicheamicin and esperamicin) and non-enediyne small molecule agents (e.g., bleomycin, methidiumpropyl-EDTA-Fe(II)). Other cancer therapeutic agents useful in accordance with the invention include, without limitation, daunorubicin, doxorubicin, distamycin A, cisplatin, mitomycin C, ecteinascidins, duocarmycin/CC-1065, and bleomycin/pepleomycin.

In other nonlimiting embodiments, the cancer therapeutic agent comprises an agent that acts to disrupt tubulin. Such agents may comprise, without limitation, rhizoxin/maytansine, paclitaxel, vincristine and vinblastine, colchicine, auristatin dolastatin 10 MMAE, and peloruside A.

In other nonlimiting embodiments, the cancer therapeutic portion of an immunoconjugate of the invention may comprise an alkylating agent including, without limitation, Asaley NSC 167780, AZQ NSC 182986, BCNU NSC 409962, Busulfan NSC 750, carboxyphthalatoplatinum NSC 271674, CBDCA NSC 241240, CCNU NSC 79037, CHIP NSC 256927, chlorambucil NSC 3088, chlorozotocin NSC 178248, cis-platinum NSC 119875, clomesone NSC 338947, cyanomorpholinodoxorubicin NSC 357704, cyclodisone NSC 348948, dianhydrogalactitol NSC 132313, fluorodopan NSC 73754, hepsulfam NSC 329680, hycanthone NSC 142982, melphalan NSC 8806, methyl CCNU NSC 95441, mitomycin C NSC 26980, mitozolamide NSC 353451, nitrogen mustard NSC 762, PCNU NSC 95466, piperazine NSC 344007, piperazinedione NSC 135758, pipobroman NSC 25154, porfiromycin NSC 56410, spirohydantoin mustard NSC 172112, teroxirone NSC 296934, tetraplatin NSC 363812, thio-tepa NSC 6396, triethylenemelamine NSC 9706, uracil nitrogen mustard NSC 34462, and Yoshi-864 NSC 102627.

In other nonlimiting embodiments, the cancer therapeutic agent portion of the immunoconjugate of the invention may comprise an antimitotic agent including, without limitation, allocoichicine NSC 406042, Halichondrin B NSC 609395, colchicine NSC 757, colchicine derivative NSC 33410, dolastatin 10 NSC 376128 (NG—auristatin derived), maytansine NSC 153858, rhizoxin NSC 332598, taxol NSC 125973, taxol derivative NSC 608832, thiocolchicine NSC 361792, trityl cysteine NSC 83265, vinblastine sulfate NSC 49842, and vincristine sulfate NSC 67574.

In other nonlimiting embodiments, the cancer therapeutic agent portion of the immunoconjugate of the invention may comprise an topoisomerase I inhibitor including, without limitation, camptothecin NSC 94600, camptothecin, Na salt NSC 100880, aminocamptothecin NSC 603071, camptothecin derivative NSC 95382, camptothecin derivative NSC 107124, camptothecin derivative NSC 643833, camptothecin derivative NSC 629971, camptothecin derivative NSC 295500, camptothecin derivative NSC 249910, camptothecin derivative NSC 606985, camptothecin derivative NSC 374028, camptothecin derivative NSC 176323, camptothecin derivative NSC 295501, camptothecin derivative NSC 606172, camptothecin derivative NSC 606173, camptothecin derivative NSC 610458, camptothecin derivative NSC 618939, camptothecin derivative NSC 610457, camptothecin derivative NSC 610459, camptothecin derivative NSC 606499, camptothecin derivative NSC 610456, camptothecin derivative NSC 364830, camptothecin derivative NSC 606497, and morpholinodoxorubicin NSC 354646.

In other nonlimiting embodiments, cancer therapeutic agent portion of the immunoconjugate of the invention may comprise an topoisomerase II inhibitor including, without limitation, doxorubicin NSC 123127, amonafide NSC 308847, m-AMSA NSC 249992, anthrapyrazole derivative NSC 355644, pyrazoloacridine NSC 366140, bisantrene HCL NSC 337766, daunorubicin NSC 82151, deoxydoxorubicin NSC 267469, mitoxantrone NSC 301739, menogaril NSC 269148, N,N-dibenzyl daunomycin NSC 268242, oxanthrazole NSC 349174, rubidazone NSC 164011, VM-26 NSC 122819, and VP-16 NSC 141540.

In other nonlimiting embodiments, the cancer therapeutic agent portion of the immunoconjugate of the invention may comprise an RNA or DNA antimetabolite including, without limitation, L-alanosine NSC 153353, 5-azacytidine NSC 102816, 5-fluorouracil NSC 19893, acivicin NSC 163501, aminopterin derivative NSC 132483, aminopterin derivative NSC 184692, aminopterin derivative NSC 134033, an antifol NSC 633713, an antifol NSC 623017, Baker's soluble antifol NSC 139105, dichlorallyl lawsone NSC 126771, brequinar NSC 368390, ftorafur (pro-drug) NSC 148958, 5,6-dihydro-5-azacytidine NSC 264880, methotrexate NSC 740, methotrexate derivative NSC 174121, N-(phosphonoacetyl)-L-aspartate (PALA) NSC 224131, pyrazofurin NSC 143095, trimetrexate NSC 352122, 3-HP NSC 95678, 2'-deoxy-5-fluorouridine NSC 27640, 5-HP NSC 107392, alpha-TGDR NSC 71851, aphidicolin glycinate NSC 303812, ara-C NSC 63878, 5-aza-2'-deoxycytidine NSC 127716, beta-TGDR NSC 71261, cyclocytidine NSC 145668, guanazole NSC 1895, hydroxyurea NSC 32065, inosine glycodialdehyde NSC 118994, macbecin II NSC 330500, pyrazoloimidazole NSC 51143, thioguanine NSC 752, and thiopurine NSC 755.

In another nonlimiting embodiment, the therapeutic portion of the immunoconjugates may be a nucleic acid. Nucleic acids that may be used include, but are not limited to, antisense RNA, genes or other polynucleotides, nucleic acid analogs such as thioguanine and thiopurine.

The present invention further provides immunoconjugates comprising (i) a binding protein of the invention, preferably an antibody or antibody fragment, attached to (2) an effector molecule, wherein the effector molecule is a label, which can generate a detectable signal, indirectly or directly. These immunoconjugates can be used for research or diagnostic applications, such as for the in vivo detection of cancer. The label is preferably capable of producing, either directly or indirectly, a detectable signal. For example, the label may be radio-opaque or a radioisotope, such as $^{3}H$, $^{14}C$, $^{32}P$, $^{35}S$, $^{123}I$, $^{125}I$, $^{131}I$; a fluorescent (fluorophore) or chemiluminescent (chromophore) compound, such as fluorescein isothiocyanate, rhodamine or luciferin; an enzyme, such as alkaline phosphatase, beta-galactosidase or horseradish peroxidase; an imaging agent; or a metal ion.

In another embodiment, the immunoconjugate is detectable indirectly. For example, a secondary antibody that is specific for the immunoconjugate and contains a detectable label can be used to detect the immunoconjugate.

The binding protein of the invention, preferably an antibody or antibody fragment, may be "attached to" the effector molecule by any means by which the binding protein can be associated with, or linked to, the effector molecule. For example, the binding protein may be attached to the effector molecule by chemical or recombinant means. Chemical means for preparing fusions or conjugates are known in the art and can be used to prepare the immunoconjugate. The method used to conjugate the binding protein and effector molecule must be capable of joining the binding protein with the effector molecule without interfering with the ability of the binding protein to bind to the antigen on the cancer cell.

The binding protein of the invention may be linked indirectly to the effector molecule. For example, the binding protein may be directly linked to a liposome containing the effector molecule of one of several types. The effector molecule(s) and/or binding protein may also be bound to a solid surface.

In one embodiment, the binding protein, preferably an antibody or antibody fragment, and effector molecule are both proteins and can be conjugated using techniques well known in the art. There are several hundred crosslinkers available that can conjugate two proteins. (See for example "Chemistry of Protein Conjugation and Crosslinking". 1991, Shans Wong, CRC Press, Ann Arbor). The crosslinker is generally chosen based on the reactive functional groups available or inserted on the binding protein, preferably an antibody or antibody fragment, and/or effector molecule. In addition, if there are no reactive groups, a photoactivatible crosslinker can be used. In certain instances, it may be desirable to include a spacer between the binding protein, preferably an antibody or antibody fragment, and effector molecule. Crosslinking agents known to the art include the homobifunctional agents: glutaraldehyde, dimethyladipimidate and Bis(diazobenzidine) and the heterobifunctional agents: m Maleimidobenzoyl-N-Hydroxysuccinimide and Sulfo-m Maleimidobenzoyl-N-Hydroxysuccinimide.

A binding protein-effector molecule protein fusion may also be prepared using recombinant DNA techniques. In such a case a DNA sequence encoding the binding protein is fused to a DNA sequence encoding the effector molecule, resulting in a chimeric DNA molecule. The chimeric DNA sequence is transfected into a host cell that expresses the fusion protein. The fusion protein can be recovered from the cell culture and purified using techniques known in the art.

Examples of attaching an effector molecule, which is a label, to the binding protein include the methods described in Hunter, et al., Nature 144:945 (1962); David, et al., Biochemistry 13:1014 (1974); Pain, et al., J. Immunol. Meth. 40:219 (1981); Nygren, J. Histochem. and Cytochem. 30:407 (1982); Wensel and Meares, Radioimmunoimaging And Radioimmunotherapy, Elsevier, N.Y. (1983); and Colcher et al., "Use Of Monoclonal Antibodies As Radiopharmaceuticals For The Localization Of Human Carcinoma Xenografts In Athymic Mice", Meth. Enzymol., 121:802-16 (1986).

(D) Preparation of Proteins of the Invention

A person skilled in the art will appreciate that the proteins of the invention, such as the light and heavy complementarity determining regions, the light and heavy chain variable regions, antibodies and antibody fragments, immunoconjugates and novel cancer-associated antigens of the invention, may be prepared in any of several ways, but is most preferably prepared using recombinant methods.

Accordingly, the nucleic acid molecules of the present invention may be incorporated in a known manner into an appropriate expression vector which ensures good expression of the proteins of the invention. Possible expression vectors include but are not limited to cosmids, plasmids, or modified viruses (e.g. replication defective retroviruses, adenoviruses and adeno-associated viruses), so long as the vector is compatible with the host cell used. The expression vectors are "suitable for transformation of a host cell", which means that the expression vectors contain a nucleic acid molecule of the invention and regulatory sequences selected on the basis of the host cells to be used for expression, which is operatively linked to the nucleic acid molecule. Operatively linked is intended to mean that the nucleic acid is linked to regulatory sequences in a manner which allows expression of the nucleic acid.

The invention therefore contemplates a recombinant expression vector of the invention containing a nucleic acid molecule of the invention, or a fragment thereof, and the necessary regulatory sequences for the transcription and translation of the inserted protein-sequence.

Suitable regulatory sequences may be derived from a variety of sources, including bacterial, fungal, viral, mammalian, or insect genes (For example, see the regulatory sequences described in Goeddel, Gene Expression Technology Methods in Enzymology 185, Academic Press, San Diego, Calif. (1990)). Selection of appropriate regulatory sequences is dependent on the host cell chosen as discussed below, and may be readily accomplished by one of ordinary skill in the art. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector.

The recombinant expression vectors of the invention may also contain a selectable marker gene which facilitates the selection of host cells transformed or transfected with a recombinant molecule of the invention. Examples of selectable marker genes are genes encoding a protein such as G418 and hygromycin which confer resistance to certain drugs, β-galactosidase, chloramphenicol acetyltransferase, firefly luciferase, or an immunoglobulin or portion thereof such as the Fc portion of an immunoglobulin preferably IgG. Transcription of the selectable marker gene is monitored by changes in the concentration of the selectable marker protein such as β-galactosidase, chloramphenicol acetyltransferase, or firefly luciferase. If the selectable marker gene encodes a protein conferring antibiotic resistance such as neomycin resistance transformant cells can be selected with G418. Cells that have incorporated the selectable marker gene will survive, while the other cells die. This makes it possible to visualize and assay for expression of recombinant expression vectors of the invention and in particular to determine the effect of a mutation on expression and phenotype. It will be appreciated that selectable markers can be introduced on a separate vector from the nucleic acid of interest.

The recombinant expression vectors may also contain genes which encode a fusion moiety which provides increased expression of the recombinant protein; increased solubility of the recombinant protein; and aid in the purification of the target recombinant protein by acting as a ligand in affinity purification. For example, a proteolytic cleavage site may be added to the target recombinant protein to allow separation of the recombinant protein from the fusion moiety subsequent to purification of the fusion protein. Typical fusion expression vectors include pGEX (Amrad Corp., Melbourne, Australia), pMal (New England Biolabs, Beverly, Mass.) and pRIT5 (Pharmacia, Piscataway, N.J.) which fuse glutathione S-transferase (GST), maltose E binding protein, or protein A, respectively, to the recombinant protein.

Recombinant expression vectors can be introduced into host cells to produce a transformed host cell. The terms "transformed with", "transfected with", "transformation" and "transfection" are intended to encompass introduction of nucleic acid (e.g. a vector) into a cell by one of many possible techniques known in the art. The term "transformed host cell" as used herein is intended to also include cells capable of glycosylation that have been transformed with a recombinant expression vector of the invention. Prokaryotic cells can be transformed with nucleic acid by, for example, electroporation or calcium-chloride mediated transformation. For example, nucleic acid can be introduced into mammalian cells via conventional techniques such as calcium phosphate or calcium chloride co-precipitation, DEAE-dextran mediated transfection, lipofectin, electroporation or microinjection. Suitable methods for transforming and transfecting host cells can be found in Sambrook et al. (Molecular Cloning: A Laboratory Manual, 3rd Edition, Cold Spring Harbor Laboratory Press, 2001), and other laboratory textbooks.

Suitable host cells include a wide variety of eukaryotic host cells and prokaryotic cells. For example, the proteins of the invention may be expressed in yeast cells or mammalian cells. Other suitable host cells can be found in Goeddel, Gene Expression Technology: Methods in Enzymology 185, Academic Press, San Diego, Calif. (1991). In addition, the proteins of the invention may be expressed in prokaryotic cells, such as *Escherichia coli* (Zhang et al., Science 303(5656): 371-3 (2004)). In addition, a *Pseudomonas* based expression system such as *Pseudomonas fluorescens* can be used (US Patent Application Publication No. US 2005/0186666, Schneider, Jane C et al.).

Yeast and fungi host cells suitable for carrying out the present invention include, but are not limited to *Saccharomyces cerevisiae*, the genera *Pichia* or *Kluyveromyces* and various species of the genus *Aspergillus*. Examples of vectors for expression in yeast *S. cerevisiae* include pYepSec1 (Baldari. et al., Embo J. 6:229-234 (1987)), pMFa. (Kurjan and Herskowitz, Cell 30:933-943 (1982)), pJRY 88 (Schultz et al., Gene 54:113-123 (1987)), and pYES2 (Invitrogen Corporation, San Diego, Calif.). Protocols for the transformation of yeast and fungi are well known to those of ordinary skill in the art (see Hinnen et al., Proc. Natl. Acad. Sci. USA 75:1929 (1978); Itoh et al., J. Bacteriology 153:163 (1983), and Cullen et al. (Bio/Technology 5:369 (1987)).

Mammalian cells suitable for carrying out the present invention include, among others: COS (e.g., ATCC No. CRL 1650 or 1651), BHK (e.g. ATCC No. CRL 6281), CHO (ATCC No. CCL 61), HeLa (e.g., ATCC No. CCL 2), 293 (ATCC No. 1573) and NS-1 cells. Suitable expression vectors for directing expression in mammalian cells generally include a promoter (e.g., derived from viral material such as polyoma, Adenovirus 2, cytomegalovirus and Simian Virus 40), as well as other transcriptional and translational control sequences. Examples of mammalian expression vectors include pCDM8 (Seed, B., Nature 329:840 (1987)) and pMT2PC (Kaufman et al., EMBO J. 6:187-195 (1987)).

Given the teachings provided herein, promoters, terminators, and methods for introducing expression vectors of an appropriate type into plant, avian, and insect cells may also be readily accomplished. For example, within one embodiment, the proteins of the invention may be expressed from plant cells (see Sinkar et al., J. Biosci (Bangalore) 11:47-58 (1987), which reviews the use of *Agrobacterium rhizogenes* vectors; see also Zambryski et al., Genetic Engineering, Principles and Methods, Hollaender and Setlow (eds.), Vol. VI, pp. 253-278, Plenum Press, New York (1984), which describes the use of expression vectors for plant cells, including, among others, PAPS2022, PAPS2023, and PAPS2034).

Insect cells suitable for carrying out the present invention include cells and cell lines from *Bombyx, Trichoplusia* or *Spodotera* species. Baculovirus vectors available for expression of proteins in cultured insect cells (SF 9 cells) include the pAc series (Smith et al., Mol. Cell. Biol. 3:2156-2165 (1983)) and the pVL series (Lucklow, V. A., and Summers, M. D., Virology 170:31-39 (1989)). Some baculovirus-insect cell expression systems suitable for expression of the recombinant proteins of the invention are described in PCT/US/02442.

Alternatively, the proteins of the invention may also be expressed in non-human transgenic animals such as rats, rabbits, sheep and pigs (Hammer et al. Nature 315:680-683 (1985); Palmiter et al. Science 222:809-814 (1983); Brinster et al. Proc. Natl. Acad. Sci. USA 82:4438-4442 (1985); Palmiter and Brinster Cell 41:343-345 (1985) and U.S. Pat. No. 4,736,866).

The proteins of the invention may also be prepared by chemical synthesis using techniques well known in the chemistry of proteins such as solid phase synthesis (Merrifield, J. Am. Chem. Assoc. 85:2149-2154 (1964); Frische et al., J. Pept. Sci. 2(4): 212-22 (1996)) or synthesis in homogenous solution (Houbenweyl, Methods of Organic Chemistry, ed. E. Wansch, Vol. 15 I and II, Thieme, Stuttgart (1987)).

N-terminal or C-terminal fusion proteins comprising the proteins of the invention conjugated with other molecules, such as proteins may be prepared by fusing, through recombinant techniques. The resultant fusion proteins contain a protein of the invention fused to the selected protein or marker protein as described herein. The recombinant protein of the invention may also be conjugated to other proteins by known techniques. For example, the proteins may be coupled using heterobifunctional thiol-containing linkers as described in WO 90/10457, N-succinimidyl-3-(2-pyridyldithio-proprionate) or N-succinimidyl-5 thioacetate. Examples of proteins which may be used to prepare fusion proteins or conjugates include cell binding proteins such as immunoglobulins, hormones, growth factors, lectins, insulin, low density lipoprotein, glucagon, endorphins, transferrin, bombesin, asialoglycoprotein glutathione-S-transferase (GST), hemagglutinin (HA), and truncated myc.

Accordingly, the invention provides a recombinant expression vector comprising the nucleic acid sequences that encode the proteins of the invention, such as the light and heavy chain complementarity determining regions, the light and heavy chain variable regions, the binding proteins, such as antibodies and antibody fragments, immunoconjugates of the invention and novel isolated proteins of the invention. Further, the invention provides a host cell comprising the recombinant expression vector of the invention.

(E) Therapeutic Methods and Pharmaceutical Compositions of the Binding Proteins and Immunotoxins of the Invention The inventors have shown that the binding proteins of the invention bind to glucose transporter 8 or variants thereof; a protein comprising any one of the amino acid sequences defined by SEQ ID NOS:11-20, preferably 11, 12 or 13; or a cancer-associated variant of glucose transporter 8. In one embodiment of the invention, the cancer-associated variant of GLUT8, comprises the amino acid sequence defined by any one of SEQ ID NOS: 11, 12 or 13, or variants thereof. In another embodiment of the invention, the cancer-associated variant of GLUT8, comprises GLUT8 that has a modification in the N-terminal di-leucine motif. In a further embodiment of the invention, the N-terminal di-leucine motif has been modified to di-alanine.

In addition, the inventors have shown that the binding proteins of the invention show specificity for cancer cells and that they are internalized by the cell. Thus, the binding proteins of the invention can be used for the targeted delivery of bioactive or medically relevant agents, such as imaging, radioactive or cytotoxic agents.

In one embodiment, the invention provides a method of treating or preventing cancer, comprising administering to a subject having or suspected of having cancer an effective amount of the immunoconjugate of the invention. In another embodiment, the invention provides the use of an effective amount of the immunoconjugate of the invention for the manufacture of a medicament for treating or preventing cancer. Furthermore, the invention provides the use of an effective amount of the immunoconjugate of the invention, further comprising the use of an additional cancer therapeutic agent for the manufacture of a medicament for simultaneous, separate or sequential treatment or prevention of cancer. The invention also provides the use of an effective amount of the immunoconjugate of the invention for treating or preventing cancer. Further, the invention provides the use of an effective amount of the immunoconjugate of the invention, further comprising the use of an additional cancer therapeutic agent for simultaneous, separate or sequential treatment or prevention of cancer.

In one embodiment of the invention, cancer includes, without limitation, stomach cancer, colon cancer, prostate cancer as well as cervical cancer, uterine cancer, ovarian cancer, pancreatic cancer, kidney cancer, liver cancer, head and neck cancer, squamous cell carcinoma, gastrointestinal cancer, breast cancer (such as carcinoma, ductal, lobular, and nipple), lung cancer, non-Hodgkin's lymphoma, multiple myeloma, leukemia (such as acute lymphocytic leukemia, chronic lymphocytic leukemia, acute myelogenous leukemia, and chronic myelogenous leukemia), brain cancer, neuroblastoma, sarcomas, rectum cancer, bladder cancer, pancreatic cancer, endometrial cancer, plasmacytoma, lymphoma, and melanoma. In a preferred embodiment, the cancer includes, without limitation, breast cancer, prostate cancer, colon cancer, bladder cancer, cervical cancer, kidney cancer, melanoma, liver cancer, ovarian cancer, pancreatic cancer, stomach cancer, and head and neck cancer.

The ability of the immunoconjugate of the invention to selectively inhibit or destroy cells having cancer may be readily tested in vitro using cancer cell lines. The selective inhibitory effect of the immunoconjugates of the invention may be determined, for example by demonstrating the selective inhibition of cellular proliferation of the cancer cells.

Toxicity may also be measured based on cell viability, for example, the viability of cancer and normal cell cultures exposed to the immunoconjugate may be compared. Cell viability may be assessed by known techniques, such as trypan blue exclusion assays.

In another example, a number of models may be used to test the effectiveness of the immunoconjugates of the invention. Thompson, E. W. et al. (Breast Cancer Res. Treatment 31:357-370 (1994)) has described a model for the determination of invasiveness of human breast cancer cells in vitro by measuring tumor cell-mediated proteolysis of extracellular matrix and tumor cell invasion of reconstituted basement membrane (collagen, laminin, fibronectin, Matrigel or gelatin). Other applicable cancer cell models include cultured ovarian adenocarcinoma cells (Young, T. N. et al. Gynecol. Oncol. 62:89-99 (1996); Moore, D. H. et al. Gynecol. Oncol. 65:78-82 (1997)), human follicular thyroid cancer cells (Demeure, M. J. et al., World J. Surg. 16:770-776 (1992)), human melanoma (A-2058) and fibrosarcoma (HT-1080) cell lines (Mackay, A. R. et al. Lab. Invest. 70:781 783 (1994)), and lung squamous (HS-24) and adenocircinoma (SB-3) cell lines (Spiess, E. et al. J. Histochem. Cytochem. 42:917-929 (1994)). An in vivo test system involving the implantation of tumors and measurement of tumor growth and metastasis in athymic nude mice has also been described (Thompson, E. W. et al., Breast Cancer Res. Treatment 31:357-370 (1994); Shi, Y. E. et al., Cancer Res. 53:1409-1415 (1993)).

The immunoconjugates of the invention may be formulated into pharmaceutical compositions for administration to subjects in a biologically compatible form suitable for administration in vivo. The substances may be administered to living organisms including humans, and animals. Administration of a therapeutically active amount of the pharmaceutical compositions of the present invention is defined as an amount effective, at dosages and for periods of time necessary to achieve the desired result. For example, a therapeutically active amount of a substance may vary according to factors such as the disease state, age, sex, and weight of the individual, and the ability of the recombinant protein of the invention to elicit a desired response in the individual. Dosage regime may be adjusted to provide the optimum therapeutic response. For example, several divided doses may be administered daily or the dose may be proportionally reduced as indicated by the exigencies of the therapeutic situation.

Accordingly, the present invention provides a pharmaceutical composition for treating or preventing cancer comprising the immunoconjugates of the invention, and a pharmaceutically acceptable carrier, diluent or excipient. In a preferred embodiment, the effector molecule of the immunoconjugate in the pharmaceutical composition is a cancer therapeutic agent, more preferably a toxin.

The pharmaceutical preparation comprising the immunoconjugate of the invention may be administered systemically. The pharmaceutical preparation may be administered directly to the cancer site. Depending on the route of administration, the immunoconjugate may be coated in a material to protect the compound from the action of enzymes, acids and other natural conditions that may inactivate the compound.

In accordance with one aspect of the present invention, the immunoconjugate is delivered to the patient by direct administration. The invention contemplates the pharmaceutical composition being administered in at least an amount sufficient to achieve the endpoint, and if necessary, comprises a pharmaceutically acceptable carrier.

The invention also provides methods for reducing the risk of post-surgical complications comprising administering an effective amount of the immunoconjugate of the invention before, during, or after surgery to treat cancer.

The compositions described herein can be prepared by per se known methods for the preparation of pharmaceutically acceptable compositions that can be administered to subjects, such that an effective quantity of the active substance is combined in a mixture with a pharmaceutically acceptable vehicle. Suitable vehicles are described, for example, in Remington's Pharmaceutical Sciences (Remington's Pharmaceutical Sciences, $20^{th}$ ed., Mack Publishing Company, Easton, Pa., USA, 2000). On this basis, the compositions include, albeit not exclusively, solutions of the substances in association with one or more pharmaceutically acceptable vehicles or diluents, and contained in buffered solutions with a suitable pH and iso-osmotic with the physiological fluids.

Pharmaceutical compositions include, without limitation, lyophilized powders or aqueous or non-aqueous sterile injectable solutions or suspensions, which may further contain antioxidants, buffers, bacteriostats and solutes that render the compositions substantially compatible with the tissues or the blood of an intended recipient. Other components that may be present in such compositions include water, surfactants (such as Tween), alcohols, polyols, glycerin and vegetable oils, for example. Extemporaneous injection solutions and suspensions may be prepared from sterile powders, granules, tablets, or concentrated solutions or suspensions. Immunoconjugate may be supplied, for example but not by way of limitation, as a lyophilized powder which is reconstituted with sterile water or saline prior to administration to the patient.

Pharmaceutical compositions of the invention may comprise a pharmaceutically acceptable carrier. Suitable pharmaceutically acceptable carriers include essentially chemically inert and nontoxic compositions that do not interfere with the effectiveness of the biological activity of the pharmaceutical composition. Examples of suitable pharmaceutical carriers include, but are not limited to, water, saline solutions, glycerol solutions, ethanol, N-(1(2,3-dioleyloxy)propyl)N,N, N-trimethylammonium chloride (DOTMA), diolesylphosphotidyl-ethanolamine (DOPE), and liposomes. Such compositions should contain a therapeutically effective amount of the compound, together with a suitable amount of carrier so as to provide the form for direct administration to the patient.

The composition may be in the form of a pharmaceutically acceptable salt which includes, without limitation, those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

In various embodiments of the invention, the pharmaceutical composition is directly administered systemically or directly to the area of the tumor(s).

The pharmaceutical compositions may be used in methods for treating animals, including mammals, preferably humans, with cancer. The dosage and type of immunoconjugate to be administered will depend on a variety of factors which may be readily monitored in human subjects. Such factors include the etiology and severity (grade and stage) of the cancer.

Clinical outcomes of cancer treatments using the immunoconjugates of the invention are readily discernable by one of skill in the relevant art, such as a physician. For example, standard medical tests to measure clinical markers of cancer may be strong indicators of the treatment's efficacy. Such tests may include, without limitation, physical examination, performance scales, disease markers, 12-lead ECG, tumor measurements, tissue biopsy, cytoscopy, cytology, longest diameter of tumor calculations, radiography, digital imaging of the tumor, vital signs, weight, recordation of adverse events, assessment of infectious episodes, assessment of concomitant medications, pain assessment, blood or serum chemistry, urinalysis, CT scan, and pharmacokinetic analysis. Furthermore, synergistic effects of a combination therapy comprising the immunoconjugate and another cancer therapeutic may be determined by comparative studies with patients undergoing monotherapy.

Another embodiment of the invention is a kit for treating or preventing cancer comprising an effective amount of the immunoconjugate of the invention, and directions for the use thereof to treat the cancer.

In the majority of approved anticancer therapies, the anticancer therapy is used in combination with other anticancer therapies. Accordingly, the invention provides a method of preventing or treating cancer using the immunoconjugate of the invention in combination with at least one additional anticancer therapy. The other cancer therapy may be administered prior to, overlapping with, concurrently, and/or after administration of the immunoconjugate. When administered concurrently, the immunoconjugate and the other cancer therapeutic may be administered in a single formulation or in separate formulations, and if separately, then optionally, by different modes of administration. The combination of one or more immunoconjugates and one or more other cancer therapies may synergistically act to combat the tumor or cancer. The other cancer therapies include, without limitation, radiation and other anticancer therapeutic agents. These other cancer therapeutics may include, without limitation, 2,2', 2"trichlorotriethylamine, 6-azauridine, 6-diazo-5-oxo-L-norleucine, 6-mercaptopurine, aceglarone, aclacinomycins actinomycin, altretamine, aminoglutethimide, aminoglutethimide, amsacrine, anastrozole, ancitabine, angiogenin antisense oligonucleotide, anthramycin, azacitidine, azaserine, aziridine, batimastar, bcl-2 antisense oligonucleotide, benzodepa, bicalutamide, bisantrene, bleomycin, buserelin, busulfan, cactinomycin, calusterone, carboplatin, carboquone, caminomycin, carmofur, carmustine, carubicin, carzinophilin, chlorambucil, chlornaphazine, chiormadinone acetate, chlorozotocin, chromomycins, cisplatin, cladribine, cyclophosphamide, cytarabine, dacarbazine, dactinomycin, daunorubicin, defosfamide, demecolcine, denopterin, detorubicin, diaziquone, docetaxel, doxifluridine, doxorubicin, droloxifene, dromostanolone, edatrexate, eflomithine, elliptinium acetate, emitefur, enocitabune, epirubicin, epitiostanol, esorubicin, estramustine, etoglucid, etoposide, fadrozole, fenretinide, floxuridine, fludarabine, fluorouracil, flutamide, folinic acid, formestane, fosfestrol, fotemustine, gallium nitrate, gemcitabine, goserelin, hexestrol, hydroxyurea, idarubicin, ifosfamide, improsulfan, interferon-alpha, interferon-beta, interferon-gamma, interleukin-2, L-asparaginase, lentinan, letrozole, leuprolide, lomustine, lonidamine, mannomustine, marcellomycin, mechlorethamine, mechlorethamine oxide hydrochloride, medroxyprogesterone, megestrol acetate, melengestrol, melphalan, menogaril, mepitiostane, methotrexate, meturedepa, miboplatin, miltefosine, mitobronitol, mitoguazone, mitolactol, mitomycins, mitotane, mitoxantrone, mopidamol, mycophenolic acid, nilutamide, nimustine, nitracine, nogalamycin, novembichin, olivomycins, oxaliplatin, paclitaxel, pentostatin, peplomycin, perfosfamide, phenamet, phenesterine, pipobroman, piposulfan, pirarubicin, piritrexim, plicamycin, podophyllinic acid 2-ethyl-hydrazide, polyestradiol phosphate, porfimer sodium, porfiromycin, prednimustine, procabazine, propagermanium, PSK, pteropterin, puromycin, quelamycin, ranimustine, razoxane, rodorubicin, roquinimex, sizofican, sobuzoxane, spirogermanium, streptonigrin, streptozocin, tamoxifen, taxotere, tegafur, temozolomide, teniposide, tenuzonic acid, testolacone, thiamiprine, thioguanine, thiotepa, Tomudex, topotecan, toremifene, triaziquone, triethylenemelamine, triethylenephosphoramide, triethylenethiophosphoramide, trilostane, trimetrexate, triptorelin, trofosfamide, trontecan, tubercidin, ubenimex, uracil mustard, uredepa, urethan, vinblastine, vincristine, zinostatin, and zorubicin, cytosine arabinoside, gemtuzumab, thioepa, cyclothosphamide, antimetabolites (e.g., methotrexate, 6-mercaptopurine, 6-thioguanine, cytarabine, 5-fluorouracil, fludarabine, gemcitabine, dacarbazine, temozoamide), hexamethylmelamine, LYSODREN, nucleoside analogues, plant alkaloids (e.g., Taxol, paclitaxel, camptothecin, topotecan, irinotecan (CAMPTOSAR, CPT-11), vincristine, vinca alkyloids such as vinblastine.) podophyllotoxin, epipodophyllotoxin, VP-16 (etoposide), cytochalasin B, gramicidin D, ethidium bromide, emetine, anthracyclines (e.g., daunorubicin), doxorubicin liposomal, dihydroxyanthracindione, mithramycin, actinomycin D, aldesleukin, allutamine, biaomycin, capecitabine, carboplain, chlorabusin, cyclarabine, daclinomycin, floxuridhe, lauprolide acetate, levamisole, lomusline, mercaptopurino, mesna, mitolanc, pegaspergase, pentoslatin, picamycin, riuxlmab, campath-1, straplozocin, tretinoin, VEGF antisense oligonucleotide, vindesine, and viriorelbine. Compositions comprising one or more cancer therapeutics (e.g., FLAG, CHOP) are also contemplated by the present invention. FLAG comprises fludarabine, cytosine arabinoside (Ara-C) and G-CSF. CHOP comprises cyclophosphamide, vincristine, doxorubicin, and prednisone. For a full listing of cancer therapeutics known in the art, see, e.g., the latest editions of The Merck Index and the Physician's Desk Reference.

Pharmaceutical compositions for combination therapy may also include, without limitation, antibiotics (e.g., dactinomycin, bleomycin, mithramycin, anthramycin), asparaginase, *Bacillus* and Guerin, diphtheria toxin, procaine, tetracaine, lidocaine, propranolol, anti-mitotic agents, abrin, ricinA, *Pseudomonas* exotoxin, nerve growth factor, platelet derived growth factor, tissue plasminogen activator, antihistaminic agents, anti-nausea agents, etc.

Indeed, administration of an effective amount of an immunoconjugate to a patient in need of such treatment may result in reduced doses of another cancer therapeutic having clinically significant efficacy. Such efficacy of the reduced dose of the other cancer therapeutic may not be observed absent administration with an immunoconjugate. Accordingly, the present invention provides methods for treating a tumor or cancer comprising administering a reduced dose of one or more other cancer therapeutics.

Moreover, combination therapy comprising an immunoconjugate to a patient in need of such treatment may permit relatively short treatment times when compared to the duration or number of cycles of standard treatment regimens. Accordingly, the present invention provides methods for treating a tumor or cancer comprising administering one or more other cancer therapeutics for relatively short duration and/or in fewer treatment cycles.

Thus, in accordance with the present invention, combination therapies comprising an immunoconjugate and another cancer therapeutic may reduce toxicity (i.e., side effects) of the overall cancer treatment. For example, reduced toxicity, when compared to a monotherapy or another combination therapy, may be observed when delivering a reduced dose of immunoconjugate and/or other cancer therapeutic, and/or when reducing the duration of a cycle (i.e., the period of a single administration or the period of a series of such administrations), and/or when reducing the number of cycles.

Accordingly, the invention provides a pharmaceutical composition comprising an immunoconjugate and one or more additional anticancer therapeutic, optionally in a pharmaceutically acceptable carrier.

The present invention also provides a kit comprising an effective amount of an immunoconjugate, optionally, in combination with one or more other cancer therapeutic, together with instructions for the use thereof to treat cancer.

As stated above, combination therapy with an immunoconjugate may sensitize the cancer or tumor to administration of an additional cancer therapeutic. Accordingly, the present invention contemplates combination therapies for preventing, treating, and/or preventing recurrence of cancer comprising administering an effective amount of an immunoconjugate prior to, subsequently, or concurrently with a reduced dose of a cancer therapeutic. For example, initial treatment with an immunoconjugate may increase the sensitivity of a cancer or tumor to subsequent challenge with a dose of cancer therapeutic. This dose is near, or below, the low range of standard dosages when the cancer therapeutic is administered alone, or in the absence of an immunoconjugate. When concurrently administered, the immunoconjugate may be administered separately from the cancer therapeutic, and optionally, via a different mode of administration.

In an alternate embodiment, administration of the additional cancer therapeutic may sensitize the cancer or tumor to the immunoconjugate or binding protein. In such an embodiment, the additional cancer therapeutic may be given prior to administration of the immunoconjugate or binding protein.

In one embodiment, the additional cancer therapeutic comprises cisplatin, e.g., PLATINOL or PLATINOL-AQ (Bristol Myers), at a dose ranging from approximately 5 to 10, 11 to 20, 21 to 40, or 41 to 75 mg/m$^2$/cycle.

In another embodiment, the additional cancer therapeutic comprises carboplatin, e.g., PARAPLATIN (Bristol Myers), at a dose ranging from approximately 2 to 3, 4 to 8, 9 to 16, 17 to 35, or 36 to 75 mg/m$^2$/cycle.

In another embodiment, the additional cancer therapeutic comprises cyclophosphamide, e.g., CYTOXAN (Bristol Myers Squibb), at a dose ranging from approximately 0.25 to 0.5, 0.6 to 0.9, 1 to 2, 3 to 5, 6 to 10, 11 to 20, or 21 to 40 mg/kg/cycle.

In another embodiment, the additional cancer therapeutic comprises cytarabine, e.g., CYTOSAR-U (Pharmacia & Upjohn), at a dose ranging from approximately 0.5 to 1, 2 to 4, 5 to 10, 11 to 25, 26 to 50, or 51 to 100 mg/m$^2$/cycle. In another embodiment, the additional cancer therapeutic comprises cytarabine liposome, e.g., DEPOCYT (Chiron Corp.), at a dose ranging from approximately 5 to 50 mg/m$^2$/cycle.

In another embodiment, the additional cancer therapeutic comprises dacarbazine, e.g., DTIC or DTICDOME (Bayer Corp.), at a dose ranging from approximately 15 to 250 mg/m$^2$/cycle or ranging from approximately 0.2 to 2 mg/kg/cycle.

In another embodiment, the additional cancer therapeutic comprises topotecan, e.g., HYCAMTIN (SmithKline Beecham), at a dose ranging from approximately 0.1 to 0.2, 0.3 to 0.4, 0.5 to 0.8, or 0.9 to 1.5 mg/m$^2$/Cycle.

In another embodiment, the additional cancer therapeutic comprises irinotecan, e.g., CAMPTOSAR (Pharmacia & Upjohn), at a dose ranging from approximately 5 to 9, 10 to 25, or 26 to 50 mg/m$^2$/cycle.

In another embodiment, the additional cancer therapeutic comprises fludarabine, e.g., FLUDARA (Berlex Laboratories), at a dose ranging from approximately 2.5 to 5, 6 to 10, 11 to 15, or 16 to 25 mg/m$^2$/cycle.

In another embodiment, the additional cancer therapeutic comprises cytosine arabinoside (Ara-C) at a dose ranging from approximately 200 to 2000 mg/m$^2$/cycle, 300 to 1000 mg/m$^2$/cycle, 400 to 800 mg/m$^2$/cycle, or 500 to 700 mg/m$^2$/cycle.

In another embodiment, the additional cancer therapeutic comprises docetaxel, e.g., TAXOTERE (Rhone Poulenc Rorer) at a dose ranging from approximately 6 to 10, 11 to 30, or 31 to 60 mg/m$^2$/cycle.

In another embodiment, the additional cancer therapeutic comprises paclitaxel, e.g., TAXOL (Bristol Myers Squibb), at a dose ranging from approximately 10 to 20, 21 to 40, 41 to 70, or 71 to 135 mg/kg/cycle.

In another embodiment, the additional cancer therapeutic comprises 5-fluorouracil at a dose ranging from approximately 0.5 to 5 mg/kg/cycle, 1 to 4 mg/kg/cycle, or 2-3 mg/kg/cycle.

In another embodiment, the additional cancer therapeutic comprises doxorubicin, e.g., ADRIAMYCIN (Pharmacia & Upjohn), DOXIL (Alza), RUBEX (Bristol Myers Squibb), at a dose ranging from approximately 2 to 4, 5 to 8, 9 to 15, 16 to 30, or 31 to 60 mg/kg/cycle.

In another embodiment, the additional cancer therapeutic comprises etoposide, e.g., VEPESID (Pharmacia & Upjohn), at a dose ranging from approximately 3.5 to 7, 8 to 15, 16 to 25, or 26 to 50 mg/m$^2$/cycle.

In another embodiment, the additional cancer therapeutic comprises vinblastine, e.g., VELBAN (Eli Lilly), at a dose ranging from approximately 0.3 to 0.5, 0.6 to 0.9, 1 to 2, or 3 to 3.6 mg/m$^2$/cycle.

In another embodiment, the additional cancer therapeutic comprises vincristine, e.g., ONCOVIN (Eli Lilly), at a dose ranging from approximately 0.1, 0.2, 0.3, 0.4, 0.5, 0.6 or 0.7 mg/m$^2$/cycle.

In another embodiment, the additional cancer therapeutic comprises methotrexate at a dose ranging from approximately 0.2 to 0.9, 1 to 5, 6 to 10, or 11 to 20 mg/m$^2$/cycle.

In another embodiment, an immunoconjugate is administered in combination with at least one other immunotherapeutic which includes, without limitation, rituxan, rituximab, campath-1, gemtuzumab, and trastuzutmab.

In another embodiment, an immunoconjugate is administered in combination with one or more anti-angiogenic agents which include, without limitation, angiostatin, thalidomide, kringle 5, endostatin, Serpin (Serine Protease Inhibitor), anti-thrombin, 29 kDa N-terminal and a 40 kDa C-terminal proteolytic fragments of fibronectin, 16 kDa proteolytic fragment of prolactin, 7.8 kDa proteolytic fragment of platelet factor-4, a 13 amino acid peptide corresponding to a fragment of platelet factor-4 (Maione et al., 1990, Cancer Res. 51:2077-2083), a 14-amino acid peptide corresponding to a fragment of collagen I (Tolma et al., 1993, J. Cell Biol. 122: 497-511), a 19 amino acid peptide corresponding to a fragment of Thrombospondin I (Tolsma et al., 1993, J. Cell Biol. 122:497-511), a 20-amino acid peptide corresponding to a fragment of SPARC (Sage et al., 1995, J. Cell. Biochem. 57:1329-1334), and a variant thereof, including a pharmaceutically acceptable salt thereof.

In another embodiment, an immunoconjugate is administered in combination with a regimen of radiation therapy. The therapy may also comprise surgery and/or chemotherapy. For example, the immunoconjugate may be administered in combination with radiation therapy and cisplatin (Platinol), fluorouracil (5-FU, Adrucil), carboplatin (Paraplatin), and/or paclitaxel (Taxol). Treatment with the immunoconjugate may allow use of lower doses of radiation and/or less frequent radiation treatments, which may for example, reduce the incidence of severe sore throat that impedes swallowing function potentially resulting in undesired weight loss or dehydration.

In another embodiment, an immunoconjugate is administered in combination with one or more cytokines which include, without limitation, a lymphokine, tumor necrosis factors, tumor necrosis factor-like cytokine, lymphotoxin, interferon, macrophage inflammatory protein, granulocyte monocyte colony stimulating factor, interleukin (including, without limitation, interleukin-1, interleukin-2, interleukin-6, interleukin-12, interleukin-15, interleukin-18), and a variant thereof, including a pharmaceutically acceptable salt thereof.

In yet another embodiment, an immunoconjugate is administered in combination with a cancer vaccine or biological agents including, without limitation, autologous cells or tissues, non-autologous cells or tissues, carcinoembryonic antigen, alpha-fetoprotein, human chorionic gonadotropin, BCG live vaccine, Mycobacterial cell wall-DNA complexes, melanocyte lineage proteins, and mutated, tumor-specific antigens.

In yet another embodiment, an immunoconjugate is administered in association with hormonal therapy. Hormonal therapeutics include, without limitation, a hormonal agonist, hormonal antagonist (e.g., flutamide, tamoxifen, leuprolide acetate (LUPRON)), and steroid (e.g., dexamethasone, retinoid, betamethasone, cortisol, cortisone, prednisone, dehydrotestosterone, glucocorticoid, mineralocorticoid, estrogen, testosterone, progestin).

In yet another embodiment, an immunoconjugate is administered in association with a gene therapy program to treat or prevent cancer.

Combination therapy may thus increase the sensitivity of the cancer or tumor to the administered immunoconjugate and/or additional cancer therapeutic. In this manner, shorter treatment cycles may be possible thereby reducing toxic events. The cycle duration may vary according to the specific cancer therapeutic in use. The invention also contemplates continuous or discontinuous administration, or daily doses divided into several partial administrations. An appropriate cycle duration for a specific cancer therapeutic will be appreciated by the skilled artisan, and the invention contemplates the continued assessment of optimal treatment schedules for each cancer therapeutic. Specific guidelines for the skilled artisan are known in the art. See, e.g., Therasse et al., 2000, "New guidelines to evaluate the response to treatment in solid tumors. European Organization for Research and Treatment of Cancer, National Cancer Institute of the United States, National Cancer Institute of Canada," J Natl Cancer Inst. February 2; 92(3):205-16.

It is contemplated that the immunoconjugate may be administered by any suitable method such as injection, oral administration, inhalation, transdermal or intratumorally, whereas any other cancer therapeutic may be delivered to the patient by the same or another mode of administration. Additionally, where multiple cancer therapeutics are intended to be delivered to a patient, the immunoconjugate and one or more of the other cancer therapeutics may be delivered by one method, whereas other cancer therapeutics may be delivered by another mode of administration.

(F) Diagnostic Methods and Agents Using the Binding Proteins and Immunotoxins of the Invention The binding proteins of the invention bind selectively to cancer cells or molecules internalized by cancer cells, and not significantly to normal cells. Therefore the binding proteins can be used in the diagnosis of cancer. As stated above, the inventors have shown that the binding proteins of the invention bind to glucose transporter 8 or variants thereof; proteins comprising any one of the amino acid sequence defined by SEQ ID NOS:11-20; or a cancer-associated variant of glucose transporter 8. In one embodiment of the invention, the cancer-associated variant of GLUT8, comprises the amino acid sequence defined by any one of SEQ ID NOS: 11, 12 or 13, or variants thereof. In another embodiment of the invention, the cancer-associated variant of GLUT8, comprises GLUT8 that has a modification in the N-terminal di-leucine motif. In a further embodiment of the invention, the N-terminal di-leucine motif has been modified to di-alanine.

In a preferred embodiment, the binding proteins are antibodies or antibody fragments of the invention. In addition, cancer cells may be evaluated to determine their susceptibility to the treatment methods of the invention by, for example, obtaining a sample of the cancer cells and determining the ability of the sample to bind to the binding proteins of the invention, preferably antibodies or antibody fragments.

Accordingly, the present invention includes diagnostic methods, agents, and kits that can be used by themselves or prior to, during or subsequent to the therapeutic method of the invention in order to determine whether or not cancer cells are present that express the antigen and can bind to the binding proteins of the invention, preferably antibodies and antibody fragments.

In one embodiment, the invention provides a method of detecting or monitoring cancer in a subject comprising the steps of (1) contacting a test sample taken from said subject with the binding proteins of the invention and that binds specifically to an antigen on the cancer cell to produce a binding protein-antigen complex;

(2) measuring the amount of binding protein-antigen complex in the test sample; and (3) comparing the amount of binding protein-antigen complex in the test sample to a control.

In one embodiment, the antigen is glucose transporter 8 or a variant thereof; a protein comprising any one of the amino acid sequences defined by SEQ ID NOS: 11-20, preferably SEQ ID NOS:11, 12 or 13; or a cancer-associated variant of glucose-transporter 8. In one embodiment, the cancer-associated variant of glucose transporter 8 comprises a mutation in the N-terminal di-leucine motif such that the variant glucose transporter 8 is localized in the cell membrane.

The invention further includes a kit for diagnosing cancer comprising any one of the binding proteins of the invention that binds to an antigen on the cancer cell and instructions for the use thereof to diagnose the cancer.

For use in the diagnostic applications, the binding proteins of the invention, preferably antibodies or antibody fragments, may be labeled with a detectable marker such as a radio-opaque or radioisotope, such as $^{3}H$, $^{14}C$, $^{32}P$, $^{35}S$, $^{123}I$, $^{125}I$, $^{131}I$; a fluorescent (fluorophore) or chemiluminescent (chromophore) compound, such as fluorescein isothiocyanate, rhodamine or luciferin; an enzyme, such as alkaline phosphatase, beta-galactosidase or horseradish peroxidase; an imaging agent; or a metal ion. As described above, methods of attaching a label to a binding protein, such as an antibody or antibody fragment, are known in the art.

Another aspect of the invention is a method of detecting or monitoring cancer in a subject comprising the steps of (1) measuring the amount of antibodies of the invention in a test sample taken from said subject; and (2) comparing the amount of antibodies of the invention in the test sample to a control.

In one embodiment, the amount of antibodies of the invention is measured by measuring the amount of antibodies of the invention in the test sample, for example by ELISA. In another embodiment, the amount of antibodies of the invention is measured by measuring the expression levels of nucleic acids encoding the antibodies of the invention in the test sample, for example by RT-PCR.

(G) Pharmaceutical Compositions, Methods and Uses of the Novel Cancer-Associated Antigen The invention provides a novel cancer-associated antigen that is expressed on the surface of cancer cells and not significantly expressed on the surface of normal cells. Thus, the novel cancer-associated antigen can be used in therapies to treat and prevent cancer, including using the novel cancer-associated antigen or fragments thereof to elicit an immune response in vivo. In addition, the invention includes using the novel cancer-associated variant of GLUT8 to detect or monitor cancer.

(i) Pharmaceutical Compositions

One embodiment of the invention is a pharmaceutical composition comprising an effective amount of the novel-cancer associated variant of GLUT8 or fragment thereof in admixture with a suitable diluent or carrier. Another embodiment of the invention is a pharmaceutical composition comprising an effective amount of an isolated nucleic acid encoding the novel cancer-associated variant of GLUT8 or a fragment thereof in admixture with a suitable diluent or carrier. A further aspect of the invention is a pharmaceutical composition comprising an effective amount of a recombinant expression comprising an nucleic acid sequence encoding the novel cancer-associated variant of GLUT8 or a fragment thereof in admixture with a suitable diluent or carrier.

For example, the pharmaceutical compositions of the invention can be used to treat or prevent cancer. In addition, the pharmaceutical compositions can be used to elicit an immune response in a subject against the novel cancer-associated variant of GLUT8.

The pharmaceutical composition can be prepared and administered as discussed above. The pharmaceutical composition can be used in combination with other anti-cancer therapeutic agents as discussed above.

Immunogencicity can be significantly improved if the immunizing agents (i.e. the novel cancer-associated variant of GLUT8 or fragment thereof, and/or nucleic acid sequences coding thereof, and/or recombinant expression vectors) and/or composition is, regardless of administration format, co-immunized with an adjuvant. Commonly, adjuvants are used as a 0.05 to 1.0 percent solution in phosphate buffered saline. Adjuvants enhance the immunogencity of an immunogen but are not necessarily immunogenic in of themselves. Adjuvants may act by retaining the immunogen locally near the site of administration to produce a depot effect facilitating a slow, sustained release of immunogen to cells of the immune system. Adjuvants can also attract cells of the immune system to an immunogen depot and stimulate such cells to elicit immune response. As such, embodiments of this invention encompass pharmaceutical compositions further comprising adjuvants.

Adjuvants have been used for many years to improve the host immune responses to, for example, vaccines. Intrinsic adjuvants (such as lipopolysaccharides) normally are the components of killed or attenuated bacteria used as vaccines. Extrinsic adjuvants are immunomodulators which are typically non-covalently linked to antigens and are formulated to enhance the host immune responses. Thus, adjuvants have been identified that enhance the immune response to antigens delivered parenterally. Some of these adjuvants are toxic, however, and can cause undesirable side-effects making them unsuitable for use in humans and many animals. Indeed, only aluminum hydroxide and aluminum phosphate (collectively commonly referred to as alum) are routinely used as adjuvants in human and veterinary vaccines. The efficacy of alum in increasing antibody responses to diphtheria and tetanus toxoids is well established. Notwithstanding, it does have limitations. For example, alum is ineffective for influenza vaccination and inconsistently elicits a cell mediated immune response with other immunogens. The antibodies elicited by alum-adjuvanted antigens are mainly of the IgG1 isotype in the mouse, which may not be optimal for protection by some vaccinal agents.

A wide range of extrinsic adjuvants can provoke potent immune responses to immunogens. These include saponins complexed to membrane protein antigens (immune stimulating complexes), pluronic polymers with mineral oil, killed mycobacteria and mineral oil, Freund's complete adjuvant, bacterial products such as muramyl dipeptide (MDP) and lipopolysaccharide (LPS), as well as lipid A, and liposomes.

In one aspect of this invention, adjuvants useful in any of the embodiments of the invention described herein are as follows. Adjuvants for parenteral immunization include aluminum compounds (such as aluminum hydroxide, aluminum phosphate, and aluminum hydroxy phosphate). The antigen can be precipitated with, or adsorbed onto, the aluminum compound according to standard protocols. Other adjuvants such as RIBI (ImmunoChem, Hamilton, Mont.) can also be used in parenteral administration.

Adjuvants for mucosal immunization include bacterial toxins (e.g., the cholera toxin (CT), the *E. coli* heat-labile toxin (LT), the *Clostridium difficile* toxin A and the pertussis toxin (PT), or combinations, subunits, toxoids, or mutants thereof). For example, a purified preparation of native cholera toxin subunit B (CTB) can be of use. Fragments, homologs, derivatives, and fusion to any of these toxins are also suitable, provided that they retain adjuvant activity. Preferably, a mutant having reduced toxicity is used. Suitable mutants have been described (e.g., in WO 95/17211 (Arg-7-Lys CT mutant), WO 96/6627 (Arg-192-Gly LT mutant), and WO 95/34323 (Arg-9-Lys and Glu-129-Gly PT mutant)). Additional LT mutants that can be used in the methods and compositions of the invention include, for example Ser-63-Lys, Ala-69-Gly, Glu-110-Asp, and Glu-112-Asp mutants. Other adjuvants (such as a bacterial monophosphoryl lipid A (MPLA) of various sources (e.g., *E. coli, Salmonella minnesota, Salmonella typhimurium*, or *Shigella flexneri*, saponins, or polylactide glycolide (PLGA) microspheres) can also be used in mucosal administration.

Adjuvants useful for both mucosal and parenteral immunization include polyphosphazene (for example, WO 95/2415), DC-chol (3 b-(N—(N',N'-dimethyl aminomethane)-carbamoyl) cholesterol (for example, U.S. Pat. No. 5,283,185 and WO 96/14831) and QS-21 (for example, WO 88/9336).

A subject may be immunized with a pharmaceutical composition comprising the cancer-associated variant of GLUT8 or fragments thereof, an isolated nucleic acid sequence encoding thereof and/or a recombinant expression vectors by any conventional route as is known to one skilled in the art. This may include, for example, immunization via a mucosal (e.g., ocular, intranasal, oral, gastric, pulmonary, intestinal, rectal, vaginal, or urinary tract) surface, via the parenteral (e.g., subcutaneous, intradermal, intramuscular, intravenous, or intraperitoneal) route or intranodally. Preferred routes depend upon the choice of the immunogen as will be apparent to one skilled in the art. The administration can be achieved in a single dose or repeated at intervals. The appropriate dosage depends on various parameters understood by skilled artisans such as the immunogen itself (i.e. peptide vs. nucleic acid (and more specifically type thereof)), the route of administration and the condition of the animal to be vaccinated (weight, age and the like).

The invention also provides kits comprising an effective amount of a pharmaceutical composition of the invention, optionally, in combination with one or more other cancer therapeutic, together with instructions for the use thereof.

(ii) Therapeutic Methods

As mentioned above, the novel cancer-associated variant of GLUT8 is present on cancer cells, but not significantly on normal cells. Thus, the novel cancer-associated antigen can be used in therapeutic methods to prevent or treat cancer. In addition, the novel cancer-associated antigen can be used to elicit an immune response in a subject, for example in a vaccine.

One embodiment of the invention is the use of the cancer-associated variant of GLUT8 or fragment thereof in the manufacture of a medicament to treat or prevent cancer. Another embodiment of the invention is the use of the cancer-associated variant of GLUT8 or fragment thereof in the manufacture of a medicament to elicit an immune response in a subject.

The invention also includes the use of an isolated nucleic acid sequence encoding the cancer-associated variant of GLUT8 or fragment thereof in the manufacture of a medicament to treat or prevent cancer. In addition, the invention includes the use of an isolated nucleic acid sequence encoding the cancer-associated variant of GLUT8 or fragment thereof in the manufacture of a medicament to elicit an immune response in a subject.

A further embodiment of the invention is the use of the recombinant expression vector comprising an isolated nucleic acid sequence encoding the cancer-associated variant of GLUT8 or fragment thereof in the manufacture of a medicament to treat or prevent cancer. Also, the invention includes the use of the recombinant expression vector comprising an isolated nucleic acid sequence encoding the cancer-associated variant of GLUT8 or fragment thereof in the manufacture of a medicament to elicit an immune response in a subject.

An additional embodiment of the invention is a method of treating or preventing cancer in a subject having or suspected of having cancer comprising administering to said subject an effective amount of a cancer-associated variant of GLUT8 or fragment thereof. In addition, the invention includes a method of treating or preventing cancer in a subject having or suspected of having cancer comprising administering to said subject an effective amount of the an isolated nucleic acid sequence encoding the cancer-associated variant of GLUT8 or fragment thereof. Further, the invention includes a method of treating or preventing cancer in a subject having or suspected of having cancer comprising administering to said subject an effective amount of a recombinant expression vector comprising an isolated nucleic acid sequence encoding the cancer-associated variant of GLUT8 or fragment thereof.

Another embodiment of the invention is a method of inducing an immune response in a subject against a cancer-associated variant of GLUT8, comprising administering to said subject an effective amount of a cancer-associated variant of GLUT8 or fragment thereof. In addition, the invention includes a method of inducing an immune response in a subject against the cancer-associated variant of GLUT8, comprising administering to said subject an effective amount of an isolated nucleic acid sequence encoding the cancer-associated variant of GLUT8 or fragment thereof. Further, the invention includes a method of inducing an immune response in a subject against the cancer-associated variant of GLUT8 comprising administering to said subject an effective amount of an recombinant expression vector comprising an isolated nucleic acid sequence encoding the cancer-associated variant of GLUT8 or fragment thereof.

(iii) Diagnostic Methods

The novel cancer-associated variant of GLUT8 is expressed on cancer cells and is not significantly expressed on normal cells, thus the detection of the novel cancer-associated variant of GLUT8 can be used as a diagnostic method for cancer. In a preferred embodiment, the cancer-associated variant of GLUT8 comprises the amino acid sequence defined by any one of SEQ ID NOS: 11, 12 or 13, or variants thereof. In another embodiment of the invention, the cancer-associated variant of GLUT8 comprises GLUT8 that has a modification in the N-terminal di-leucine motif. In a further embodiment of the invention, the N-terminal di-leucine motif has been modified to di-alanine.

One embodiment of the invention is a method of detecting or monitoring cancer in a subject having or suspected of having cancer, comprising detecting a cancer-associated variant of GLUT8 on a cell in the sample, wherein cancer is indicated, if the cancer-associated variant of GLUT8 is detected on the cell.

A number of techniques can be used to detect the cancer-associated variant of GLUT8 on a cell. For example, the binding proteins of the invention can be used in immunoassays to detect cell surface expression of the cancer-associated variant of GLUT8. A person skilled in the art will appreciate that a number of techniques can be used to detect and/or quantify cell surface expression of the cancer-associated variant of GLUT8, including Western blots, immunoprecipitation followed by SDS-PAGE, immunocytochemistry, FACS, protein arrays, and the like.

Another aspect of the invention is a method of detecting or monitoring cancer in a subject having or suspected of having cancer, comprising detecting the expression of a cancer-associated variant of GLUT8 in the cell in the sample, wherein cancer is indicated, if expression of the cancer-associated variant of GLUT8 is detected in the cell. In a preferred example, an RNA expression product encoding the cancer-associated variant of GLUT8 is used to detect the expression of the cancer-associated variant of GLUT8 in the cell. One skilled in the art will appreciate that the RNA expression product can be detected or quantified by detecting mRNA encoding the cancer-associated variant of GLUT8 or a fragment thereof, or oligonucleotides, cDNA, DNA, RNA, PCR products, synthetic DNA, synthetic RNA, or other combinations of naturally occurring or modified nucleotides which specifically and/or selectively hybridize to the mRNA encoding the cancer-associated variant of GLUT8 or a fragment thereof.

A number of methods can be used to detect and/or quantify RNA expression of the cancer-associated variant of GLUT8 in a cell including RT-PCR, nuclease protection assays, such as ribonuclease protection assays and S1 nuclease assays, and Northern blots and the like.

(H) Other Methods

Glucose transporter 8 has been shown to have sugar transporting activity. Thus, the invention includes a method of treating or preventing cancer in a subject by modulating the activity of the cancer-associated variant of glucose transporter 8 on or in a cancer cell.

In one embodiment of the invention, the method of treating or preventing cancer in a subject comprises preventing or decreasing the function of the cancer-associated variant of glucose transporter 8 as a transporter of sugar. In one embodiment of the invention, a binding protein of the invention is used to prevent or decrease the function of the cancer-associated variant of glucose transporter 8 as a transporter of sugar.

In another embodiment of the invention, a non-antibody inhibitor of glucose transporters is used to treat or prevent cancer in a subject.

There are several known inhibitors of the glucose transporter family of molecules including several members of the flavonoid family. For example, forskolin, phloretin (a flavonoid-like compound) and cytochalasin B are know to inhibit GLUT1 and their putative binding sites have been identified on a 3-dimensional molecular model of GLUT-1 (Salas-Burgos et al., Biophys. J. 87: 2990-2999, 2004). Quercetin, a flavonol, has been shown to inhibit GLUT2-mediated glucose transport (Song et al., J. Biol. Chem. 277:15252-15260, 2002). Oestradiol and the isoflavone phytoestrogen Genistein, are also inhibitors of GLUT1-mediated glucose transport and putative binding sites for these molecules have also been proposed (Afzal et al., Biochem J. 365: 707-719, 2002). The glucose transporter inhibitors forskolin, dipyridamole and isobutylmethylxanthine (IBMX) bind to both GLUT1 and GLUT4 (Hellwig & Joost, Mol. Pharmacol. 40:383-389, 1991). Cytochalasin B also binds GLUT4 (Wandel et al., Biochim. Biophys. Acta 1284:56-62, 1996.

In addition to these known inhibitors, a person skilled in the art will appreciate that there are a number of assays known to identify inhibitors of glucose transporters. For example, the effect of inhibitors on a glucose transporter can be assessed by expressing the GLUT of interest, preferably glucose transporter 8, in cells such as *Xenopus laevis* oocytes or CHO, measuring glucose uptake in the presence or absence of the inhibitor, and determining whether the inhibitor is competitive or non-competitive. Once the sequence of a given GLUT isoform is known, its sensitivity to a large number of molecules can be readily tested to identify drug candidates.

Accordingly, in the invention includes a method of treating or preventing cancer in a subject by administering an effective amount of a glucose transporter inhibitor to a subject in need thereof. The inhibitors include members of the Flavonoid family, such as quercetin or genistein, Flavonoid-like molecules, such as phloretin, Oestrogenic compounds, including oestradiol or genistein, Forskolin, Cytochalasin B, Dipyridamole and/or Isobutylmethylxanthine (IBMX).

In another embodiment of the invention, the function of the cancer-associated variant of glucose transporter 8 is prevented or decreased by decreasing or preventing the expression of the cancer-associated variant of glucose transporter 8 in the cell.

Standard techniques can be used to prevent or decrease the expression of the cancer-associated variant of glucose transporter 8 in a cell including using antisense, triple helix, or ribozyme molecules reactive to the transcripts of the cancer-associated variant of glucose transporter 8 gene.

For example, standard techniques can be utilized for the production of antisense nucleic acid molecules, i.e., molecules which are complementary to a sense nucleic acid encoding a polypeptide of interest, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire coding strand, or to only a portion thereof, e.g., all or part of the protein coding region (or open reading frame). An antisense nucleic acid molecule can be antisense to all or part of a non-coding region of the coding strand of a nucleotide sequence encoding a polypeptide of interest. The non-coding regions ("5' and 3' untranslated regions") are the 5' and 3' sequences that flank the coding region and are not translated into amino acids.

An antisense oligonucleotide can be, for example, about 5, 10, 15, 20, 25, 30, 35, 40, 45 or 50 nucleotides or more in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, $(acp3)_w$, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest).

Antisense nucleic acid molecules administered to a subject or generated in situ such that they hybridize with or bind to cellular mRNA encoding the polypeptide of interest to thereby inhibit expression, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention includes direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell, e.g., a T cell or brain cell, e.g., by linking the antisense nucleic acid molecules to peptides or antibodies which bind to cell surface receptors or antigens. The antisense nucleic acid molecules can also be delivered to cells using vectors, e.g., gene therapy vectors, described below. To achieve sufficient intracellular concentrations of the antisense molecules, vector constructs in which the antisense nucleic acid molecule is placed under the control of a strong pol II or pol III promoter are preferred.

An antisense nucleic acid molecule of interest can be an α-anomeric nucleic acid molecule. An α-anomeric nucleic acid molecule forms specific double-stranded hybrids with complementary RNA in which, contrary to the usual α-units, the strands run parallel to each other (Gaultier et al., 1987, Nucleic Acids Res. 15:6625-6641). The antisense nucleic acid molecule can also comprise a 2'-o-methylribonucleotide (Inoue et al., 1987, Nucleic Acids Res. 15:6131-6148) or a chimeric RNA-DNA analogue (Inoue et al., 1987, FEBS Lett. 215:327-330).

Ribozymes are catalytic RNA molecules with ribonuclease activity that are capable of cleaving a single-stranded nucleic acid, such as an mRNA, to which they have a complementary region, and can also be generated using standard techniques. Thus, ribozymes (e.g., hammerhead ribozymes (described in Haselhoff and Gerlach, 1988, Nature 334:585-591)) can be used to catalytically cleave mRNA transcripts to thereby inhibit translation of the protein encoded by the mRNA. A ribozyme having specificity for a nucleic acid molecule encoding a polypeptide of interest can be designed based upon the nucleotide sequence of a cDNA encoding a cancer-associated variant of GLUT8. For example, a derivative of a Tetrahymena L-19 IVS RNA can be constructed in which the nucleotide sequence of the active site is complementary to the nucleotide sequence to be cleaved in a Cech et al. U.S. Pat. No. 4,987,071; and Cech et al. U.S. Pat. No. 5,116,742. Alternatively, an mRNA encoding a polypeptide of interest can be used to select a catalytic RNA having a specific ribonuclease activity from a pool of RNA molecules. See, e.g., Bartel and Szostak, 1993, Science 261:1411-1418.

Triple helical structures can also be generated using well known techniques. For example, expression of a polypeptide of interest can be inhibited by targeting nucleotide sequences complementary to the regulatory region of the gene encoding the polypeptide (e.g., the promoter and/or enhancer) to form triple helical structures that prevent transcription of the gene in target cells. See generally Helene, 1991, Anticancer Drug Des. 6(6):569-84; Helene, 1992, Ann. N.Y. Acad. Sci. 660:27-36; and Maher, 1992, Bioassays 14(12):807-15.

In various embodiments, nucleic acid compositions can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al., 1996, Bioorganic & Medicinal Chemistry 4(1): 5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al., 1996, supra; Perry-O'Keefe et al., 1996, Proc. Natl. Acad. Sci. USA 93: 14670-675.

PNAs can, for example, be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras can be generated which may combine the advantageous properties of PNA and DNA. Such chimeras allow DNA recognition enzymes, e.g., RNAse H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup, 1996, supra). The synthesis of PNA-DNA chimeras can be performed as described in Hyrup, 1996, supra, and Finn et al., 1996, Nucleic Acids Res. 24(17):3357-63. For example, a DNA chain can be synthesized on a support using standard phosphoramidite coupling chemistry and modified nucleoside analogs. Compounds such as 5'-(4-methoxytrityl)amino-5'-deoxy-thymidine phosphoramidite can be used as a link between the PNA and the 5' end of DNA (Mag et al., 1989, Nucleic Acids Res. 17:5973-88). PNA monomers are then coupled in a stepwise manner to produce a chimeric molecule with a 5' PNA segment and a 3' DNA segment (Finn et al., 1996, Nucleic Acids Res. 24(17):3357-63). Alternatively, chimeric molecules can be synthesized with a 5' DNA segment and a 3' PNA segment (Peterser et al., 1975, Bioorganic Med. Chem. Lett. 5:1119-11124).

In other embodiments, the oligonucleotide may include other appended groups such as peptides (e.g., for targeting host cell receptors in vivo), or agents facilitating transport across the cell membrane (see, e.g., Letsinger et al., 1989, Proc. Natl. Acad. Sci. USA 86:6553-6556; Lemaitre et al., 1987, Proc. Natl. Acad. Sci. USA 84:648-652; International Publication No. WO 88/09810) or the blood-brain barrier (see, e.g., International Publication No. WO 89/10134). In addition, oligonucleotides can be modified with hybridization-triggered cleavage agents (see, e.g., Krol et al., 1988, Bio/Techniques 6:958-976) or intercalating agents (see, e.g., Zon, 1988, Pharm. Res. 5:539-549). To this end, the oligonucleotide may be conjugated to another molecule, e.g., a peptide, hybridization triggered cross-linking agent, transport agent, hybridization-triggered cleavage agent, etc.

Another aspect of the invention is a method to identify compounds that are able to modulate the expression or activity of the cancer-associated variant of glucose transporter 8, which can be used to prevent or treat cancer.

In one embodiment of the invention, the method for identifying a compound for ability to prevent or treat cancer comprises the steps:

(a) contacting a cell expressing a cancer-associated variant of glucose transporter 8 with a test compound; and (b) determining the expression or function of the cancer-associated variant of glucose transporter 8;

(c) comparing the expression or function of the cancer-associated variant of glucose transporter 8 to a control, wherein a decrease in expression or function of the cancer-associated variant of glucose transporter 8 as compared to the control is indicative of a compound useful to prevent or treat cancer.

The following non-limiting examples are illustrative of the present invention:

EXAMPLES

Example 1

Generation of VB1-050 Monoclonal Antibody

The VB1-050 monoclonal antibody was generated from pooled lymphocytes of cancer patient samples. SHFP-1 was used as the fusion partner to generate the monoclonal antibody. VB1-050 is an IgG1, kappa monoclonal antibody.

Example 2

Sequencing

Messenger RNA (mRNA) was isolated from hybridoma cells and first strand complement DNA (cDNA) was synthesized. The cDNA was then used to isolate antibody H and L chain genes by PCR. PCR primers were designed (see note) according to the consensus framework regions of the H (Gamma) and L (Kappa) chain isotypes. The PCR products were individually cloned into the TOPO-pCR 2.1 vector and transformed into *E. coli* cells. Individual clones containing the inserts in TOPO-pCR 2.1 were isolated and grown. Plasmid DNA was purified and sequenced.

```
Gamma Primers:
                                             (SEQ ID NO: 21)
1) 5' TCT AAA GAA GCC CCT GGG AGC ACA GCT CAT CAC
   CAT G 3'

                                             (SEQ ID NO: 22)
2) 5' GCC CGG GGA GCG GGG GCT TGC CGG CCG TCG CAC
   TCA 3'

                                             (SEQ ID NO: 23)
```

-continued

```
3) 5' ACC ATG AGT GAG AAA AAC TGG ATT TGT GTG
   GCA 3'

                                             (SEQ ID NO: 24)
4) 5' GGA GCC GGT GAC CAG GGT TCC CTG GCC CCA 3'

                                             (SEQ ID NO: 25)
5) 5' CTC ACC ATG GAG TTT GGG CTG AGC TGG GTT 3'

                                             (SEQ ID NO: 26)
6) 5' GGA GGC TGA GGA GAC GGT GAC CAG GGT TCC CTG
   GCC 3'

Kappa Primers:
                                             (SEQ ID NO: 27)
7) 5' GGC TCG AGA TGG ACA TGR RRD YCC HVG YKC ASC
   TT 3'

                                             (SEQ ID NO: 28)
8) 5' CCC GTC GAC CAT CAG ATG GCG GGA AGA T 3'

Note:
In order to isolate as many varieties as possible
using a single primer, mixed bases are used for
certain consensus primers: R = A + G, D = A + T +
G, Y = C + T, H = A + C + T, V = A + C + G, K =
T + G, S = C + G, W = A + T.
```

Each PCR reaction comprised the following components in a 50 μL reaction volume.

10×PCR buffer 5 μL
2 mM dNTPs 5 μL
50 mM MgCl2 2 μL
5' Primer 20 pmol.
3' Primer 20 pmol.
Taq DNA Polymerase 2.5 U
DNA template 50 ng The PCR cycling conditions were: 94° C. for 1 min., 62° C. for 1 min., 72° C. for 1.5 min. for 30 cycles and a final extension for 10 min. at 72° C. Amplified PCR products were electrophoretically separated on a 1% agarose gel, excised, purified using a Qiaquick gel extraction kit, cloned into the TOPO pCR 2.1 cloning vector and then DNA sequenced using the 373 DNA sequencer stretch (Griffin G. H. and Griffin M. A.: PCR technology, Current innovations. CRC Press, Boca. Raton. Fla. 3431 USA; Cloning vector pCR 2.1, Catalogue #205184. Invitrogen, Carlsbad, Calif.; Qiagen, Qiaquick gel extraction kit, Catalogue # 28706. Qiagen Inc., Mississauga, ON; and 373 DNA Stretch. PE Applied Biosystems, Mississauga ON.).

The CDR sequences for VB1-050 are shown in Table 1.

The light chain variable region and the heavy chain variable region are shown in FIGS. 1 and 2, respectively.

Example 3

Antibody Profiling by Measuring Tumor and Normal Cell Reactivity

VB1-050 was tested by flow cytometry for tumor and normal cell reactivity. A single panel of tumor cell lines representing fifteen different types of epithelial cancers was screened. The VB1-050 results are summarized in Table 2. Although VB1-050 had a MF value >2.0 for all indications, the strongest reactivity was observed, but not limited to, breast, melanoma, and ovarian cell lines. In comparison, reactivity with normal tissue cell lines was generally less than that seen with the cancer cell lines. In the case of the breast and prostate cell lines the expression of VB1-050 on average was >9-fold on the cancer cell lines. The two exceptions were the kidney and lung cell lines; however, they were still lower than the corresponding tumor cell type. MF value indicates the mean calculated from the sum of the mean fold increase in median fluorescence over the control antibody from all cell lines in each indication. A zero value indicates no measurable reactivity relative to the control antibody.

Example 4

Normal Tissue Microarray

VB1-050 was first tested against the flow positive tumor cell line SKBR-3 to assess the appropriate tissue format to demonstrate membrane staining and to define the optimal conditions for staining. VB1-050 demonstrated strong nuclear and/or nuclear membrane staining in all experimental groups. Of notice, the cytospin slides showed punctate staining on the cellular membrane, in about 30% of the intact cells. On frozen sections similar cellular membrane staining was detected (10% of cells) in addition to nuclear/nuclear membrane staining (60% of cells) as well as staining in the cytoplasm (10% of cells). On fixed-cell pellets, this antibody stained the nucleus and nuclear membrane (70% of cells), and cytoplasm (10% of cells), but very rarely stained the cell membrane (3-5% of cells). Since fixation did not affect the antigen (as evidenced by staining of fixed cells on cytospin slides) the apparent loss of cell membrane staining in the fixed cell pellet may be due to these cells having less surface area of the membrane as compared to the frozen cells. The greater membrane area visible in frozen cells is a consequence of shrinkage of the cytoplasm, as well as, by nature, a thicker section using frozen cells. Alternatively, processing after fixation (embedding, etc) may have altered the surface antigen.

Once the optimal staining conditions were identified, the antibody was tested in comparison with an isotype control (4B5) on a low density (LD) array of formalin-fixed critical normal for normal tissue reactivity. These results for VB1-050 are summarized in Table 3. No significant membrane staining of any of the normal critical tissues was observed. Intense staining of the nucleus and/or nuclear membrane was seen with many of the tissues. Similarly, consistent cell membrane staining was not seen with any of the non-critical normal tissues, except testes, which showed 30% membrane staining for ⅓ tested (Table 4).

Example 5

Tumor Tissue Microarray

In contrast to the critical and non-critical normal tissue screening, cell membrane reactivity was observed with some but not all of the tumor tissues. VB1-050 was more often detected in cancers of the colon, prostate, stomach, ovary and liver. The most intense staining (2+) was consistently detected in the gastric carcinomas. Generally, the percentage of cells with membrane staining varied with the indication and the tissue samples within each indication; however, carcinomas of the colon did show the highest percentage of cells being stained. See Table 5. No staining was detected in tissue specimens from lung, rectum skin and uterine cancers.

Example 6

Figure 3:
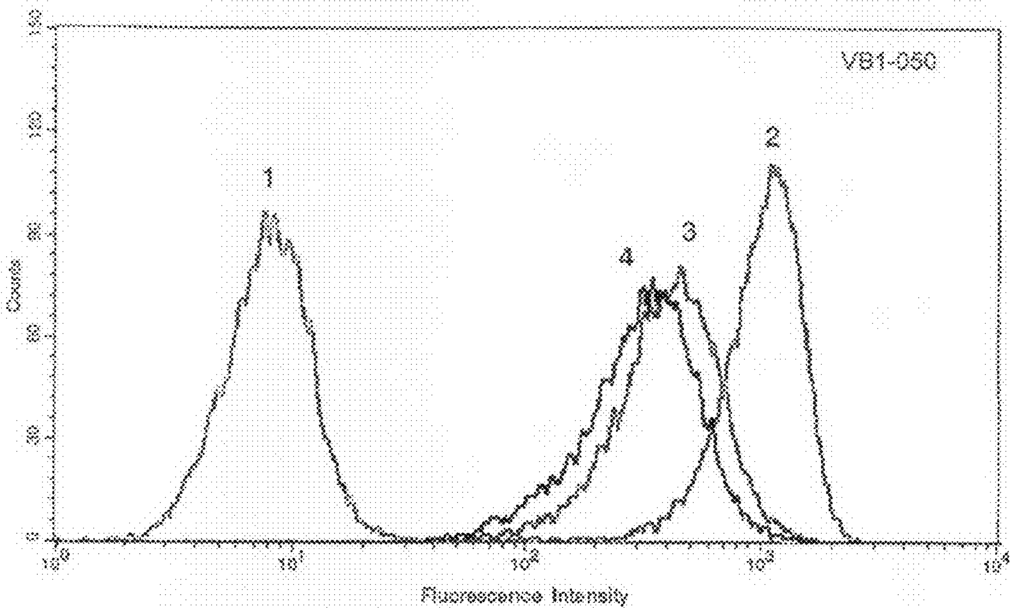
FIG. 3 demonstrates antibody cell surface binding after incubation of A-375 cells at different temperatures as determined by flow cytometry. Fluorescence labeling of A-375 cells after incubation of cell suspensions at 4° C.: 4B5 (1) and VB1-050 (2). Fluorescence labeling of A-375 cells after warming antibody-bound cells to 37° C.: VB1-050 for 60 min (3), for 120 min (4).

Assessment of VB1-050 Binding and Internalization by Flow Cytometry and Confocal Microscopy VB1-050 and two control antibodies (5E9 and MA-103) that demonstrate strong reactivity against the tumor cell line A-375 were used to assess VB1-050 for internalization. A representative experiment is shown in Table 6. VB1-050 binding results at different temperatures were not different from the internalizing antibody 5E9. After 60 min at 37° C., the membrane-bound VB1-050 disappeared from the cell surface, with a 61.8% reduction in median fluorescence. Increasing the incubation time at 37° C. was associated with a further decline in median fluorescence, but at a slower rate. By 120 min, the median fluorescence had decreased by 69.6%. Flow histograms demonstrating cell-surface binding are illustrated in FIG. 3.

Figure 4:
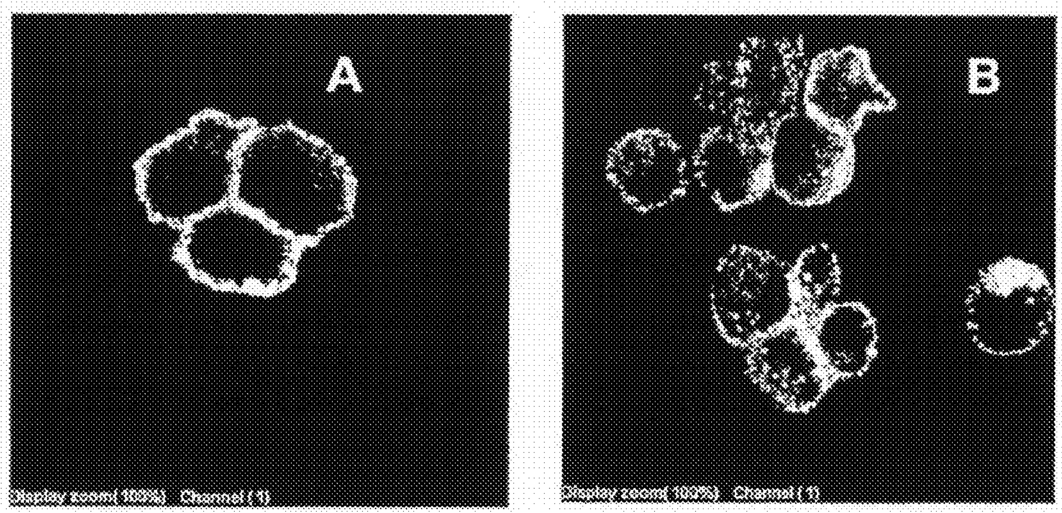
FIG. 4 shows confocal microscopy assessment of VB1-050 internalization. A-375 cells were incubated with antibody at 4° C., washed and warmed to 37° C. for 60 min. Cells were fixed, permeabilized and labeled with fluorescent-labeled second antibody. Fluorescence labeling of A-375 cells after incubation of VB1-050 at 4° C. for 60 min, displaying circumferential surface distribution of labeling, (60××4) magnification (A). Following incubation of antibody-bound cells at 37° C. for 60 min the cells show strong intracellular staining by internalized antibody, (60××4) magnification (B).

To confirm whether the cell-surface bound VB1-050 internalized into A-375 cells or was shed from the plasma membrane, antibody-treated cells were further evaluated by direct visualization of fluorescence distribution and intracellular staining with the aid of laser scanning confocal microscopy. Similarly to MA-103 and 5E9, VB1-050 incubation with A-375 cells at 4° C. for 60 min demonstrated a circumferential surface distribution of fluorescence label (FIG. 4A). Warming the VB1-050 antibody bound cells to 37° C. revealed strong intracellular staining by the internalized antibody within 60 minutes, as shown in FIG. 4B.

Example 7

Binding Affinity Status

The most important factor that influences the formation of antibody-antigen complexes is the affinity of the antibody for its antigen. This binding affinity is a constant property of these reactants and is expressed as an equilibrium constant (K) that is measured as a ratio of association/dissociation or KA/KD. For a given antibody, the difference in affinities observed relates more to the dissociation (KD) rather than association (KA), thus KD was chosen as a measure of affinity of VB1-050.

A flow cytometric approach was used to determine antibody affinity [Benedict, C. A. et al. (1997) "Determination of the binding affinity of an anti-CD34 single-chain antibody using a novel, flow cytometry based assay" J. Immunol. Methods 2001, 223-31]. Briefly, A-375 cells were incubated with a range of concentrations of VB1-050 in a sufficient amount of time to achieve equilibrium. The cells were then washed and treated with biotin conjugated anti-human IgG secondary antibody. The tumor cells were then analyzed by flow cytometry to detect cell bound antibody. The inverse of the determined median fluorescence was plotted as a function of the inverse of antibody concentration to determine KD by the Lineweaver-Burk method [Lineweaver, H. et al. (1934) "The determination of enzyme dissociation constants" J. Am. Chem. Soc. 56, 658].

The KD value of the interaction between VB1-050 and A-375 was determined to be $4.90\times10^{-8}$M.

Example 8

Engineering and Testing of a De-Bouganin Immunotoxin

1) Engineering of VB6-050

The PelB—$V_H$-PvuII insert, obtained from the digestion of the PelB—$V_{H845}$—$C_H$—F-de-bouganin/pSV73 plasmid with EcoRI and PvuII, was ligated into the PelB(—S)—$V_{H050}$—$C_H$—F-de-bouganin/psV73 vector pre-digested with the same enzymes (previously engineered for inclusion expression containing the PelB leader without the signal peptide sequence, PelB(—S)). 10F competent cells were transformed with the ligation reaction and selected on ampicillin plate. The screening of colonies by mapping restriction sites determined which clones contained the PelB—$V_{H050}$—$C_H$—F-de-bouganin insert.

The PelB(—S)—$V_{L050}$—$C_L$ fragment was digested with EcoRV and XhoI and ligated into the SpeI-de-bouganin-PelB—$V_{L845}$—$C_L$/psV73 vector pre-digested with the same enzymes. 10F competent cells were then transformed with the ligation reaction and plated onto LB-agar plates supplemented with ampicillin. The screening of colonies by mapping restriction sites determined which clones contained the SpeI-de-bouganin-PelB—$V_{L050}$—$C_L$ insert. The SpeI-de-bouganin-PelB—$V_{L050}$—$C_L$ insert was then cloned into the pING3302 plasmid using the EcoRI and XhoI restrictions sites. The PelB—$V_{H050}$—$C_H$—F-de-bouganin fragment was digested with EcoRI and SpeI and ligated to the SpeI-de-bouganin-PelB—$V_{L050}$—$C_L$/3302 vector pre-digested with the same enzyme creating VB6-050 insert. The plasmid containing the VB6-050 insert was then isolated and used to transform E104 cells.

2) Small-Scale Expression Studies

Transformed E104 cells containing VB6-050 were propagated in 30 mL of TB media (1% inoculum) in a 250 mL shake flask at 37° C. and shaken at 225 rpm for approximately 5 hours until the optical density (O.D. 600 nm) reached ~2. At this time, the culture was induced with a final concentration of 0.1% L-(+) arabinose and incubated at 25° C. for 16 hours. Subsequently, the supernatant was collected by centrifugation at 14000 rpm for 5 minutes and analyzed by Western blot using either an anti-lambda or an anti-human kappa light chain under non-reducing conditions to confirm the presence and size of the immunotoxin.

3) Master Cell Bank Generation

To generate the MCB, a single colony from an LB-agar plate containing 25 μg/mL of tetracycline was used to inoculate 5 mL 2×YT plus 25 μg/mL of tetracycline and incubated at 37° C. with constant shaking. When the $OD_{600}$ reached ~2, 50 mL of 2×YT medium containing 25 μg/mL of tetracycline in a 250 mL shake-flask was inoculated with 1.25 mL of the seed culture and incubated at 37° C. When the ($OD_{600}$ reached 1 to 1.5, 25 mL of 30% glycerol was mixed into the culture. Aliquots of 1.5 mL were placed in cryotubes and stored at −80° C. Three independent vials were tested for expression as described previously.

4) Fermentation and Purification

Fed batch fermentation of VB6-050 was performed in a 15 L CHEMAP fermenter using TB medium. At an $OD_{600}$ of 20 (mid-log), the culture was induced with a mixture of feed (50% glycerol) and inducer (200 g L-arabinose). At 30 hours post induction, the culture was harvested and centrifuged at 8000 rpm for 30 min, then purified using CM-sepharose and Chelating-sepharose columns followed by a size exclusion column. Briefly, the supernatant was concentrated and diafiltered against 20 mM sodium phosphate pH 6.9±0.1. The diafiltered concentrated supernatant was then applied onto a CM-sepharose column equilibrated with 20 mM sodium phosphate, 25 mM NaCl pH 6.9±0.1. The column was washed with 20 mM sodium phosphate, 25 mM NaCl pH 6.9±0.1. Bound VB6 Fab-de-bouganin fusion protein was subsequently eluted with 20 mM sodium phosphate, 150 mM NaCl pH 7.5±0.1. The CM-Sepharose eluate was adjusted to a final concentration of 0.25% triton-X100 and applied to a charged Chelating sepharose column. The Chelating-sepharose column was then washed with 3 different wash buffers starting with 20 mM sodium phosphate, 150 mM NaCl, 0.25% triton-X100 pH 7.5±0.1, followed by 20 mM sodium phosphate, 150 mM NaCl pH 7.5±0.1 and followed by 20 mM sodium phosphate, 150 mM NaCl, 10 mm imidazole pH 7.5±0.1. The bound VB6 Fab-de-bouganin fusion protein was eluted with 20 mM sodium phosphate, 150 mM NaCl, 250 mM imidazole pH 7.5±0.1 and collected in 2 mL fractions. The absorbance at $A_{280}$ nm was determined for each fraction and the fractions with material were pooled and applied onto a size exclusion column S200 in order to obtain a purity of ~80%. Samples at each step of the process were analyzed by Western blot using the anti-kappa antibody. Purity after the size exclusion column was confirmed by colloidal blue staining.

5) Biological Activity of the VB6-050

Human melanoma A-375, human T cell Daudi, human ovarian SK-OV-3, human pancreatic Panc-1, human breast SKBR-3 and MB-435S and human colon Colo-320 cell lines were grown in their respective media as per ATCC protocols. Cells were harvested at 30 to 40% confluency with viability greater than 90%.

a) Binding Activity

Flow cytometry was used to demonstrate that purified VB6-050 retain binding specificity using antigen-positive cell line SKBR-3, A-375 and SK-OV-3 and an antigen-negative cell line Panc-1, Colo-320 and Daudi, respectively. Binding was detected using an anti-de-bouganin antibody. Briefly, constructs to be tested were incubated with $0.45\times10^6$ tumor cells for 1.5 hours on ice. After washing, cell surface bound reactivity was detected with rabbit anti-de-bouganin (1/100) for an hour on ice. The cells were washed and incubated with FITC-conjugated anti-rabbit IgG for 30 minutes on ice. Subsequently, the cells were washed, resuspended in PBS 5% FCS containing propidium iodide for assessment of Fab binding by flow cytometry.

b) Competition Assay

A saturation curve was generated by incubating antigen positive cell with an increased concentration of VB6-050 ranging from 10 to 750 μg/mL. The bound Fab-de-bouganin was detected by flow cytometry as described previously. The concentration of Fab-de-bouganin corresponding to the saturation point was then incubated with antigen-positive cells in presence of increased concentrations of parental IgG antibody. The reduction of bound Fab-de-bouganin was measured by flow cytometry. The 4B5 IgG was used as a negative control.

c) Cytotoxicity Assay

The cytotoxicity of VB6-050 was measured by an MTS assay. Briefly, antigen-positive and antigen-negative cells were seeded at 1000 cells per well and incubated at 37° C. for 3 hours. Subsequently, varying concentrations of VB6-050 and de-bouganin were added to the cells and after 5 days, the cell viability determined.

Results

1) Engineering and Small-Scale Expression of VB6-050 in pING3302 Expression Vector As a first attempt to produce Fab-de-bouganin protein, the vector was engineered as two separate constructs, the Fd portion fused to de-bouganin and the light chain. The expression of each chain was directed into inclusion bodies by the deletion of the peptide signal in the PelB leader sequence, PelB(—S). However, the lack of expression of the Fd-de-bouganin protein into inclusion bodies and the success of the VB6-845 soluble expression rationalized the re-engineering of VB6-050 soluble Fab-de-bouganin construct. In order to minimize the time of re-engineering and based on feasibility, restriction enzymes were used to link the Fd-F-de-bouganin and $V_L$—$C_L$ fragments to the PelB leader sequence with a peptide signal.

Figure 5:
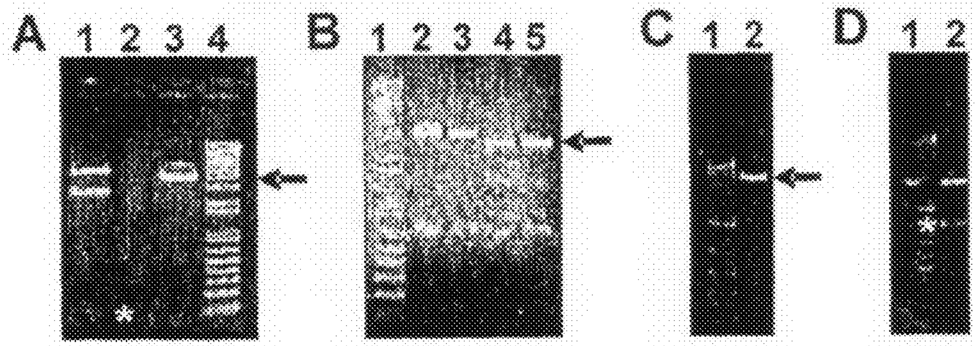
FIG. 5 shows an agarose gel of the PCR reaction. The DNA was detected using ethidium bromide under a UV lamp. A) The PelB—$V_{H845}$—$C_H$—F-de-bouganin/psV73 plasmid and PelB(—S)—$V_{H050}$—$C_H$—F-de-bouganin/pSV73 were digested with EcoRI and PvuII and loaded on lane 1 and 3, respectively. The * symbol indicates the EcoRI-PelB-PvuII insert with the peptide leader sequence which was ligated to the PelB(—S)—$V_{H050}$—$C_H$—F-de-bouganin/pSV73 predigested (indicated with the arrow) to create the PelB—$V_{H050}$—$C_H$—F-de-bouganin/pSV73. B) The PelB—(S)—$V_{L050}$—$C_L$/pSV73 and SpeI-de-bouganin-PelB—$V_{L845}$—$C_L$/pSV73 plasmid were digested with EcoRV and XhoI and loaded on lanes 2-3 and 4-5, respectively. The insert and the vector indicate with the * symbol and the arrow, respectively were used to create the SpeI-de-bouganin-PelB—$V_{L845}$—$C_L$/pSV73 plasmid which was subsequently inserted into the 3302 plasmid. C) The SpeI-de-bouganin-PelB—$V_{L845}$—$C_L$/3302 plasmid and D) PelB—$V_{H050}$—$C_H$—F-de-bouganin insert, digested with EcoRI and SpeI (indicated with the arrow and the * symbol, respectively) and loaded on lane 2 were ligated to create VB6-050/3302.

The analysis of the Fd and light chain of 050 showed that the restriction sites EcoRI and PvuII and EcoRV and XhoI located in the heavy and light chain, respectively, allowed the re-engineering of VB6-050 without PCR reaction using the VB6-845 intermediate constructs. To that end, the PelB insert with the leader peptide of the PelB—$V_{H845}$—$C_H$—F-de-bouganin was obtained using the restriction sites EcoRI and PvuII and ligated into the PelB(—S)—$V_{H050}$—$C_H$—F-de-bouganin pre-digested with the same enzyme (FIG. 5A). Similarly, the PelB(—S)—$V_{L050}$—$C_L$/pSV73 plasmid was digested with EcoRV and XhoI and the insert cloned into the SpeI-de-bouganin-PelB—$V_{L845}$—$C_L$, vector pre-digested with EcoRV and XhoI. The insert, PelB—$V_{L050}$—$C_L$, was subsequently inserted into the 3302 plasmid using the EcoRI and XhoI restriction sites (FIG. 5B). The PelB—$V_{H050}$—$C_H$—F-de-bouganin fragment then ligated via the EcoRI-SpeI restriction sites generating the VB6-050 insert into the 3302 DNA plasmid which was transformed into E104 cells (FIGS. 5C and 5D).

Figure 6:
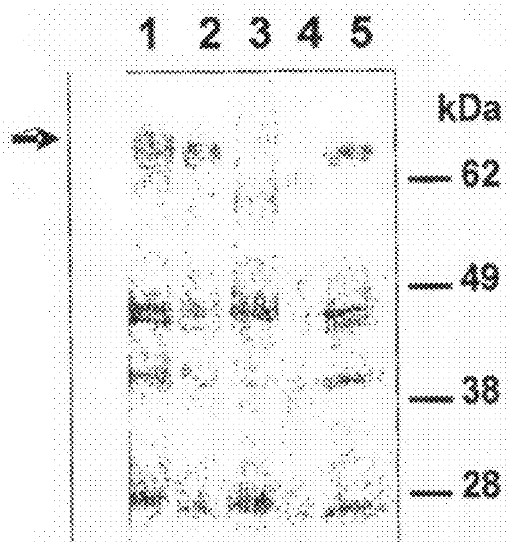
FIG. 6 shows a Western blot of VB6-050. A representative supernatant of VB6-845 (lane 1) and VB6-050 (lane 2) was loaded under non-reducing conditions on a SDS-PAGE gel and immunoblotted with an anti-human Kappa light chain-HRP antibody (1/1000). Lanes 3 and 4 correspond to the supernatant of a non-induced culture and the ladder, respectively. Lane 5 is VB6-845 supernatant previously tested positive on Western blot.

The Western blot analysis under non-reducing conditions of VB6-050 showed that the full-length proteins are detected with the anti-Kappa light chain antibody (FIG. 6). In addition, the level of expression of VB6-050 is similar to the VB6-845 used as a reference. Western blotting of non-induced E104 culture supernatant revealed no corresponding bands suggesting that these proteins are specifically detected with the corresponding antibody (FIG. 6, lane 4). In addition a similar profile of degraded products observed in the VB6-845 was also obtained with each clone.

2) Purification of VB6-050

Figure 7:
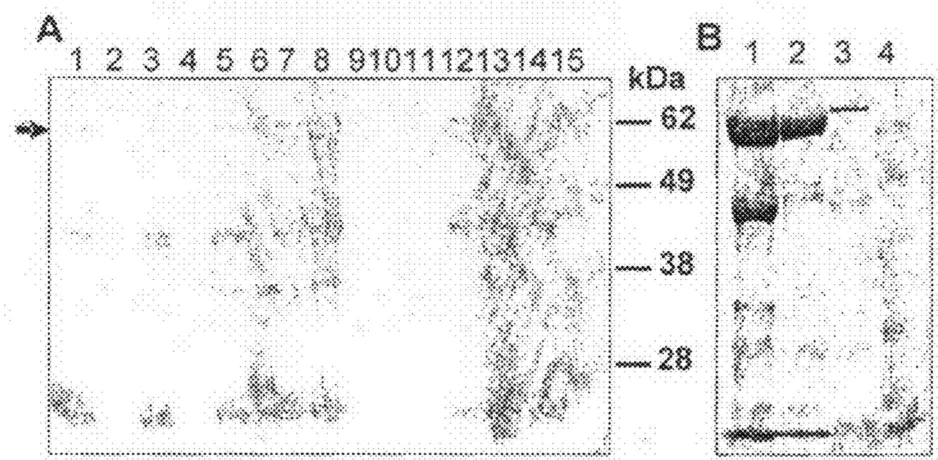
FIG. 7 shows a Western blot of a representative purification of VB6-050 from E104 supernatant. A) Samples, 16 μL, taken at different steps of the purification process were immunoblotted using anti-human Kappa light-HRP antibody. The arrows indicate intact product. Lane 1: Culture supernatant; lane 2: Permeate of the concentrated supernatant; lane 3: Concentrated supernatant 1/10 diluted; lane 4: Permeate of the diafiltered concentrated supernatant; lane 5: Diafiltered concentrated supernatant 1/10; lane 6: Flow-through of the CM-sepharose column; lane 7: Wash of the CM-sepharose column; lane 8: Eluate of the CM-sepaharose column or Ni-sepharose starting material; lane 9: Flow-through of the Ni-chelating column; lanes 10, 11 and 12: Different step washes of the Ni-chelating column; lane 13: Eluate of the Ni-chelating-Sepharose or SEC-200 starting material; lane 14: Pool of the SEC-200 fractions 26-28; lane 15: Ladder and VB6-845 as a control. B) Coomassie staining of VB6-050. Lane 1: SEC-200 starting material; lane 2: fraction 27; lane 3: purified VB6-845; lane 4: ladder.

VB6-050 was purified from a 15 liter fermentor. Aliquots from each steps of the purification process were analyzed on Western blot in order to assess the recovery rate of each column (FIG. 7A). The immunoblot was incubated with an anti-human Kappa light chain. No detectable product was observed in the permeate of the concentration and diafiltered step (FIG. 7A, lane 2 and 4, respectively). The diafiltered material, diluted 1/10, was loaded on the CM-sepharose column (FIG. 7A, lane 5). Western blot analysis showed that the CM eluate (FIG. 7A, lane 8) contains the full-length VB6-050 and possible degraded VB6-050 fragments. The flow-through of the nickel column, lane 9, shows that most of the VB6-050 and other products bound to the column. The $Ni^{2+}$ eluate, lane 13, was then applied on a SEC 200 size exclusion allowing the separation of the intact VB6-050 from the degraded fragments (FIG. 7A, lane 14 and FIG. 7B, lane 2).

3) Detection of VB6-050 Proteins Binding by Flow Cytometry

Figure 8:
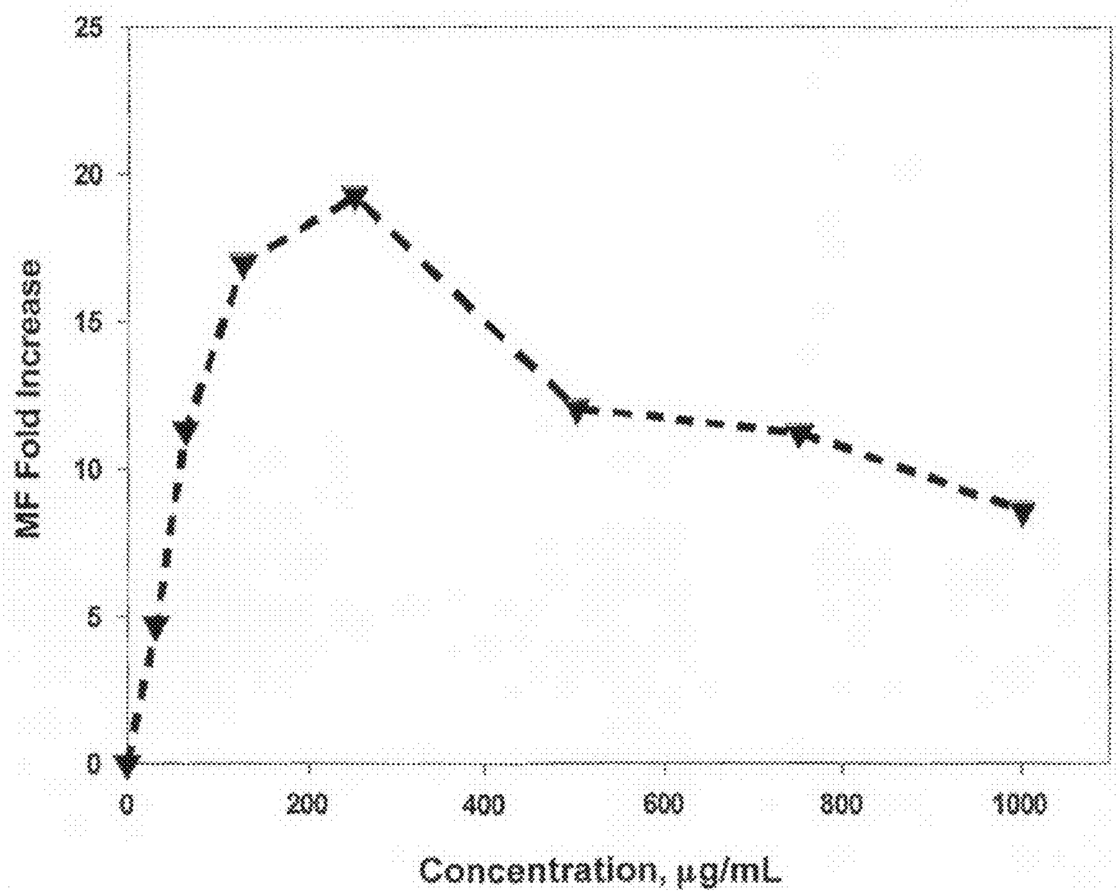
FIG. 8 shows the titration curve of VB6-050. SKBR-3, A-375 and SK-OV-3 cells were incubated with various concentrations of VB6-050 and the medium fluorescence was obtained by flow cytometry. The Median Fluorescence (MF)

For VB6-050, antigen-positive and antigen-negative cell lines were selected based on the profiling data of each antibody. The bound Fab-de-bouganin was detected by flow cytometry using anti-bouganin antibody. As expected, no binding was detected by flow cytometry after incubation with the antigen-negative cell. In contrast, bound Fab-de-bouganin was detected with the antigen-positive cell lines. In addition, the antigen positive cell line was incubated with various concentrations of Fab-de-bouganin protein, ranging from 0 to 500 μg/mL, and the binding activity was determined by flow cytometry. A titration curve was generated (FIG. 8). The inverse of the determined median fluorescence was plotted as a function of the inverse of antibody concentration to determine the $K_D$ by Lineweaver-Burk method. A straight line was generated and the $K_D$ was calculated from the slope of the curve. The dissociation constant $K_D$ were determined by the following equation: 1/F=1/fmax+(KD/Fmax)(1/VB6), where F=background subtracted median fluorescence and Fmax was calculated from the plot (Table 7). The saturation point for the Fab-de-bouganin was determined from the saturation curve and used for the competition assay with the parental antibody. The VB6-050 saturation point, 250 μg/mL, was incubated with antigen-positive cells in presence of increasing amount of its corresponding parental IgG ranging from 0 to 1000 μg/mL. The bound VB6-050 was detected by flow cytometry using anti-bouganin antibody. As expected, the parental IgG competed the binding of the Fab-de-bouganin proteins. The concentration of IgG required to inhibit 50% of bound Fab-de-bouganin was determined to be 180 μg/mL (Table 7).

4) Cytotoxicity of VB6-050 Proteins

The negative and positive-antigen cell lines were incubated with different concentrations of VB6-050 from 1 nM to 1 μM. After 5 days incubation, the calculated $IC_{50}$ of VB6-050 was 400 nM (FIG. 9) (Table 7). In contrast, no $IC_{50}$ could be determined with the antigen negative cell lines.

Conclusion

The VB1-050 IgG, selected from the Hybridomics and Immunomine™ platform was engineered as soluble Fab-de-bouganin fusion protein which contains de-bouganin genetically linked to the $V_H$—$C_H$ domain via the furin cleavable linker. The data confirms that the Fab-de-bouganin format derived of IgG is suitable for soluble expression leading to an easy downstream process. Once purified, the flow cytometry data showed that the profiling data of the VB6 format matched the parental IgG suggesting the specificity and selectivity was preserved. In addition, the IgG competed with the VB6 fusion proteins demonstrating that both fragments bound to the same antigen. The calculated affinity of the VB6 format was in the micromolar range leading to $IC_{50} \geqq$ to 280 nM.

Example 9

Antigen Identification

Preliminary Characterization of VB1-050 Ag

VB1-050 showed a 58.62% (P-value 0.008) increase in binding upon deglycosylation. This increase in the binding of the antigen observed upon deglycosylation, suggests that the glycan moiety may partially mask the antigenic sites on the cell surface and that deglycosylation may be an essential step in the identification of the antigen.

Immunoprecipitation

Equal amounts of membrane preparations from each of the four positive cell lines, MCF-7, MDA-MB-435S, A-375, HepG2, and three negative cell lines, Panc-1, Daudi and C-33A were deglycosylated with N-Glycanase and nutated with 40 μg VB1-050 and 4B5-IgG each in the presence of protease inhibitors with conditions mimicking in-vivo conditions. Immune complexes were centrifuged, washed with RIP-A lysis buffer and eluted with 0.2M glycine pH 2.5.

Gel-Based Analysis and Western Blotting

Immunoprecipitates from all the above-mentioned cell lines were subjected to reducing and non-reducing conditions of sample preparation and were subsequently analyzed by SDS-PAGE and Western blotting. The resulting blots were probed with 4B5-IgG and VB1-050 simultaneously and corresponding secondary antibody conjugated to HRP, to visualize the immunoprecipitated proteins by chemiluminescence. A single band was detected at −50 kDa from VB1-050 immunoprecipitates on 1D-PAGE in all the cell lines and 2D-PAGE did not yield any result. No bands were detected with 4B5-IgG. Since the conventional approach did not show any differentially expressed antigen, an alternative method for antigen identification was explored.

HIP-Antigen ID Using ProteomeLab™ PF-2D in Tandem with Nano-ESI-MS/MS

PF2D Fractionation of HepG2, MCF-7, Panc-1 and C-33A

The pre-fractionated VB1-050 immunoprecipitates from membrane preparations were clarified of all particulate material by high speed centrifugation. The clear supernatant was equilibrated with Start buffer and fractionated on the chromatofocusing column in the first dimension. The peak fractions eluting at pH=7.4-7.6 was equilibrated with solvent A (0.1% TFA) in the ratio of 1:4, and fractionated on the HPRP column with a gradient of 0-100% acetonitrile containing traces of TFA.

HepG2 and MCF-7 upon fractionation on the chromatofocusing column (CF), showed a single broad peak eluting. at pH 7.4-7.6 as two fractions (constituting # B6 and B7) at 68 and 65 minutes, respectively. As observed in FIGS. 10A and B, HepG2 and MCF-7 membranes eluting off the HPRP column showed different separation profiles, entirely dependent on the presence of the VB1-050 reactive antigens. Two peaks were observed to be differentially regulated in the positive cell lines, that seemed to be negligible or totally absent in the negative cell lines, Panc-1 and C-33A membranes (FIGS. 10A and B). On thorough analysis of the protein peaks present in the positive cell line (MCF-7 and HepG2), it was shown that the peaks elute from the RP-HPLC column with retention times of 15 and 18 minutes, respectively. These peaks were not observed in the antigen-negative cell lines (Panc-1 and C-33A). Instead, a single peak eluting slightly earlier at 12 minutes was observed in the negative cell lines.

Fractionation Analysis Using ProteoVue™/DeltaVue™ software

The chromatographic profiles obtained for the HPRP column were imported into ProteoVue™ files to be formatted into an acceptable format for the final analysis on DeltaVue™. The analyses were combined for the antigen fractionation from both positive (HepG2 and MCF-7) and negative (Panc-1 and C-33A) cell lines and formatted using ProteoVue® software to generate a comprehensive membrane protein map from each of the cell lines. A comparative profiling of differentially regulated proteins was thereafter generated on the DeltaVue™ software. The chromatographic profiles of the fractionation from both cell lines were converted from peaks to banding patterns making areas of differential expression more readily visible. Particular differentially expressed peaks/bands in the positive cell line could be focused for better resolution and analysis. Overlaying the positive and negative plots obtained in each experiment showed that the over-expression of proteins was seen only in the positive cell lines (HepG2 and MCF-7) and these fractions were used for peptide extraction purposes.

Peptide Extraction from Peak Fractions

Tryptic digestions were performed with sequencing grade trypsin in a 20-hour peptide extraction process finally resulting in the extraction of peptides that were analyzed on a QSTAR Pulsar-I (ESI-qTOE-MS/MS), equipped with a nanosource with a working flow rate of 20-50 nL/min. The peptides ionize and are detected as doubly, triply or quadruply charged molecules which are then refined to their respective masses. De-novo sequencing of the identified proteins was also performed whenever possible. Peptides were extracted from both positive and negative cell lines to ensure it was the right antigen. Peptide masses extracted from the mass spectra were used directly to identify the antigen according to the MOWSE scores obtained on protein databases that are accessible through the MASCOT search engine.

Peptides were extracted post-tryptic digestion from the peak, fractions eluting at 15-18 minutes, from all four samples (MCF-7, HepG2, Panc-1 and C-33A) and subjected them to MS analysis. In addition to fractions eluting at 15, 18 minutes, fractions eluting at the 12$^{th}$ minute from positive and negative cell lines were also processed simultaneously. FIGS. 11-14 show results of the TOF-MS scans of the peptides obtained from the cell lines. As seen in FIG. 15, one single protein was identified corresponding to glucose transporter-8 from both the positive cell lines that was undetectable in the negative cell lines. The difference in elution between the two peaks (15 vs 18 minutes) could be attributed to changes in glycosylation or other post-translational modifications.

Mass Spectral Analysis

Peptide analysis was done in two ways:

All the peptides recovered and reconstructed to their right masses were used directly in a peptide mass fingerprinting step to obtain an ID for the protein.

Peptides that were abundant and well ionized were chosen for further MS/MS ion fragmentation, wherein, the 'y' and 'b' ions were used to deduce their primary structure. These sequences were then searched for homologies in the protein database for protein ID.

Peptides ionize and are detected as doubly, triply or quadruply charged molecules, on a LC-MS/MS system as opposed to detection as singly charged on Matrix assisted ionization such as in MALDI. Differentially charged peptides were thereafter refined to their respective masses, in the mass reconstruction step. These peptide masses were then directly analyzed by a matrix science based mascot search engine for antigen ID. Peptide masses extracted from the mass spectra were used directly to identify the antigen according to the MOWSE scores obtained on protein databases that are accessible through search engines such as MASCOT, SEQUEST, and Prospector. Since the QSTAR-pulsar-I purchase includes the purchase of license from Pepsea server for most recent protein database additions, and is compatible with MASCOT, this search engine was selected for all protein searches.

The list of peptides recovered and their mapped positions to the sequence from Glucose Transporter 8 are as given in FIGS. 15, 16 and Table 8. All peptides represented were obtained by de novo sequencing. FIG. 17 identifies Glucose Transporter 8 as the antigen.

MS/MS fragmentation of four of the peptides (1401.54-466.600000, 3+; 1070.785448-536.400000, 2+; 1998.272862-667.098230, 3+; 1176.185448-589.100000, 2+) gave rise to the fragment ions shown in FIGS. 18-21 that mapped to peptides from Glucose Transporter 8. Since these 2 peptides were all detected in TOF-MS, these peptides were used for MS/MS ion fragmentation apart from the peptides derived from mass fingerprinting. A discrete nanospray head installed on a nanosource was used for the purpose. The collision energy was 48V, curtain gas and CAD gas were maintained at 25 and 6, respectively, and the sample allowed to cycle for 1.667 minutes (100 cycles) to obtain stable mass ion fragmentation. Peptides derived from the spectra clearly matched the sequence on Glucose Transporter 8, therefore were pulled down as major hits. The ion fragmentation data further confirm the identity of Glucose Transporter 8 as the cognate antigen for VB1-050.

Peptide mass fingerprinting and MS/MS fragmentation of the antigen-positive fractions revealed the identity of Glucose transporter-8/GLUTX1/SLC 2A8 gene product as the cognate binding antigen for VB1-050. Glucose transporter-8 is a ~50 kDa type-II transmembrane protein, with N-terminus inside the cell. 34% sequence coverage was obtained from the peptides that were recovered in-house. Cell lines selected positive by flow show the presence of the antigen upon immunoprecipitation. MS/MS analysis of two peptides, 1070.785, appearing as a doubly charged molecule (536.40000, 2+); 1401.54, appearing as a triply charged molecule (466.60000, 3+), identified two peptide sequences, SLASVVVGVIQ (SEQ ID NO:20 (292-303) and KTLEQITAHFEGR (SEQ ID NO:19) (466-477), respectively, clearly matched the protein sequence corresponding to Glucose transporter-8.

MS/MS sequencing of two additional peptides recovered from MCF-7, 1176.3547 and 1997.9992, mapped sequences with 68.2% homology to corresponding peptides from GLUT8 with changes in amino acids at seven positions, i.e., 7, 10, 12-15, 18. The changes incorporated correspond to the positional changes at 12, 13 from LL to AA as reported by Shin et al. (2004, J. Neuro. Res. 75: 835), that is responsible for the orientation of GLUT8 from cytosol to the plasma membrane.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE 1

CDR Sequences

| CDR Sequences | VB1-050 | | | |
|---|---|---|---|---|
| | L-chain | | H-chain | |
| CDR1 | RASQDISNYLA | SEQ ID NO: 1 | NYAMS | SEQ ID NO: 4 |
| CDR2 | AASSLHS | SEQ ID NO: 2 | AITPSGGSTNYADSVKG | SEQ ID NO: 5 |
| CDR3 | LQYSTYPIT | SEQ ID NO: 3 | VPYRSTWYPLY | SEQ ID NO: 6 |

TABLE 2

Comparison of tumor and normal cell surface reactivity with VB1-050

| Clinical Indication | Representative Tumor Cell lines | N[1] | MF[2] | Relative Rank |
|---|---|---|---|---|
| Breast | MCF-7[c], MDA-MB-231[d], MDA-MB-435S[a] | 3 | 29.9 | 1 |
| Melanoma | A-375, SK-MEL-5[a,b], SK-MEL-28[a] | 3 | 22.7 | 2 |
| Ovarian | SK-OV-3[a], OVCar-3 | 2 | 21.7 | 3 |
| Prostate | DU-145[a,b,f], PC-3[a,b,g], LNCaP[a,b,g] | 3 | 19.6 | 4 |
| Kidney | Caki-1[a], A498[a], ACHN[a] | 3 | 18.4 | 5 |
| Rectum | Sw837, NCI-H630 | 2 | 15.2 | 6 |
| Lung | A-549, NCI-H460, NCI-H69 | 3 | 14.8 | 7 |
| Liver | SK-HEP-1, Hep-G2 | 2 | 14.6 | 8 |
| Colon | HT-29[a], SW480, WiDr | 3 | 13.3 | 9 |
| Cervix | HeLa, C-41, C-33A | 3 | 11.8 | 10 |
| Head & Neck | SCC-15, SCC-25 | 2 | 11.4 | 11 |
| Bladder | UM-UC-3, T24 | 2 | 9.8 | 12 |
| Stomach | AGS, NCI-N-87, KATO III | 3 | 9.6 | 13 |
| Pancreas | PANC-1, BxPC-3, MIA PaCa-2 | 3 | 7.6 | 14 |
| Endometrium | RL-95-2, HEC-1-A | 2 | 7.0 | 15 |
| Normal Cell Type | Cell Line | | | Tumor normal |
| Kidney | HRE | 1 | 12.5 | 1.5 |
| Lung | NHLF | 1 | 8.7 | 1.7 |
| Endothelial | HUVEC | 1 | 5.0 | N/A |
| Breast | HMEC | 1 | 3.1 | 9.6 |
| Prostate | PrEC | 1 | 2.1 | 9.3 |

[1]N indicates the number of cell lines tested per indication. [2]MF: Values indicate the mean calculated from the sum of the mean fold increase in median fluorescence over the control antibody from all cell lines in each indication. A zero value indicates no measurable reactivity relative to the control antibody.

[a]Indicates orthotopic models offered by AntiCancer Inc.

[b]Indicates cell lines available as GFP (green fluorescent protein)-transfectants.

[c]Her2/neu$^-$, ER$^+$.

[d]Her2/neu, ER$^-$, p53$^{wt}$, ras$^{wt}$.

[e]Her2/neu$^-$, ER$^-$, p53$^{mt}$, ras$^{wt}$.

[f]Androgen-responsive.

[g]Androgen-unresponsive.

TABLE 3

LD Array of Formalin-Fixed Critical Normal Tissue for VB1-050

| Tissue | Membrane Staining | Score Range[1] |
|---|---|---|
| Brain | None (0/6) | 0 |
| Colon[2] | None (0/4) | 0 |
| Heart | None (0/5) | 0 |
| Kidney | None (0/3) | 0 |
| Liver | None (0/5) | 0 |
| Lung | None (0/4) | 0 |
| Pancreas | None (0/4) | 0 |
| Stomach[3] | None (0/4) | 0 |

[1]Scoring was evaluated on a 0-3+ scale, with 0 = no staining and trace being less than 1+ but greater than 0. Grades 1+ to 3+ represent increased intensity of staining, with 3+ being strong, dark brown staining. In general, a single specimen of 6 different patients was screened. Where fewer than 6 patients were screened indicates cores were either missing or were not representative of the tissue to be stained. Values in parentheses indicate the percentage of cells stained in the scored range.

[2]Only adjacent normal tissues were used.

[3]Four of five were adjacent normal tissue specimens.

TABLE 4

HD Formalin-Fixed Normal TMA for VB1-050

| Tissue | Membrane Staining | Score Range* |
|---|---|---|
| Adrenal | None (0/5) | 0 |
| Aorta | None (0/5) | 0 |
| Artery | None (0/5) | 0 |
| Bladder | None (0/5) | 0 |
| Brain | None (0/5) | 0 |
| Breast | None (0/5) | 0 |
| Fallopian tube | None (0/5) | 0 |
| LN | None (0/4) | 0 |
| Muscle | None (0/5) | 0 |
| Ovary | None (0/5) | 0 |
| Pituitary | None (0/5) | 0 |
| Placenta | None (0/5) | 0 |
| Prostate | 0/5 | 0 |
| Skin | 0/1 | |
| Spinal cord | None (0/3) | 0 |
| Spleen | None (0/5) | 0 |
| Testis | 1/5 | 1+ (30%) |

TABLE 4-continued

HD Formalin-Fixed Normal TMA for VB1-050

| Tissue | Membrane Staining | Score Range* |
|---|---|---|
| Thymus | None (0/1) | 0 |
| Thyroid | None (0/5) | 0 |
| Ureter | 0/2 | 0 |
| Uterus | None (0/3) | 0 |

*Scoring was evaluated on a 0-3+ scale, with 0 = no staining and trace being less than 1+ but greater than 0. Grades 1+ to 3+ represent increased intensity of staining, with 3+ being strong, dark brown staining. In general, 2 specimens of 8 different patients were screened. Where fewer than 8 patients were screened indicates cores were either missing or were not representative of the tissue to be stained. Values in parentheses indicate the percentage of cells stained in the scored range.

TABLE 5

HD Formalin-Fixed Tumor TMA for VB1-050

| Tissue | Membrane Staining | Score Range |
|---|---|---|
| **Bladder** | 2/8 | 2+ (50%) |
| **Breast** | 1/8 | 1+ (90%) |
| **Cervix** | 1/8 | 1+ (30%) |
| **Colon** | 4/7 | 1+ (70-90%) |
| **Kidney** | 1/8 | 2+ (40%) |
| **Liver** | 3/6 | 1+ (80%) |
| Lung | 0/6 | N/A |
| **Ovary** | 3/7 | 1+ (20%) |
| **Pancreas** | 2/8 | 2+ (30-80%) |
| **Prostate** | 4/7 | 1+ (20-60%) |
| Rectum | 0/7 | N/A |
| Skin | 0/4 | N/A |
| **Stomach** | 4/8 | 2+ (30%) |
| Uterus | 0/8 | N/A |
| **Head & Neck** | 2/8 | 2+ (30-50%) |

Scoring was evaluated on a 0-3+ scale, with 0 = no staining and trace being less than 1+ but greater than 0. Grades 1+ to 3+ represent increased intensity of staining, with 3+ being strong, dark brown staining. In general, 2 specimens of 8 different patients were screened. Where fewer than 8 patients were screened indicates cores were either missing or were not representative of the tissue to be stained. Head & neck cancers included carcinomas of the throat, lip, larynx, mouth, tonsil, and gingival surface. Values in parentheses indicate the percentage of cells stained in the scored range. Cancer indications that are bolded indicate VB1-050 reactivity.

TABLE 6

Flow cytometry assessment of antibody binding as a function of time and temperature

| MAb ID | Antibodies | Incubation (min) at 37° C. | Median Fluorescence (MF) | Fold-increase in MF | % Reduction in MF |
|---|---|---|---|---|---|
| VB1-050 | VB1-050 | —[4] | 1041.0 ± 23.0 | 129.1 | — |
| | | 60 | 397.5 ± 5.1 | 49.2 | 61.8 |
| | | 120 | 317.5 ± 4.1 | 39.3 | 69.6 |
| Non-Internalizing Control | MA-103 | — | 536.1 ± 31.3 | 112.8 | — |
| | | 120 | 535.5 ± 16.8 | 113.0 | — |
| Internalizing Control | 5E9 | —[4] | 246 ± 11 | 60.0 | — |
| | | 60 | 53.5 ± 1.5 | 13.0 | 78.3 |
| | | 120 | 48 ± 4 | 11.7 | 80.5 |

[1]A representative experiment is shown.

[2]MF increase above the negative control, mouse myeloma IgG or human IgG (4B5).

[3]Percent reduction of MF from the cell-surface of tumor cells.

[4](—) cells incubated on ice for 120 minutes.

TABLE 7

| Biological characterization of VB6-050 | | | | |
|---|---|---|---|---|
| | Affinity (M) | VB6 Saturation conc. (μg/mL) | IgG concentration (μg/mL)* | $IC_{50}$ (nM) |
| VB6-008 | $1.4.10^{-8}$ | ND | ND | 280 |

ND: not determined

*Concentration of IgG that inhabits 50% of the VB6 binding.

TABLE 8

| Observed | Start | End | Peptide | SEQ ID NO |
|---|---|---|---|---|
| 1998.27 | 3 | 22 | PEDPSETEPAAPRPGASAPR | 12 |
| 1151.241 | 6 | 15 | PSETEPAAPR | 13 |
| 3140.68 | 26 | 56 | RVFLAAFAAALGPLSFGFALGYSSPAIPSLQRA | 14 |
| 2916.29 | 64 | 93 | RLDDAAASWFGAVVTLGAAAGGVLGGWLVDRA | 15 |
| 889.04 | 216 | 223 | RQEAMAALRF | 16 |
| 2984.32 | 224 | 249 | RFLWGSEQGWEDPPIGAEQSFHLALLRQ | 17 |
| 4263.10 | 427 | 463 | KEFSSLMEVLRPYGAFWLASAFCIFSVLFTLFCVPEIKG | 18 |
| 1401.54 | 466 | 477 | KTLEQITAHFEGR | 19 |
| | 292 | 302 | SLASVVVGVIQ | 20 |

We claim:

1. A cancer-associated variant of glucose transporter 8, comprising the amino acid sequence of SEQ ID NO:11.

2. A cancer-associated variant of glucose transporter 8, comprising the amino acid sequence of SEQ ID NO:12.

3. A cancer-associated variant of glucose transporter 8, comprising the amino acid sequence of SEQ ID NO:13.

4. A cancer-associated variant of glucose transporter 8, consisting of the amino acid sequence of SEQ ID NO:11.

5. A pharmaceutical composition comprising an effective amount of a cancer-associated variant of glucose transporter 8 comprising the amino acid sequence of SEQ ID NO:11, 12 or 13, in admixture with a suitable diluent or carrier.

6. The pharmaceutical composition of claim 5, further comprising an adjuvant.

7. A kit comprising the pharmaceutical composition according to claim 5 and instructions for use thereof.

* * * * *